US011375884B2

(12) United States Patent
Shahinian et al.

(10) Patent No.: US 11,375,884 B2
(45) Date of Patent: *Jul. 5, 2022

(54) MULTI-ANGLE REAR-VIEWING ENDOSCOPE AND METHOD OF OPERATION THEREOF

(71) Applicants: Hrayr Karnig Shahinian, Northport, NY (US); California Institute of Technology, Pasadena, CA (US)

(72) Inventors: Hrayr Karnig Shahinian, Beverly Hills, CA (US); Michael J. Shearn, Santa Barbara, CA (US); Harish Manohara, Glendora, CA (US); Jack M. Mondry, Edina, MN (US); Ronald J. Korniski, Thousand Oaks, CA (US)

( * ) Notice: Subject to any disclaimer, the term of this patent is extended or adjusted under 35 U.S.C. 154(b) by 284 days.

This patent is subject to a terminal disclaimer.

(21) Appl. No.: 15/284,484

(22) Filed: Oct. 3, 2016

(65) Prior Publication Data

US 2017/0020372 A1  Jan. 26, 2017

Related U.S. Application Data

(63) Continuation of application No. 13/628,896, filed on Sep. 27, 2012, now Pat. No. 9,456,735.

(Continued)

(51) Int. Cl.
*A61B 1/00* (2006.01)
*A61B 1/04* (2006.01)
(Continued)

(52) U.S. Cl.
CPC ........ *A61B 1/00183* (2013.01); *A61B 1/0002* (2013.01); *A61B 1/00006* (2013.01);
(Continued)

(58) Field of Classification Search
CPC .. A61B 6/02; A61B 6/022; A61B 3/08; A61B 1/00096; A61B 1/00163;
(Continued)

(56) References Cited

U.S. PATENT DOCUMENTS 1,960,011 A   5/1934  Ives
2,255,631 A   9/1941  Shulman
(Continued)

FOREIGN PATENT DOCUMENTS

EP   0469966 B1   2/1992
EP   1371321 A1   12/2003
(Continued)

OTHER PUBLICATIONS

Y.S. Heo, "Illumination and Camera Invariant Stereo Matching," Computer Vision and Pattern Recognition, 2008. CVPR 2008. IEEE Conference, vol. No., pp. 1-8, Jun. 23-28, 2008.
(Continued)

*Primary Examiner* — Ryan N Henderson

(57) ABSTRACT

A rear-viewing endoscope includes a rigid section having first and second ends, and a cavity situated between the first and second ends. The rigid section has a longitudinal length and defining a longitudinal axis (LAR). The endoscope further includes a flexible section having proximal and distal ends, where the proximal end is coupled to the second end of the rigid section; and an imaging unit having first and second ends and a cavity situated between the first and second ends, the second end of the imaging unit coupled to the distal end of the flexible section. An objective lens assembly of the endoscope includes a complementary multiband bandpass filter (CMBF) pair situated within the cavity of the imaging unit. The CMBF filter collimated image rays passing therethrough so as to output filtered image rays. A
(Continued)

camera or detector receives the filtered image rays and forms corresponding video information for stereoscopic imaging.

16 Claims, 38 Drawing Sheets

Related U.S. Application Data

(60) Provisional application No. 61/539,842, filed on Sep. 27, 2011.

(51) Int. Cl.
*A61B 1/008* (2006.01)
*A61B 1/005* (2006.01)
*A61B 1/05* (2006.01)

(52) U.S. Cl.
CPC ............ *A61B 1/008* (2013.01); *A61B 1/0011* (2013.01); *A61B 1/00016* (2013.01); *A61B 1/0055* (2013.01); *A61B 1/00174* (2013.01); *A61B 1/00186* (2013.01); *A61B 1/00188* (2013.01); *A61B 1/00193* (2013.01); *A61B 1/04* (2013.01); *A61B 1/05* (2013.01)

(58) Field of Classification Search
CPC ............ A61B 1/00165; A61B 1/00167; A61B 1/0017; A61B 1/00174; A61B 1/00177; A61B 1/00179; A61B 1/00181; A61B 1/00183; A61B 1/00186; A61B 1/00188; A61B 1/0019; A61B 1/00193; A61B 1/00197; A61B 1/002; A61B 1/04; A61B 1/041; A61B 1/042; A61B 1/043; A61B 1/045; A61B 1/05; A61B 1/051; A61B 1/053; A61B 1/055
See application file for complete search history.

(56) References Cited

U.S. PATENT DOCUMENTS

| | | | |
|---|---|---|---|
| 3,870,037 A | 3/1975 | Cadariu et al. | |
| 4,651,201 A | 3/1987 | Schoolman | |
| 4,759,348 A | 7/1988 | Cawood | |
| 4,761,066 A | 8/1988 | Carter | |
| 4,873,572 A | 10/1989 | Miyazaki et al. | |
| 4,877,307 A | 10/1989 | Kalmanash | |
| 4,951,676 A | 8/1990 | Collet-Billon | |
| 5,050,226 A | 9/1991 | Collet-Billon | |
| 5,105,269 A | 4/1992 | Nakamura et al. | |
| 5,191,203 A * | 3/1993 | McKinley | G02B 23/2415 |
| | | | 359/652 |
| 5,192,969 A | 3/1993 | Igarashi et al. | |
| 5,222,477 A | 6/1993 | Lia | |
| 5,305,098 A | 4/1994 | Matsunaka et al. | |
| 5,395,030 A | 3/1995 | Kuramoto et al. | |
| 5,436,655 A | 7/1995 | Hiyama et al. | |
| 5,459,605 A | 10/1995 | Kempf | |
| 5,471,237 A | 11/1995 | Shipp | |
| 5,494,483 A | 2/1996 | Adair | |
| 5,536,234 A | 7/1996 | Newman | |
| 5,540,229 A | 7/1996 | Collet-Billon et al. | |
| 5,547,455 A | 8/1996 | McKenna et al. | |
| 5,603,687 A | 2/1997 | Hori et al. | |
| 5,605,532 A | 2/1997 | Schermerhorn | |
| 5,649,897 A * | 7/1997 | Nakamura | A61B 1/05 |
| | | | 348/45 |
| 5,662,584 A | 9/1997 | Hori et al. | |
| 5,667,473 A | 9/1997 | Finn et al. | |
| 5,673,147 A * | 9/1997 | McKinley | A61B 1/00193 |
| | | | 359/462 |
| 5,697,891 A | 12/1997 | Hori | |
| 5,743,846 A * | 4/1998 | Takahashi | G02B 23/2415 |
| | | | 600/166 |
| 5,743,847 A | 4/1998 | Nakamura et al. | |
| 5,751,341 A | 5/1998 | Chaleki et al. | |
| 5,782,752 A | 7/1998 | Lichtman et al. | |
| 5,810,716 A | 9/1998 | Mukherjee et al. | |
| 5,817,014 A | 10/1998 | Hori et al. | |
| 5,823,940 A | 10/1998 | Newman | |
| 5,827,323 A | 10/1998 | Tieman et al. | |
| 5,828,487 A | 10/1998 | Greening et al. | |
| 5,835,194 A | 11/1998 | Morton | |
| 5,841,887 A | 11/1998 | Kuwayama et al. | |
| 5,855,549 A | 1/1999 | Newman | |
| 5,895,350 A | 4/1999 | Hori | |
| 5,928,137 A | 7/1999 | Green | |
| 5,935,057 A | 8/1999 | Lichtman et al. | |
| 5,941,817 A | 8/1999 | Crawford | |
| 5,941,818 A | 8/1999 | Hori et al. | |
| 5,944,654 A | 8/1999 | Drawford | |
| D415,146 S | 10/1999 | Hori | |
| 5,964,696 A | 10/1999 | Mihalca et al. | |
| 5,966,168 A * | 10/1999 | Miyazaki | H04N 7/18 |
| | | | 600/173 |
| 5,984,939 A | 11/1999 | Yoon | |
| 5,989,182 A | 11/1999 | Hori et al. | |
| 6,046,727 A | 4/2000 | Rosenberg et al. | |
| 6,050,939 A | 4/2000 | Pak Wai | |
| 6,066,090 A | 5/2000 | Yoon | |
| 6,086,528 A | 7/2000 | Adair | |
| 6,159,146 A | 12/2000 | El Gazayerli | |
| 6,191,809 B1 | 2/2001 | Hori et al. | |
| 6,211,848 B1 | 4/2001 | Plesniak et al. | |
| 6,223,100 B1 | 4/2001 | Green | |
| 6,275,335 B1 * | 8/2001 | Costales | G02B 30/24 |
| | | | 359/371 |
| 6,277,064 B1 | 8/2001 | Yoon | |
| RE37,356 E | 9/2001 | Hori et al. | |
| 6,290,649 B1 | 9/2001 | Miller et al. | |
| 6,292,221 B1 | 9/2001 | Lichtman | |
| 6,306,082 B1 | 10/2001 | Takahashi et al. | |
| 6,313,883 B1 | 11/2001 | Thaler | |
| 6,383,131 B1 * | 5/2002 | Yamamoto | G02B 23/243 |
| | | | 600/166 |
| 6,419,626 B1 | 7/2002 | Yoon | |
| 6,445,814 B2 | 9/2002 | Lijlma et al. | |
| 6,450,948 B1 | 9/2002 | Matsuura et al. | |
| 6,450,950 B2 | 9/2002 | Irion | |
| 6,517,479 B1 | 2/2003 | Sekiya et al. | |
| 6,593,957 B1 | 7/2003 | Christie | |
| 6,624,935 B2 | 9/2003 | Weissman et al. | |
| 6,632,172 B1 * | 10/2003 | Igarashi | A61B 1/00096 |
| | | | 600/101 |
| 6,647,792 B2 | 11/2003 | Ogawa | |
| 6,682,478 B2 * | 1/2004 | Nakamura | A61B 1/00096 |
| | | | 600/176 |
| 6,731,988 B1 | 5/2004 | Green | |
| 6,817,973 B2 | 11/2004 | Merril et al. | |
| 6,832,984 B2 | 12/2004 | Stelzer et al. | |
| 6,855,110 B2 * | 2/2005 | Igarashi | A61B 1/00096 |
| | | | 600/166 |
| 6,916,286 B2 | 7/2005 | Kazakevich | |
| 6,976,956 B2 | 12/2005 | Takahashi et al. | |
| 6,980,676 B2 | 12/2005 | Pineau | |
| 6,991,602 B2 | 1/2006 | Nakazawa et al. | |
| 6,997,871 B2 | 2/2006 | Sonnenschein et al. | |
| 7,043,062 B2 | 5/2006 | Gerard et al. | |
| RE39,342 E | 10/2006 | Starks et al. | |
| 7,153,259 B2 | 12/2006 | Matsuzawa et al. | |
| 7,154,527 B1 | 12/2006 | Goldstein et al. | |
| 7,241,262 B2 | 7/2007 | Adler et al. | |
| 7,553,277 B2 | 6/2009 | Hoefig et al. | |
| 7,601,119 B2 | 10/2009 | Shahinian | |
| 7,621,869 B2 | 11/2009 | Ratnakar | |
| 8,235,887 B2 * | 8/2012 | Bayer | A61B 1/05 |
| | | | 600/113 |
| 8,585,584 B2 * | 11/2013 | Ratnakar | A61B 1/126 |
| | | | 600/113 |
| 8,814,779 B2 * | 8/2014 | Shafer | A61B 1/04 |
| | | | 348/45 |

(56) References Cited

U.S. PATENT DOCUMENTS

| | | | |
|---|---|---|---|
| 2001/0012053 A1* | 8/2001 | Nakamura | A61B 1/00193 348/45 |
| 2002/0030678 A1 | 3/2002 | Ostermann | |
| 2002/0035330 A1* | 3/2002 | Cline | G16Z 99/00 600/478 |
| 2002/0049367 A1 | 4/2002 | Irion et al. | |
| 2002/0131170 A1* | 9/2002 | Costales | G02B 30/34 359/464 |
| 2002/0154215 A1 | 10/2002 | Schechterman et al. | |
| 2002/0161278 A1* | 10/2002 | Nakamura | G02B 23/243 600/111 |
| 2003/0053744 A1 | 3/2003 | Makio | |
| 2003/0125608 A1* | 7/2003 | Igarashi | A61B 1/00101 600/166 |
| 2003/0174208 A1 | 9/2003 | Glukhovsky et al. | |
| 2003/0233024 A1* | 12/2003 | Ando | A61B 1/00193 600/111 |
| 2004/0019255 A1 | 1/2004 | Sakiyama | |
| 2004/0070667 A1 | 4/2004 | Ando | |
| 2004/0249367 A1 | 12/2004 | Saadat et al. | |
| 2005/0065657 A1 | 3/2005 | Green | |
| 2005/0065658 A1 | 3/2005 | Green | |
| 2005/0119530 A1 | 6/2005 | Douglas et al. | |
| 2005/0228230 A1 | 10/2005 | Schara et al. | |
| 2005/0234296 A1 | 10/2005 | Saadat et al. | |
| 2005/0234297 A1 | 10/2005 | Devierre et al. | |
| 2005/0259335 A1* | 11/2005 | Nishioka | G02B 26/0825 359/726 |
| 2005/0261548 A1 | 11/2005 | Machiya et al. | |
| 2005/0278711 A1 | 12/2005 | Silva et al. | |
| 2006/0015008 A1 | 1/2006 | Kennedy | |
| 2006/0111614 A1 | 5/2006 | Saadat et al. | |
| 2006/0224040 A1 | 10/2006 | Khait et al. | |
| 2006/0247495 A1 | 11/2006 | Bacher et al. | |
| 2007/0055103 A1 | 3/2007 | Hoefig et al. | |
| 2007/0055104 A1* | 3/2007 | Kumei | A61B 1/04 600/176 |
| 2007/0112256 A1 | 5/2007 | Terakawa | |
| 2007/0173689 A1 | 7/2007 | Ozaki et al. | |
| 2007/0249932 A1 | 10/2007 | Shahinian | |
| 2007/0255100 A1 | 11/2007 | Barlow et al. | |
| 2008/0151041 A1* | 6/2008 | Shafer | A61B 1/00163 348/E13.001 |
| 2008/0252997 A1* | 10/2008 | Duckett | G02B 23/243 359/753 |
| 2008/0281154 A1 | 11/2008 | Gono et al. | |
| 2008/0284982 A1 | 11/2008 | Richards et al. | |
| 2009/0058998 A1* | 3/2009 | Kagaya | A61B 1/0638 348/68 |
| 2009/0096865 A1* | 4/2009 | McKinley | G02B 23/2415 348/E13.001 |
| 2009/0137893 A1 | 5/2009 | Seibel et al. | |
| 2009/0187072 A1* | 7/2009 | Manohara | A61B 1/00042 600/109 |
| 2010/0006549 A1 | 1/2010 | Pahk et al. | |
| 2011/0115882 A1* | 5/2011 | Shahinian | H04N 13/257 348/E13.001 |
| 2012/0002099 A1* | 1/2012 | Tajiri | H04N 13/296 348/E5.037 |
| 2012/0057251 A1* | 3/2012 | Takato | G02B 23/243 359/749 |
| 2012/0188347 A1* | 7/2012 | Mitchell | A61B 1/00193 348/E13.074 |
| 2012/0224268 A1* | 9/2012 | Takato | G02B 13/18 359/648 |
| 2012/0250165 A1* | 10/2012 | Do | G02B 13/18 359/715 |
| 2012/0320164 A1* | 12/2012 | Lipton | H04N 13/218 348/E13.074 |
| 2013/0038708 A1* | 2/2013 | Iwasaki | G02B 23/2423 348/E7.085 |
| 2013/0050454 A1* | 2/2013 | Ogasawara | G09G 5/10 348/E7.085 |
| 2013/0163092 A1* | 6/2013 | Morita | A61B 1/00188 359/674 |
| 2013/0208101 A1* | 8/2013 | Ono | A61B 1/00045 348/229.1 |
| 2013/0235176 A1* | 9/2013 | Miyano | G03B 17/00 348/335 |
| 2013/0296649 A1* | 11/2013 | Kirma | G02B 23/243 600/109 |
| 2014/0005555 A1* | 1/2014 | Tesar | A61B 17/0206 600/476 |
| 2014/0088361 A1* | 3/2014 | Hrayr | A61B 1/00183 600/109 |
| 2014/0092226 A1* | 4/2014 | Kuriyama | H04N 5/217 348/229.1 |
| 2014/0155717 A1* | 6/2014 | Saito | A61B 5/14542 600/339 |
| 2014/0336460 A1* | 11/2014 | Shafer | A61B 1/04 600/111 |
| 2015/0141759 A1* | 5/2015 | Charles | A61B 90/30 600/201 |
| 2016/0206187 A1* | 7/2016 | Shahinian | A61B 1/00193 |
| 2016/0360953 A1* | 12/2016 | Mitchell | G03B 35/12 |
| 2017/0020372 A1* | 1/2017 | Hrayr | A61B 1/00174 |
| 2017/0245744 A1* | 8/2017 | McDowall | A61B 1/045 |

FOREIGN PATENT DOCUMENTS

| | | | |
|---|---|---|---|
| EP | 1854420 A1 | 11/2007 | |
| EP | 1880657 A1 | 1/2008 | |
| EP | 1989990 A1 | 11/2008 | |
| JP | 04-021105 | 1/1992 | |
| JP | 06-202004 | 7/1994 | |
| JP | 06-237892 | 8/1994 | |
| JP | 10-010468 | 1/1998 | |
| JP | 2000-052289 | 2/2000 | |
| WO | 93/13916 A1 | 7/1993 | |
| WO | 96/35975 A1 | 11/1996 | |
| WO | 99/57900 A1 | 11/1999 | |
| WO | 2000/050927 A2 | 8/2000 | |
| WO | 00/61009 A1 | 10/2000 | |
| WO | 2002037142 A2 | 5/2002 | |
| WO | 2003098913 A2 | 11/2003 | |
| WO | 2005/030328 A2 | 4/2005 | |
| WO | 2005/031433 A1 | 4/2005 | |
| WO | 2005/120327 A2 | 12/2005 | |
| WO | 2008/033356 A2 | 3/2008 | |
| WO | WO-2011070930 A1 * | 6/2011 | G02B 13/001 |
| WO | WO-2012008312 A1 * | 1/2012 | G02B 13/04 |
| WO | WO-2012014678 A1 * | 2/2012 | A61B 1/00006 |

OTHER PUBLICATIONS

J.L. Garb, "Using GIS for spatial analysis of rectal lesions in the human body," International Journal of Health Geographics, 2007, 6:11, Published online Mar. 15, 2007. doi: 10.1186/1476-072X-6-11. PMCID: PMC1839078 BioMed Central Ltd.

J.P. Rice, "A hyperspectral image projector for hyperspectral imagers," SPIE vol. 6565 65650C, (2007).

J.P. Rice, "Hyperspectral image projectors for radiometric applications," BIPM and IOP Publishing Ltd, Metrologia 43 (2006) S61-S65.

J.P. Rice, "Development of hyperspectral image projectors," SPIE vol. 6297, 629701, (2006).

J.M. Medina, "Binocular interactions in random chromatic changes at isoluminance," Opt. Soc. Am., 2006, vol. 23, No. 2, pp. 239-246.

A. Szold, "Seeing is believing-Visualization systems in endoscopic surgery (video, HDTV, stereoscopy, and beyond)," Surgical Endoscopy, 19:55, pp. 730-733, Springer, 2005.

U. D. A Mueller-Richter,"Possibilities and limitations of current stereo-endoscopy," Journal of Surgical Endoscopy, Springer, New York, ISSN 0930-2794 (Print) 1432-2218 (Online) Issue vol. 18, No. 6, Jun. 2004, 18: pp. 942-947.

M.A. Weissman, "Stereo parallax and Disnparity in Single-Lens Stereoscopy," Stereoscopic Displays and Virtual Reality Systems VII, SPIE 3987, pp. 312-320, Apr. 2000.

(56) References Cited

OTHER PUBLICATIONS

G.A. Lester, "Ferroelectric liquid crystal device for a single camera stereoscopic endoscope system," Electronics Letters, 1997, vol. 33, No. 10, pp. 857-858.
G.L. Zimmerman, "Perception at Equiluminance: An Adaptive Model of Motion Metamers," Circuits and Systems, 1994., Proceedings of the 37th Midwest Symposium on , vol. 1, No., pp. 577-580 vol. 1, Aug. 3-5, 1994.
Y. Takemura, "Stereoscopic Video Movie Camera Using 300k Pixel IT-CCD Sensors," IEEE Transactions on Consumer Electronics, Feb. 1991, vol. 37, No. 1, pp. 39-44.
E. Badique, "Use of color image correlation in the retrieval of gastric surface topography by endoscopic stereopair matching," Applied Optics, 1988, vol. 27, No. 5, pp. 941-948.
N. Ohyama, "Compensation of motion blur in CCD color endoscope images," Opt. Soc. Am., 2006, Applied Optics, 1987, vol. 26, No. 5, pp. 909-912.
P. Breedveld and M. Wentink, "Eye-hand coordination in laparoscopy—an overview of experiments and supporting aids," Min Invas Ther & Allied Technol 2001: 155-162, 10(3).
Keijirou Itakura, et al., "A 1-mm 50 k-Pixel IT CCD Image Sensor for Miniature Camera System," IEEE Transactions on Electron Devices, Jan. 2000, 65-70, vol. 47, No. 1.
Jacques Duparré, et al., "Thin compound-eye camera," Applied Optics, May 20, 2005, pp. 2949-2956, vol. 44, No. 15.
Jun Tanida, et al., "Color imaging with an integrated compound imaging system," Optics Express, Sep. 8, 2003, 2019-2117, vol. 11, No. 18.
Jun Tanida, et al., "Thin observation module by bound optics (TOMBO): concept and experimental verification," Applied Optics, Apr. 10, 2001, 1806-1813, vol. 40, No. 11.
Ikeda, M., Sagawa, K., "Binocular color fusion limit," J. of the Optical Society of America, 69(2), 316-321, (Feb. 1979).
Dudley, D., Duncan, W. M., Slaughter, J., "Emerging digital miromirror device (DMD) applications," Proceedings of SPIE 4985, 14-25 (2003).
Hovis, J. K., "Review of Dichoptic Color Mixing," Optometry and Vision Science, 66(3), 181-190 (1998).
Lambooij, M., Ijsselsteijn, W., "Visual discomfort and visual fatique of stereoscopic display: A review," J. of Imaging science and technology, 53(3), 030201 (2009).
DooHyun Lee and InSo Kweon, "A Novel Stereo Camera System by a Biprism," IEEE Transactions On Robotics And Automation, 16(5), 528-541, (Oct. 2000).
Mikko Kyto, Mikko Nuutinen, Pirkko Oittinen, "Method for measuring stereo camera depth accuracy based on stereoscopic vision," OAalto University School of Science and Technology, Department of Media Technology, Otaniementie 17, Espoo, Finland.
Qin, D., Takamatsu, M., Nakashima, Y., Qin, X., "Change of wavelength difference limit for binocular color fusion with wavelength and brightness of stimuli," J. of Light and Visual Environment, 30(1), 43-45 (2006).
Jung, Y. J., Sohn, H., Lee, S., Ro, Y. M., and Park, H. W., "Quantitative measurement of binocular color fusion limit for non-spectral colors.," Optics express, 19(8), 7325-7338 (2011).
Planar Systems Inc., "SD1710 Pruduct User's Guide," 1-12 (2005).
CRI Varispec," Liquid Crystal Tuneable Filters," 1-12 (2005).
Avi Yaron, Mark Shechterman and Nadav Horesh, "Blur spot limitations in distal endoscope sensors," Proc. SPIE 6055, Stereoscopic Displays and Virtual Reality Systems XIII, 605509 (Jan. 27, 2006).
Researchers Work on Snake-Like 'Rescue Robots', downloaded on Apr. 20, 2006 from http://www.foxnew5.com/printer_friendly_story/O,3566, 192430,OO.htm.
NASA Infrared Camera Helps Surgeons Map Brain Turners, Jul. 15, 2004,downloaded on Apr. 24, 2006 from http://www.jpl.nasa.gov/news/news.cfm?release=20D4-183.
Fung et al., "A Case Study of 3D Stereoscopic VS. 20 Monoscopic Tele-Reality In . . . " IEEE/RSJ International Conference on Intelligent Robots and Systems, 2005, pp. 181-186.
Nain et al., "Three-Dimensional Nanoscale Manipulation and Manufacturing Using Proximal Probes: Controlled Pulling of Polymer . . . " IEEE Int Conf Rob Autom vol. 1,2004, pp. 434-439.
Lytle et al., Adapting a Teleoperated Device for Autonomous Control Using Three-Dimensional Positioning sensors: . . . Automation in Construction, vol. 13, 2004, pp. 101-118.
Mezouar et al., Robustness of Central Catadioptric Image-based Visual . . . • IEEE RSJ Int. Conf. IntelL Robots and Syst. IROS, vol. 2, Sep. 28-Oct. 2, 2004, Sendai, JP, pp. 1389-1394.
Murakami et al., "Automatic Insertion Work. Based on Visual Measurement and Contact Force Estimation" Proc IEEE Int Conf Rob Autom, vol. 4, May 2002, pp. 4167-4172.
Trivedi et al., "A Vision System for Robotic Inspection and Manipulation", DE90 005412, Univ of Tennessee, Revised Mar. 1989. pp 1-12.
Nguyen et al., "30 Model Control of Image Processing" In JPL, California Inst. of Tech., Proceedings of the NASA Conference on Space Telerobotics, vol. 3, pp. 213-222 May 2000.
Stiel et af. Digital Flashing Tomosynthesis: A Promising Technique for Angiocardiographic ScreeningD IEEE Transactions on Medical Imaging, Jun. 1993, No. 2, NY, pp. 314-321.
Fritz, Eric., "High Speed Generation of Illumination Spectra for a Stereoscopic Endoscope", http://hdl.handle.net/2014/42272, NASA Undergraduate Student Research Program (USRP), Pasadena, California, Aug. 9, 2011, pp. 1-8, Retrieved from Internet: URL: http://trs-new.jpl.nasa.gov/dspace/bitstream/2014/42272/1/11-3811.pdf.
Ream, Allen, "Project report: reducing color rivalry in imagery for conjugated multiple bandpass filter based stereo endoscopy", http://hdl.handle.net/2014/42276, NASA Undergraduate Student Research Program (USRP), Pasadena, California, Aug. 2011, pp. 1-9, Retrieved from Internet: URL: http://trs-new.jpl.nasa.gov/dspace/bitstream/2014/42276/1/11-3803.pdf.
J.P. Rice et al., "Hyperspectral image compressive projection algorithm," SPIE vol. 7334 pp. 733414-1, , XP055046293, ISSN: 0277-786X, DOI: 10.1117/12.818844, (Apr. 27, 2009).
Sam Bae et al, "Toward a 3D endoscope minimally invasive surgery", SPIE Newsroom, Sep. 21, 2011, pp. 1-3, XP055046098, DOI: 10.1117/2.1201109.003810.
NASA's Jet Propulsion Laboratory et al: "Stereo Imaging Miniature Endoscope", Internet Citation, Jun. 30, 2011 (Jun. 30, 2011), pp. 6-7, XP002687431, Retrieved from the Internet: URL:http://ntrs.nasa.gov/archive/nasa/casi.ntrs.nasa.gov/20110012587_2011013131.pdf [retrieved on Dec. 3, 2012].
Ronald Korniski et al: "3D imaging with a single-aperture 3-mm objective lens: concept, fabrication, and test", Proceedings of SPIE, vol. 8144, Sep. 14, 2011 (Sep. 14, 2011), p. 812904, XP055046246, ISSN: 0277-786X, DOI: 10.1117/12.894110.

* cited by examiner

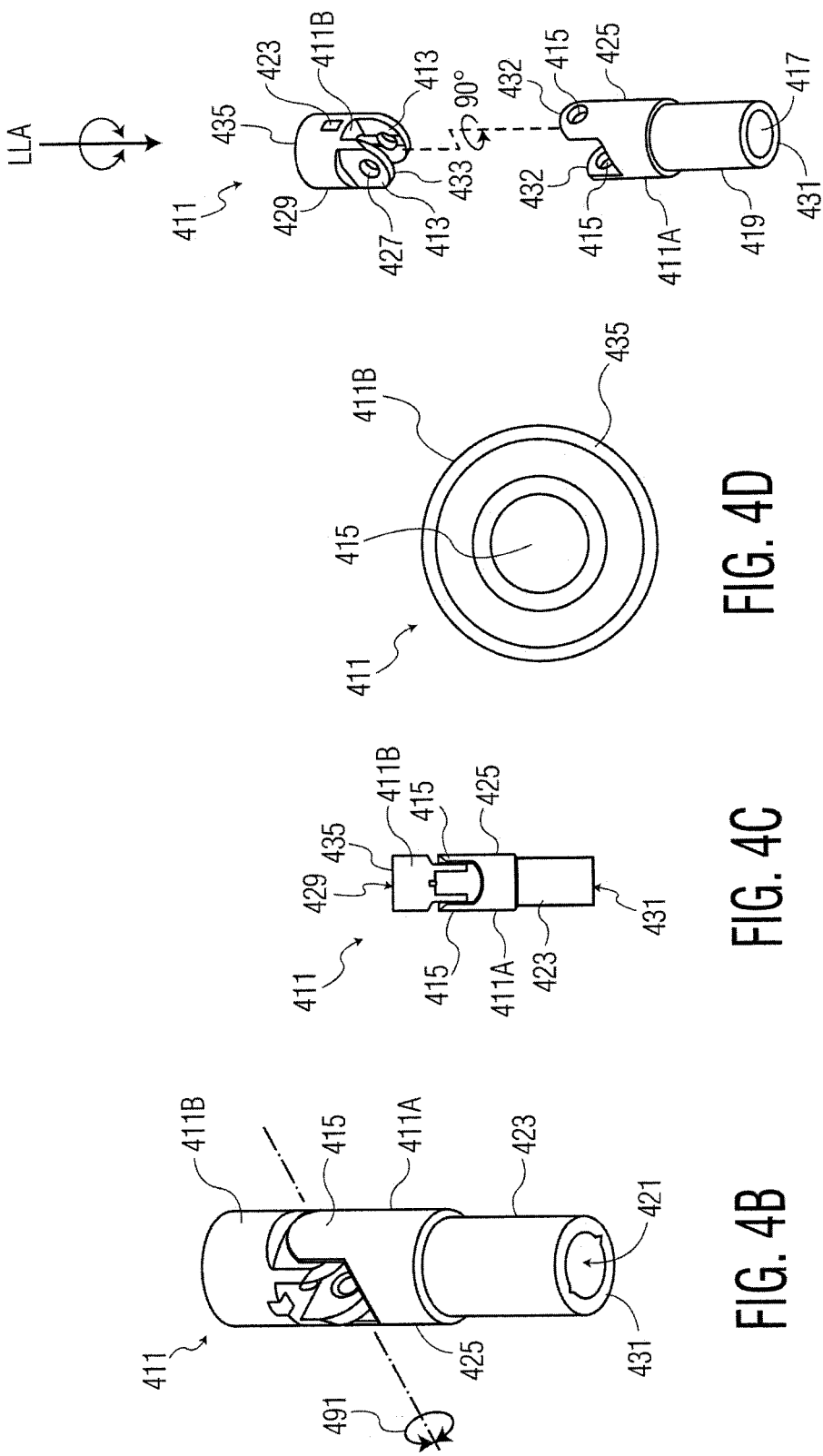

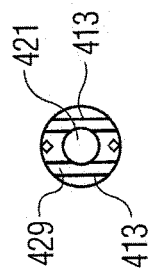
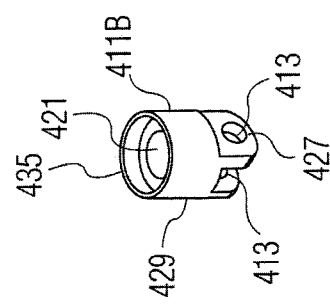
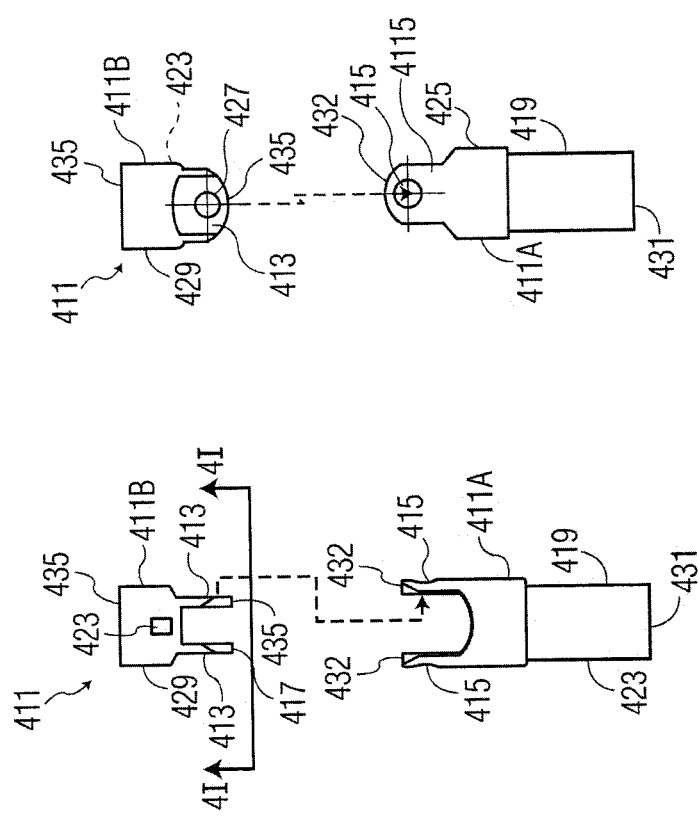

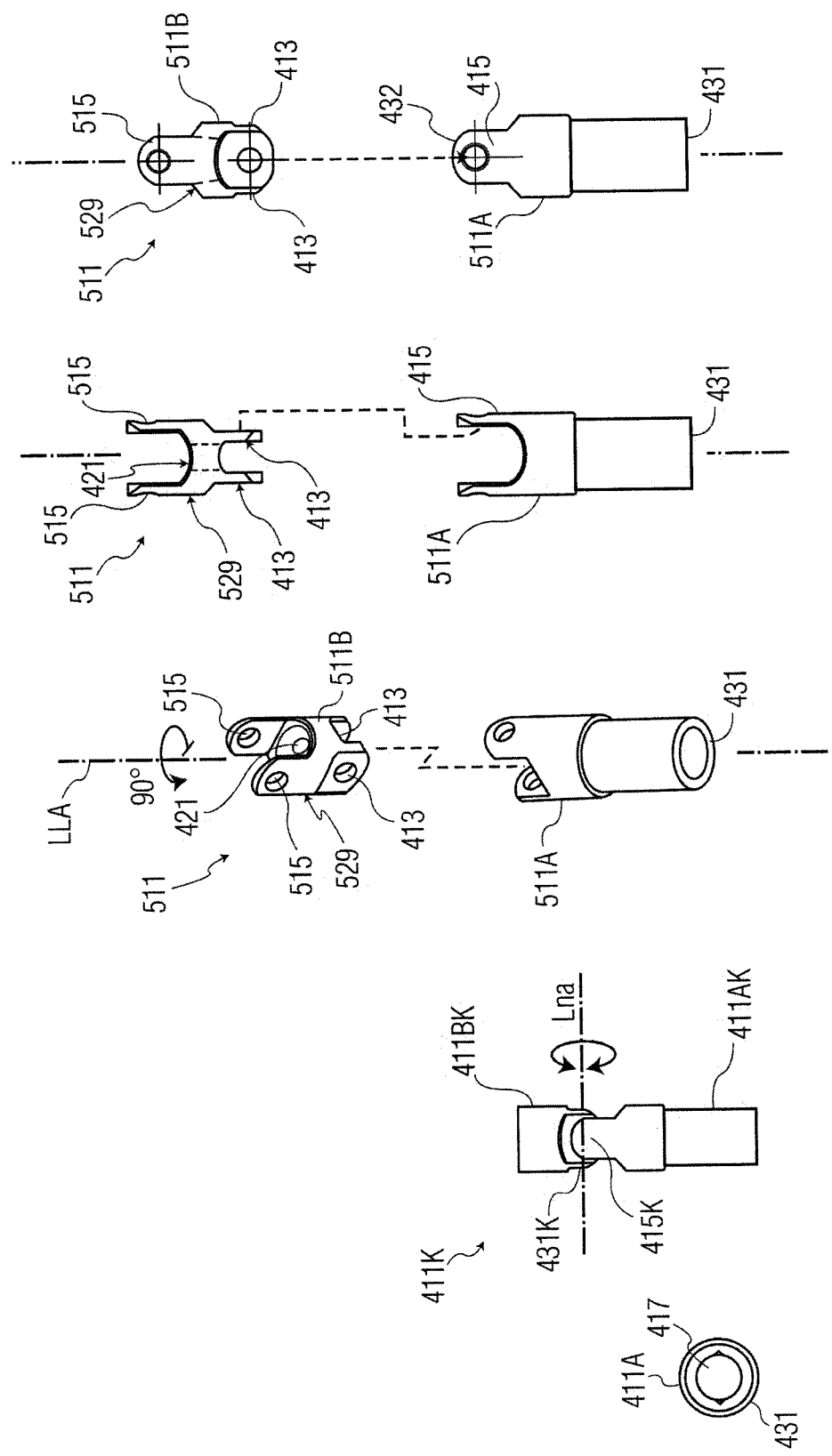

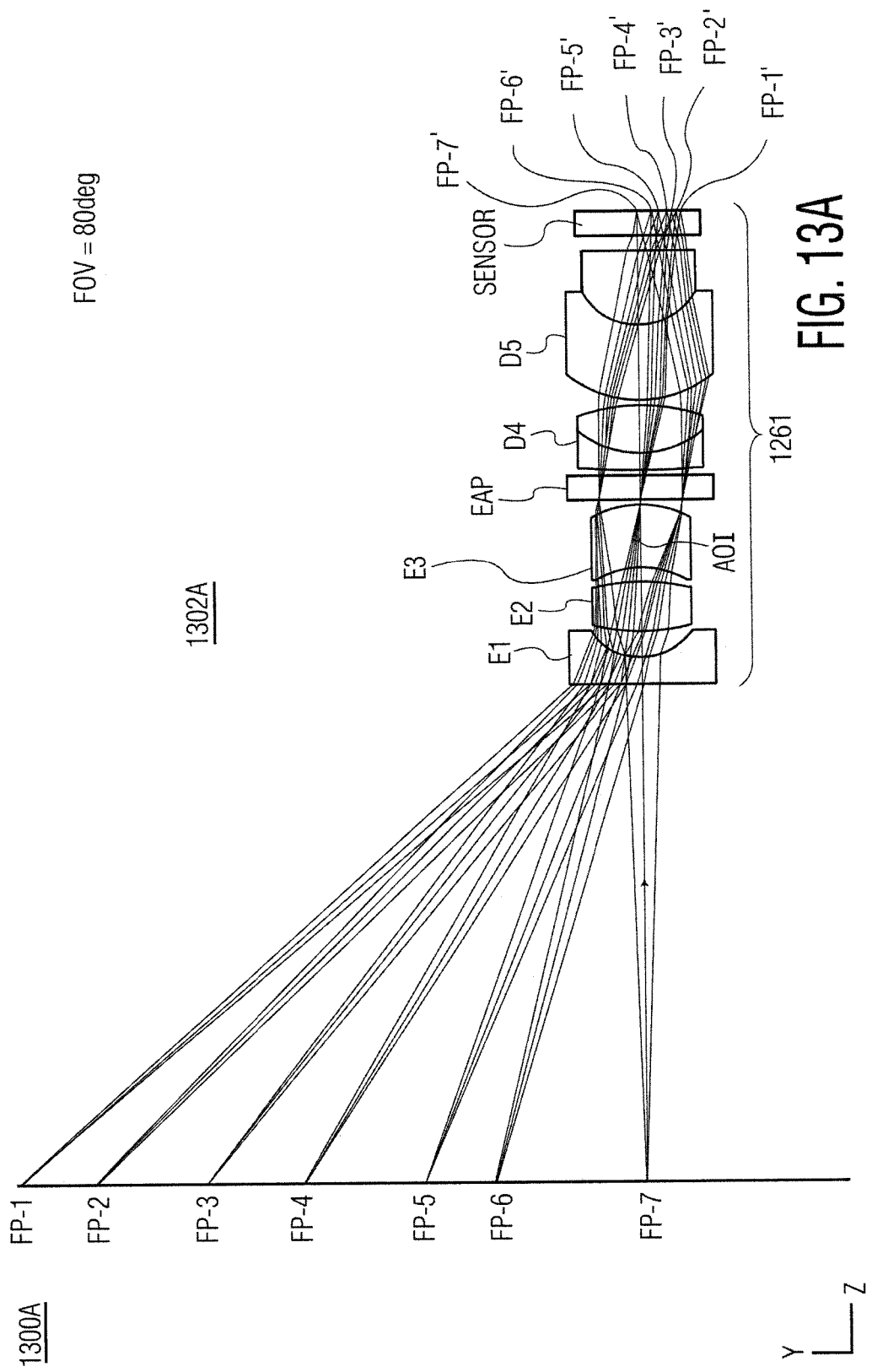

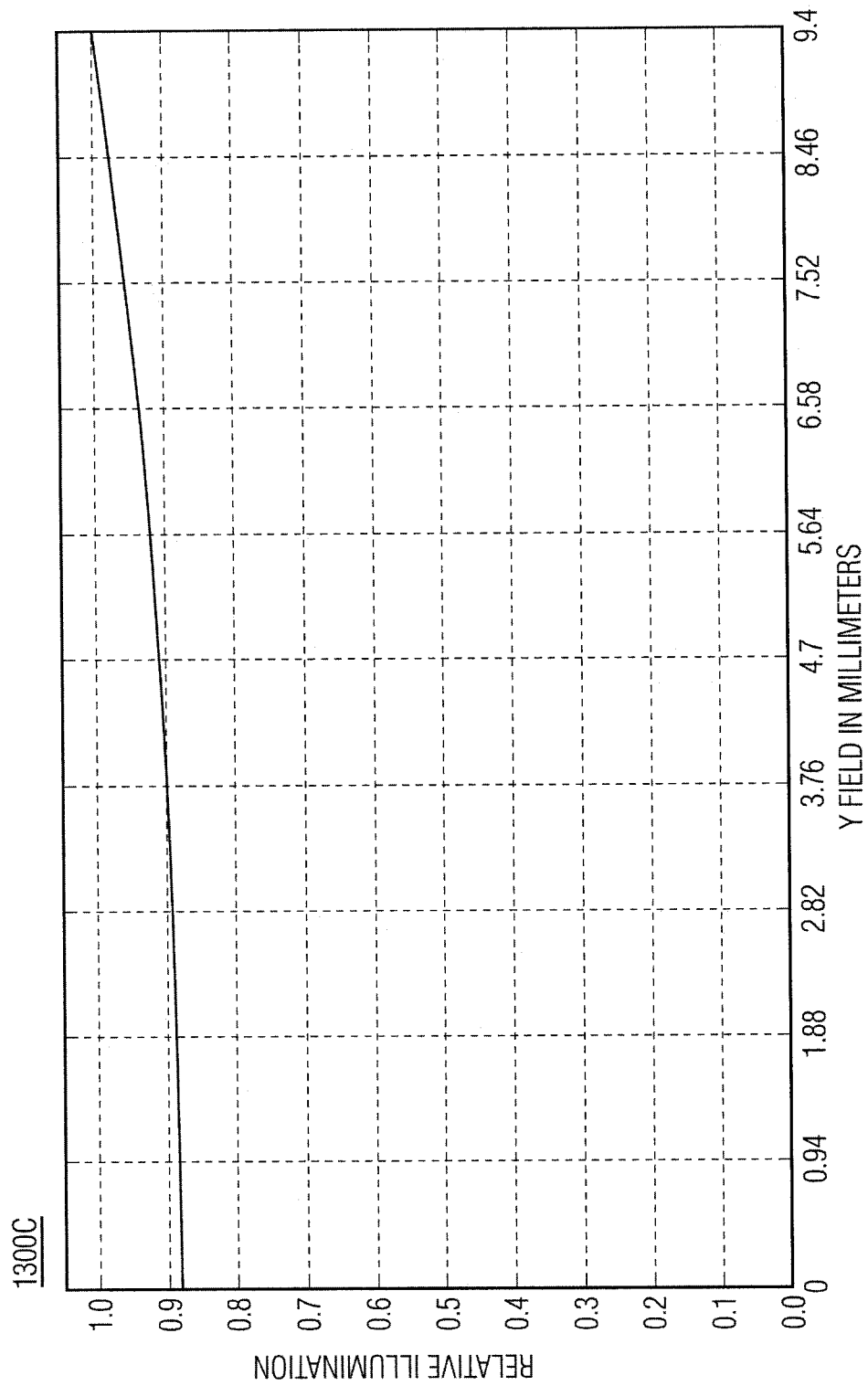

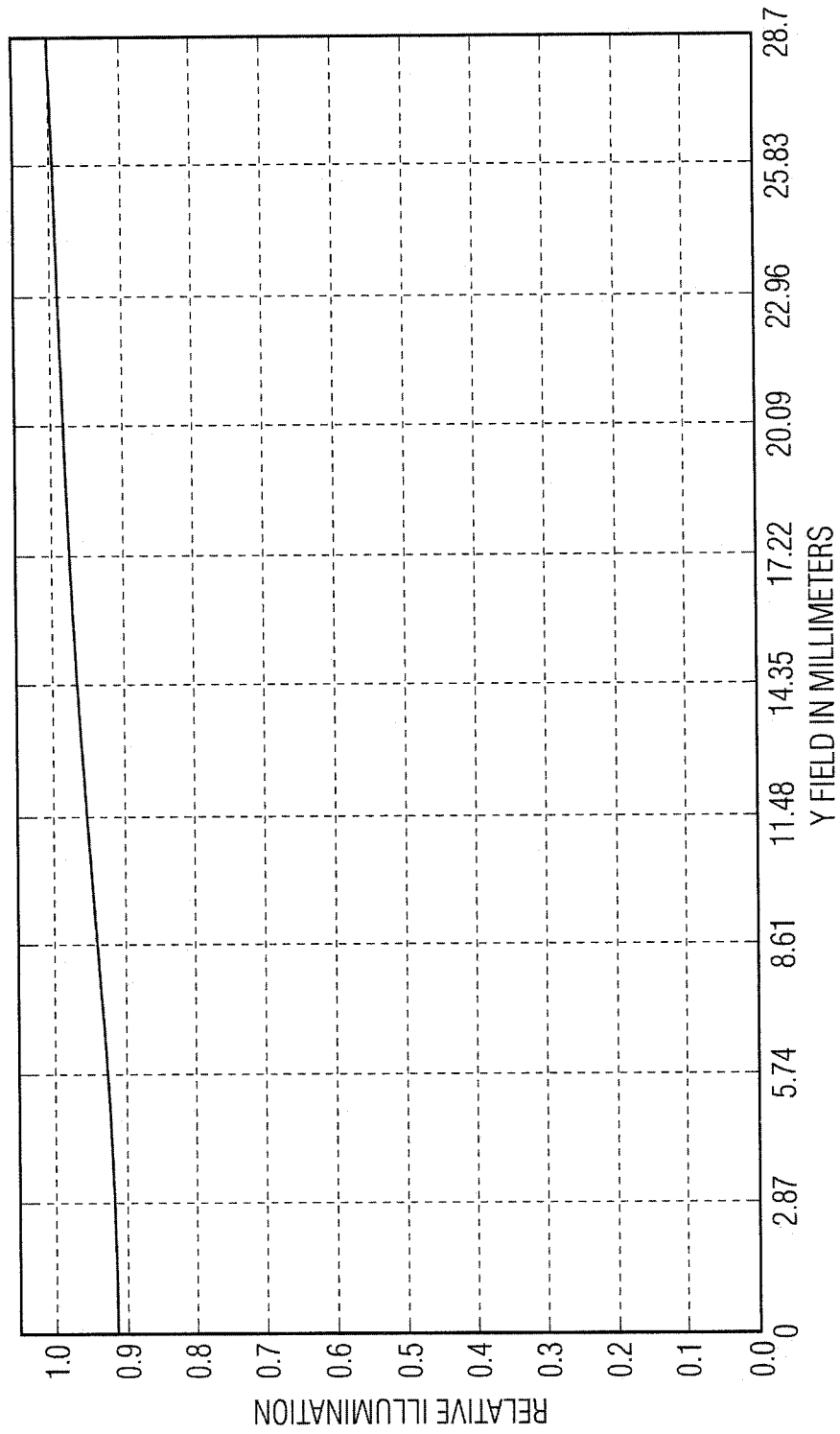

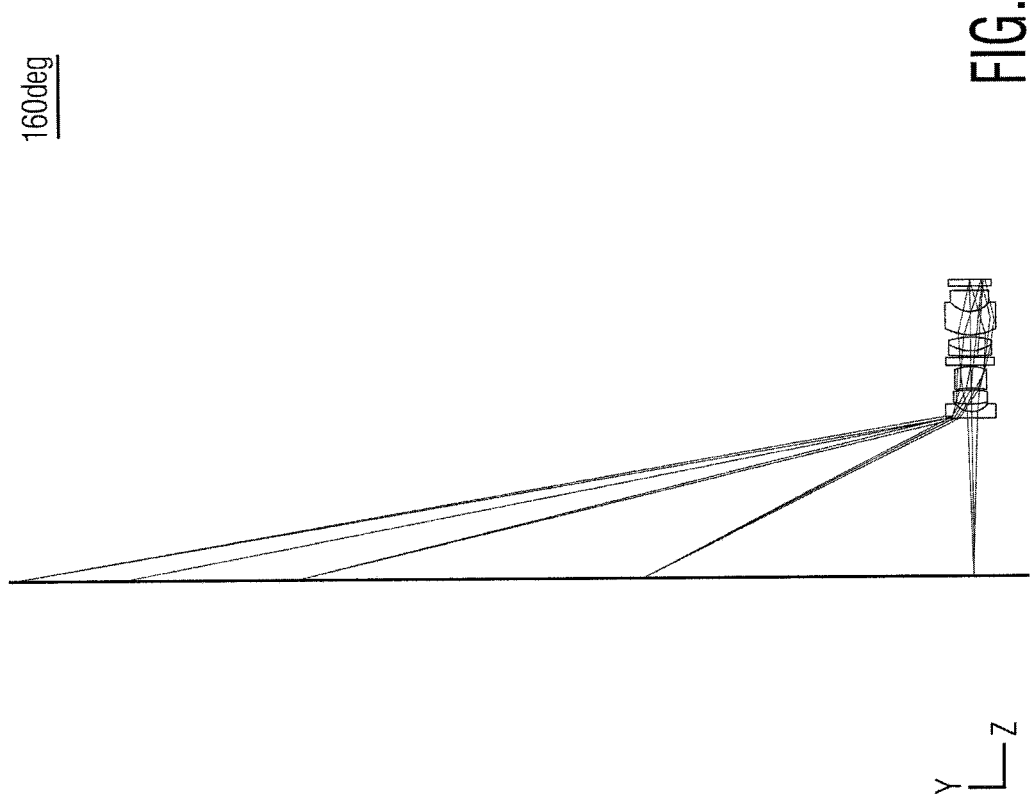

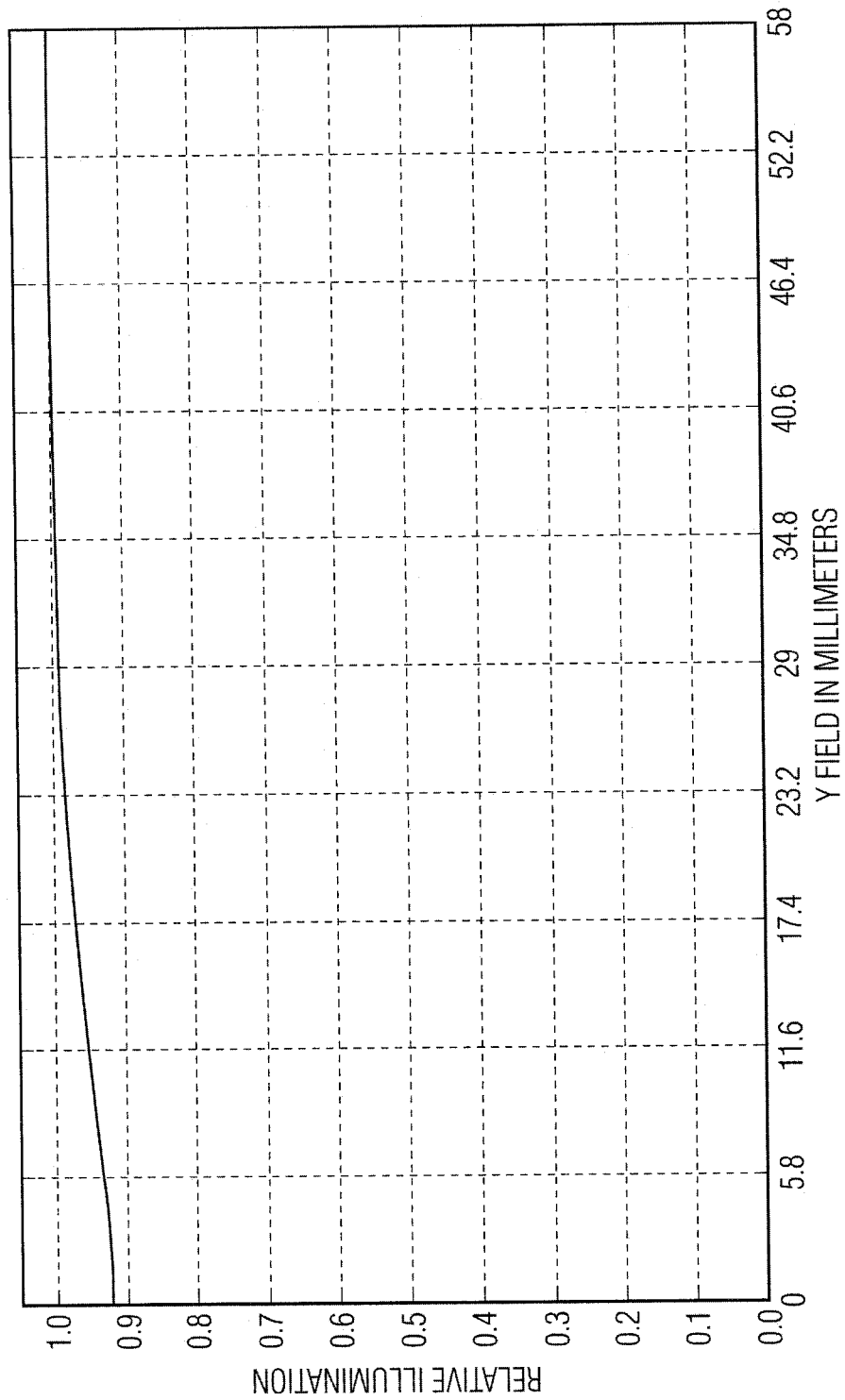

```
// PWM control for SMA wire using Joystick shield
const int wirePin = 9;
const byte buttonPin = 3;
const byte increasePin = 4;
const byte decreasePin = 5;
int button = 0;
int duty = 0;
int increase = 0;
int decrease = 0;
void setup( )
{
Serial.begin(9600);
pinMode(wirePin, OUTPUT);
pinMode(buttonPin, INPUT);
digitalWrite(buttonPin, HIGH);
digitalWrite(increasePin, HIGH);
digitalWrite(decreasePin, HIGH);
}
void loop ( )
{
button = digitalRead(buttonPin);
if(button == LOW)
{
analogWrite(wirePin, duty);
if(!digitalRead(increasePin) || !digitalRead(decreasePin))
{
if(!digitalRead(increasePin))
{
// increase duty cycle
duty = duty + 20;
}
else
{
// decrease duty cycle
duty = duty - 20;
}
// enforce limits
if(duty <= 0)
{
duty = 0;
}
if(duty >= 255)
{
duty = 255;
}
}
// wait for user to lift finger
while (!digitalRead(increasePin) || !digitalRead(decreasePin)) {
delay(50);
}
}
else {
analogWrite(wirePin, 0);
}
}
```

FIG. 21

MULTI-ANGLE REAR-VIEWING ENDOSCOPE AND METHOD OF OPERATION THEREOF

This application claims is a continuation of prior U.S. patent application Ser. No. 13/628,896 filed Sep. 27, 2012, now U.S. Pat. No. 9,456,735 B2, issued on Oct. 4, 2016, which claims the benefits of U.S. Provisional Patent Application Ser. No. 61/539,842 filed Sep. 27, 2011, which is incorporated herein by reference in its entirety.

The invention described herein was made in the performance of work under a NASA contract, and is subject to the provisions of Public Law 96-517 (35 USC 202) in which the Contractor has elected to retain title.

Further, each of the following patents or patent applications is incorporated herein by reference in its entirety:

(1) U.S. Pat. No. 7,601,119 B2, to Shahinian, entitled "Remote Manipulator with Eyeballs," filed on Apr. 25, 2006 and issued on Oct. 13, 2009;

(2) U.S. Patent Application Publication No. 2009/0187072 A1 to Manohara, et al., entitled "Endoscope and System and Method of Operation thereof," filed on Dec. 18, 2008;

(3) U.S. Patent Application Publication No. 2011/0115882 A1, to Shahinian, et al., entitled "Stereo Imaging Miniature Endoscope with Single Imaging Chip and Conjugated Multi-Bandpass Filters," filed on Nov. 15, 2010; and (4) U.S. patent application Ser. No. 13/628,788, filed on Sep. 27, 2012, and published as U.S. Patent Application Publication No. 2014/0085420, now U.S. Pat. No. 9,295,375, to Shahinian, et al., claiming priority to U.S. Provisional Patent Application Ser. No. 61/539,808 filed on Sep. 27, 2011, entitled "Programmable Spectral Source and Design Tool for 3D Imaging Using Complementary Bandpass Filters."

The present system relates generally to medical imaging systems and, more particularly, to an endoscopic viewing system having an adjustable viewing angle which can provide forward and rear views, and a method of operation thereof.

Minimally invasive procedures can include surgical and other procedures, which are typically less invasive than traditional open procedures such as, for example, open surgery. A typical minimally invasive surgical (MIS) procedure usually involves the manipulation of one or more endoscopic devices that can be inserted through an opening or incision and an endoscope or the like to observe a surgical area (or field).

During minimally invasive endoscopic (e.g., laparoscopic) surgical procedures, surgeons typically utilize endoscopes to view a surgical field and thereby acquire a clear view of anatomical structures in the surgical field. As minimally invasive surgery is typically performed through a small opening or incision, surgeons cannot view the surgical field directly but must rely instead upon an endoscope to provide an image of a surgical field. As the small opening or incision through which the endoscope passes is typically about the size of a dime, the range of operation of the endoscope within a surgical field is typically limited. Further, as most endoscopes typically provide a forward line-of-sight image as opposed to a rear view, a surgeon may have to rely upon a compromised view of a surgical field during a minimally invasive surgical procedure.

With respect to endoscopes, these devices typically fall into two types: a fixed (or rigid) type and a flexible type. The fixed type typically includes a fixed body portion and the flexible type includes a flexible body portion.

With regard to the typical fixed-type endoscope, the viewing portion (which is used to obtain real-time images) on this type of endoscope only provides a forward view as opposed to a rearview (e.g., a view towards a handle side of the endoscope). Thus, the typical fixed-type endoscope can only provide a forward view of an operating field. Accordingly, in order to obtain a rear view of a surgical field, it may be necessary to insert another endoscope into another incision. However, making another incision may not always be possible and may also have a detrimental effect on a patient and on a surgical procedure being performed. For example, it may be difficult or impossible to use a second fixed-type endoscope to obtain a rear view during cranial surgery. Further, conventional flexible endoscopes may be ill suited for cranial surgery as they can typically only provide large radius bends.

Further, with regard to a flexible-type endoscope, although this endoscope can be manipulated to move a viewing portion, it is difficult to determine where the viewing portion is located and a direction in which the viewing portion is pointing. Accordingly, it is difficult to determine a viewing orientation of a flexible-type endoscope and, thus, difficult to determine a spatial orientation with respect to a surgical field. Further, although a conventional flexible-type endoscope can be manipulated to form bends, these bends are large radius bends and ill suited for cranial MIS procedures. Accordingly, flexible-type endoscopes may not be suitable for viewing a surgical field during surgery.

Accordingly, there is a need for an endoscope that can provide a rear view of a surgical field. One object of the present systems, methods, apparatuses, and devices (hereinafter system unless context indicates otherwise) is to overcome the disadvantages of conventional systems and devices. According to one illustrative embodiment, a medical imaging system may include an endoscope including: a rigid section having opposed first and second ends and an opening situated between the first and second ends, the rigid section defining a longitudinal axis; a handle portion coupled to a first end of the rigid section and having first and second scissor-type handles suitable for grasping by a user; and a base part having an image capturing device, the base part situated at the second end of the rigid section and coupled to the first handle of the scissor-type handles such that a displacement of the one of the scissor-type handles relative to the other of the scissor-type handles causes a change in a viewing direction of image capturing device.

In addition or alternate to the scissor-type handles at the proximal end of the endoscope, any other suitable moving means may be used, such as a joystick that controls an actuator to provide movement of the distal end of the endoscope in response to moving the joystick by the operator. The joystick may be at the proximal end of the endoscope and/or wirelessly connected to an actuator of the endoscope.

In accordance with an aspect of the present system, there is disclosed a rear-viewing endoscope, including: a rigid section having first and second ends, and a cavity situated between the first and second ends, the rigid section having a longitudinal length and defining a longitudinal axis (LAR); a flexible section having proximal and distal ends, the proximal end coupled to the second end of the rigid section; an imaging unit having first and second ends and a cavity situated between the first and second ends, the second end of the imaging unit coupled to the distal end of the flexible section; an objective lens assembly comprising a complementary multiband (e.g., triple) bandpass filter (CMBF) pair situated within the cavity of the imaging unit for filtering collimated image rays passing therethrough so as to output filtered image rays; and a camera which receives the filtered image rays and forms corresponding video information for stereoscopic imaging.

It is envisioned that objective lens assembly may include a first lens group, wherein the collimated image rays pass which pass through the CMBF pair were collimated by the first lens group. Further, the collimated image rays which pass through the CMBF pair may have a minimal angle of incidence (AOI) which is less than or equal to a threshold angle of incidence (TAOI) value. Moreover, the TAOI may have a value of 25 degrees. Further, objective lens assembly may further include a second lens group which receives the filtered image rays from the CMBF pair and focuses the filtered image rays upon an imaging plane. Moreover, the camera may further include a detector array at the imaging plane, the detector array detecting the filtered image rays focused upon the imaging plane and forming corresponding stereoscopic image information. It is also envisioned that CMBF pair may be formed upon a surface of a lens of the second lens group and/or formed on a dual aperture lens situated between the first and second lens groups, where a right aperture has a right CMBF and the left aperture has the left CMBF, where the right CMBF is the complement of the left CMBF.

In accordance with yet another aspect of the present system, there is provided a method of forming a rear-viewing endoscope to capture stereoscopic images of a subject, the method may include one or more acts of: obtaining a rigid section having first and second ends, and a cavity situated between the first and second ends, the rigid section having a longitudinal length and defining a longitudinal axis (LAR); coupling a flexible section to the rigid section; coupling an imaging unit having first and second ends and a cavity situated between the first and second ends to the flexible section; placing an objective lens assembly comprising a complementary multiband bandpass filter (CMBF) pair within the cavity of the imaging unit, the CMBF being configured to filter image rays incident thereupon and output corresponding filtered image rays; and placing a camera having a sensor array in the cavity and to a first side of the CMBF pair.

The method may further include an act of placing first and second lens groups in the lens assembly and about opposite sides of the CMBF, wherein the first lens group is configured to collimate image rays passing therethrough and provide collimated image rays to the CMBF pair. Moreover, the first lens group may be configured such that the collimated image rays have a minimal angle of incidence (AOI) which is less than or equal to a threshold angle of incidence (TAOI) value. The TAOI value may be 25 degrees. However, other values and/or ranges are also envisioned. Moreover, it is envisioned that the second lens group may be configured to: receive the filtered image rays output from the CMBF pair; and focus the filtered image rays upon the sensor array of the camera. Further, the camera may be configured process the image rays focused upon the sensor array and form corresponding stereoscopic image information. The method may further include acts of forming the CMBF pair upon a surface of a lens of the second lens group, and/or placing a limiting aperture portion between the first and second lens groups, and forming the CMBF pair upon a surface of the limiting aperture.

In accordance with yet a further aspect of the present system, there is disclosed a method of capturing stereoscopic images of a subject using a rear-viewing endoscope having an objective lens assembly having first and second lens groups and a complementary multiband bandpass filter (CMBF) pair situated between the first and second lens groups, a limiting aperture, and a camera having a sensor array, the method may include one or more acts of: receiving image rays of the subject by the first lens group; collimating, by the first lens group, the received image rays to form collimated image rays and providing the collimated image rays to the CMBF pair; filtering, by the CMBF pair, the collimated image rays to form corresponding filtered image rays; focusing, by the second lens group, the filtered image rays upon the sensor array of the camera; and sensing, by the sensor of the camera, the focused filtered image rays and forming corresponding stereoscopic image information.

In accordance with the method, the collimated image rays may be provided to the CMBF pair have a minimal angle of incidence (AOI) which is less than or equal to a threshold angle of incidence (TAOI) value. Further, the TAOI value may be 25 degrees. The method may further include an act of controlling, by the limiting aperture, an intensity level of the collimated image rays.

The invention is explained in further detail, and by way of example, with reference to the accompanying drawings wherein:

FIG. 4B is a perspective view of the link pair in a neutral position in accordance with embodiments of the present system;

FIG. 4C is a front view of the link pair in accordance with embodiments of the present system;

FIG. 4D is a top view of the link pair in accordance with embodiments of the present system;

FIG. 4E is an exploded perspective view of the link pair of FIG. 4B in accordance with embodiments of the present system;

FIG. 4F is an exploded front view of the link pair of FIG. 4B in accordance with embodiments of the present system;

FIG. 4G is an exploded side view of the link pair of FIG. 4B in accordance with embodiments of the present system;

FIG. 4H is a side perspective view of the second link in accordance with embodiments of the present system;

FIG. 4I is a plan view of the second link 411B taken along lines 4I-4I of FIG. 4F in accordance with embodiments of the present system;

FIG. 4J is a bottom view of the link pair 411 in accordance with embodiments of the present system;

FIG. 4K is a front view of yet another link pair in accordance with embodiments of the present system;

FIG. 5A is an exploded perspective view of a link pair in accordance with embodiments of the present system;

FIG. 5B is an exploded front view of the link pair of FIG. 5A in accordance with embodiments of the present system;

FIG. 5C is an exploded side view of the link pair of FIG. 5A in accordance with embodiments of the present system;

FIG. 13A is a light ray trace of a lens array having an 80 degree FOV in accordance with embodiments of the present system;

FIG. 13C is a screenshot of graph of relative illumination vs. Y field for the lens array having an 80 degree FOV;

Figure 20:
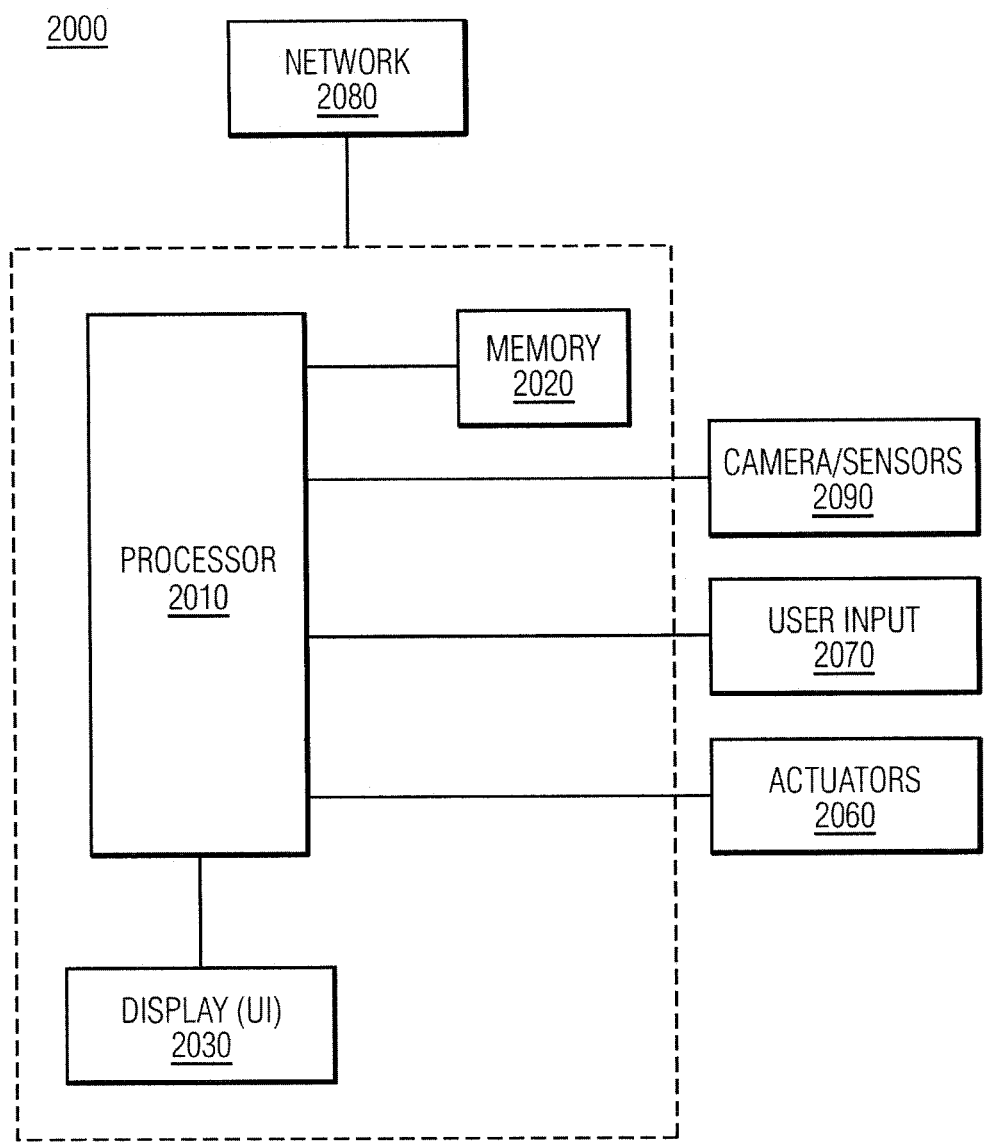

FIGS. 14A, 15A, 16A, 17A, 18A, and 19A show light ray traces of 100, 120, 130, 140, 150, and/or 160 degree FOV lenses, respectively, in accordance with embodiments of the present system;

FIGS. 14B, 15B, 16B, and 17B, 18B, and 19B show graphs of relative illumination vs. Y field for 100, 120, 130, 140, 150, and/or 160 degree FOV lenses, respectively, in accordance with embodiments of the present;

FIGS. 14C, 15C, 16C, 17C, 18C, and 19C shown graphs of relative illumination vs. Y field for 100, 120, 130, 140, 150, and/or 160 degree FOV lenses, respectively, in accordance with embodiments of the present system;

FIG. 20 shows a portion of a system in accordance with an embodiment of the present system; and FIG. 21 shows a portion of code used to control actuators to position the imaging unit.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number. Moreover, for the purpose of clarity, detailed descriptions of certain features will not be discussed when they would be apparent to those with skill in the art so as not to obscure the description of the present system.

In one embodiment, there is provided system, apparatus, device, and/or method for systematically viewing a surgical field which may include an organ using a rear viewing endoscope so as to standardize endoscopy procedures which may reduce surgical time. Accordingly, medical costs and operating time may be reduced, and quality of care may be enhanced.

Figure 1:
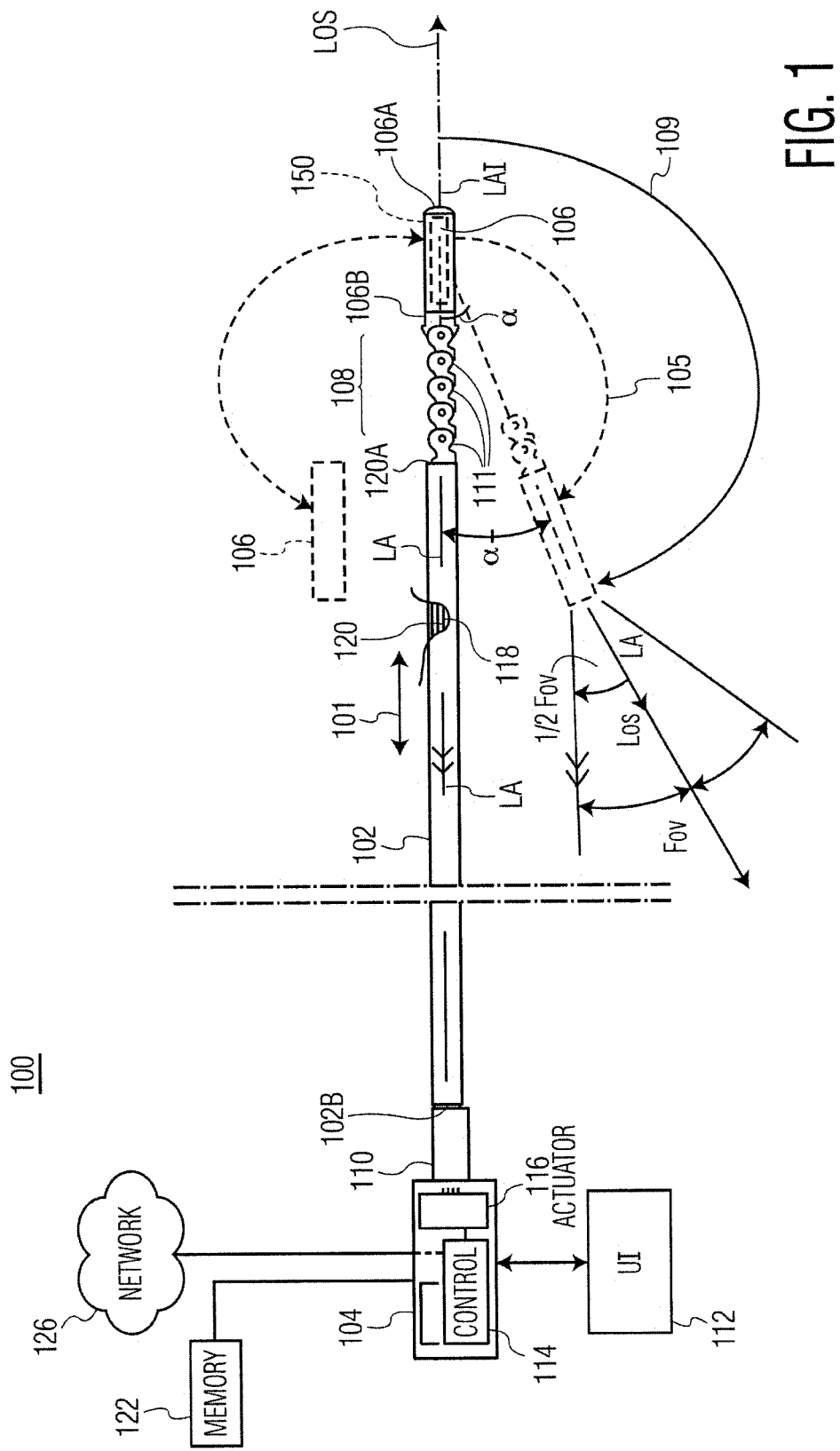
FIG. 1 shows a side view of an endoscope in accordance with embodiments of the present system.

A side view of an endoscope 100 in accordance with embodiments of the present is shown in FIG. 1. An elongated section (or barrel section) 102 has a proximal end 102B and a distal end 102A and a cavity 118 situated therebetween. The elongated section 102 may define a longitudinal axis (LA). The proximal end 102B of the elongated section 102 is coupled to control portion, such as including an actuation unit 104, via a mechanical coupling 110 and the distal end 102A is coupled to a flexible portion 108. The flexible portion 108 includes a plurality of links 111 coupled in a serial manner. An imaging unit 106 has proximal and distal ends 106B and 106A, respectively, the former of which is coupled to the elongated section 102 via the flexible portion 108. The imaging unit 106 includes a cavity in which an image capture device 150 such as a still or video camera situated. The imaging unit 106 has a longitudinal axis (LAI) which, for the sake of clarity, may correspond with a line of site (LOS) of the image capture device 106. However, it yet other embodiments, it is envisioned that the LOS may change relative to the LAI or differ from the LAI. The imaging unit 106 may rotate (e.g., see, arrow 109) about one or more axis relative to the elongated section 102 to provide a rear viewing image as illustrated by arrow 109. Accordingly, an angle (alpha) formed by the intersection of the LOS and the LA (in one or more planes) may have a range of substantially 0 through +/−180 degrees. However, other ranges are also envisioned such as 0 through +/−140 degrees or, for example, 0 through +/−half of a field of view (FOV) of the image capture device 106 as will be discussed elsewhere, where the FOV of the image capture device 106 is 90 degrees, for example, and thus providing a rear view parallel to the longitudinal axis (LA) elongated section 102.

The proximal end 102B of the elongated section 102 is coupled to the control portion 104 via the mechanical coupling 110. The mechanical coupling 110 is configured to be coupled to a positioning linkage and/or a user interface device 112 such as an arm, a handle, joystick, mouse, keyboard, touch pad or display, and/or any other user interface device, where the position of the positioning linkage may be controlled by the system and/or user using the user interface device 112. Accordingly, the mechanical coupling may include one or more surfaces and/or threaded areas suitable for coupling to the positioning linkage. Accordingly, for example, in certain embodiments, the linkage may be coupled to a robotic arm which may be remotely controlled by the system and/or user via any of the user interface devices 112 noted above and the like. However, in yet other embodiments, it is envisioned that the linkage may be manually manipulated and/or controlled by a user, such as also via any of the user interface devices 112. Although the mechanical coupling 110 is situated between the elongated section 102 and the control portion 104, in yet other embodiments it is envisioned that the elongated section 102 is situated between (and coupled each of) the control portion 104 and the mechanical coupling 110.

A controller 114 may control the overall operation of the endoscope 100 and may be located within the control portion 104 or may be situated elsewhere in whole or in part. The controller 114 may include one or more processors such as microprocessors or other logic devices which may me locally or remotely situated relative to each other. The controller 114 may be coupled to an actuator 116, the image capture device 150, a memory 122, a network 126, and/or to a user interface (UI) 112 via a wired and/or wireless (transmission/reception (Tx/Rx)) connection. Accordingly, one or more of the controller 114, the actuator 116, the image capture device 150, the memory 122, the network 126, and/or to a user interface (UI) 112 may include a transmitter and/or receiver. The UI 112 may include one or more of a rendering device such as a display, a speaker, a haptic device, etc., to render information such as positioning information, setting information, sensor information, image information (e.g., content, etc.), positioning information (e.g., for reporting positions of one or more portions of the endoscope 100) for the convenience of the user. Moreover, the UI 112 may include a user input device such as a mouse, a touchpad, a joystick, a keyboard, a touch-screen, etc. The network 126 may include any suitable network such as a proprietary network, a local area network (LAN), a wide area network (WAN), the Internet, an intranet, a local bus, etc. The controller 114 may receive information from the memory 122 and may store information (e.g., image information, etc.) therein.

The plurality of links 111 (e.g., comprising first and second links forming a link pair) may be flexibly coupled to each other using any suitable method such as one or more pins, a flexible coupling (e.g., a live hinge), etc. Movement of one or more of the links 111 relative to each other may be controlled using control wires 120, such as made of stainless steel, which are attached to at least one corresponding link 111 of the plurality of links 111 and the actuator 116. The actuator 116 may include one or more actuators (e.g., solenoids, motors, electronic control circuitry, drivers, etc.) to control a tension and/or position of each of the control wires 120 under the control of the controller 114. For example, if the tensioning members are shape memory alloy (SMA) wires, the actuator may include an SMA control system which may receive control signals from the controller 114 and output a corresponding current and/or voltage to control a length and/or tension of one or more corresponding SMA wires. A longitudinal length of the elongated section 102 may be set so that control lines having a sufficient length for a desired amount of stretch may be placed within the cavity 118 of the elongated section 102 without folding the control wires. When heated, the control wires may contract a known amount $\Delta_{sma}$ which, when using Flexinol™ as a control wire material has been found to be about 3% of its total length ($L_{sma}$) when heated to maximum temperature levels, which are within operating limits of the present system. Further, assuming a link requires a control wire to travel a distance $D_{cont}$ for full deflection of the link about its hinge axis (HA) (e.g., from 0 degrees to full deflection), then a relationship between the $\Delta_{sma}$, $L_{sma}$, and $D_{cont}$ may be defined using equation 1 below.

$$L_{sma} * \Delta_{sma} = D_{cont} \qquad \text{Eq. (1)}$$

Thus, assuming a link requires $D_{cont}$=3 mm and $\Delta_{sma}$=3%, then the $L_{sma}$ should be set to 100 mm. Thus, a length of the elongated section 102 may be set so that this desired length of SMA may be used. However, if a shorter length of the elongated section is preferred, the SMA may be folded by, for example, wrapped it around one or more tensioning pulleys. Further, the SMA may be coiled to increase a shrinkage rate per linear length. It has been found that an angle (deflection) to force ratio may be substantially linear. Accordingly, angles and/or forces may be easily determined using linear mathematical methods by, for example, a controller of the system. The control wires 120 may run through the cavity 118 of the elongated section 102. A loop or a sheath may be situated about at least a portion of one or more control wires 120 to route the control wire, insulate the control wire, and/or reduce friction between the control wire and adjacent components. Each control wire 120 may include a shape memory allow (SMA) portion 221 having a known resistance $R_{SMA}$. (e.g., see, FIG. 2).

Figure 2:
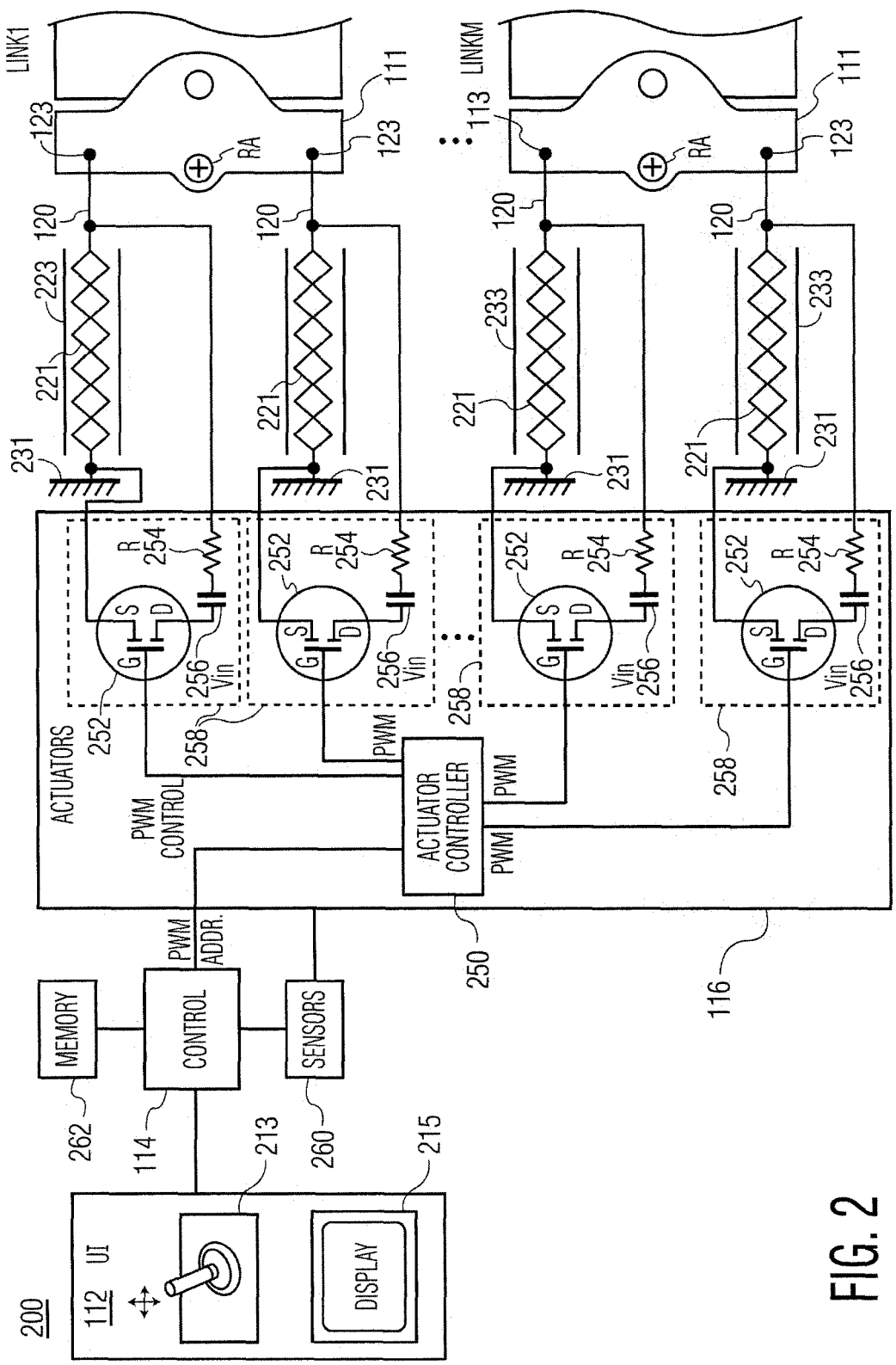
FIG. 2 is a schematic block diagram of the endoscope shown in FIG. 1 in accordance with embodiments of the present system.

FIG. 2 is a schematic block diagram 200 of the endoscope 100 shown in FIG. 1 in accordance with embodiments of the present system. The actuators 116 may include a plurality of drivers 258 each including a switch 252, a power source Vin, and a limiting resistor R coupled in series with each other. An actuator controller 250 may be coupled to the controller 114 and to each of the drivers 258. Accordingly, the actuator controller 250 may process signals received from the controller 114 and output corresponding control signals (e.g., Pulse Width Modulation (PWM) signals) to control corresponding drivers 258 in accordance with the signals received from the controller 114. The PWM control signals may be coupled to a switch (e.g., a gate G) of a corresponding driver 258 of the drivers 258 so as to control power output by the corresponding driver 258 of the drivers 258. The signals received from the controller 114 may include address information which may identify a corresponding driver 258 of the drivers 258 to control. Accordingly, the actuator controller 250 may include an addressable device (e.g., a multiplexor (MUX)) to select a driver 258 of the drivers 258 to control. Sensors 260 may be provided and may include for example, temperature sensors, position sensors (e.g., rotational position sensors, orientation sensors, etc.), pressure sensors, current/voltage sensors, etc. The sensors 260 may provide corresponding sensor information such as feedback (FDBK) information (e.g. current/voltage feedback) to one or more of the controller 114 and the actuators 116. The FDBK information (e.g., current feedback information of the feedback information) may be processed by the controller 114 to adjust a current and/or voltage to be imposed across a corresponding the SMA 221.

Outputs of each of the drivers 258 (e.g., via source S or drain D) are correspondingly electrically coupled across at least a portion of an SMA 221 of a corresponding control wire 120. Each control wire 120 is coupled to an anchor 231 to prevent movement of the corresponding control wire 120 and to a corresponding link 111, at connections 123 such that each link 111 includes pair of control wires 120. When a tension of a control wire 111 is increased, it causes rotation of a link 111 about its rotational axis (RA). The SMA portion 221 of each control wire 111 may be heated to cause it to shorten in length and, thus, increase tension. To heat the SMA portion 221, a corresponding driver 258 may apply a current or voltage across the SMA 221 coupled thereto. As methods to control SMA wires are known in the art, a further description thereof will not be given.

However, in yet other embodiments, it is envisioned that other actuation methods may be used. For example, a motor/pulley, a cable driven system, a manual system, a gear driven rotation system, linear actuators, solenoids, magnetic systems, etc., may be used. The controller 114 may receive user inputs via a user input device such as a joystick 213, process the user inputs, and control the actuators 258 to output power accordingly. The image capture device 150 may transmit content to the controller 114 and the controller 114 may render the content on a UI of the system such as a display 213 for the convenience of the user. Further, the controller 114 may store the content and/or other information (e.g., settings, parameters, time, metadata, etc.) on a memory of the system such as memory 262 for later use.

The image capture device 150 may include any suitable device for capturing video and/or still images and/or transmitting these captured images using wired and/or wireless methods. Accordingly, the image capture device 150 may, include for example, one or more of a controller, a complementary metal-oxide semiconductor (CMOS) array, a charge-coupled device (CCD) array, one or more optical elements, a power source, a transmitter. The one or more optical elements may include lenses, prisms, mirrors, and CMBF as described in US 2011/0115882, which is incorporated herein by reference in its entirety, and other optical elements as needed. In one embodiment, it is envisioned that the image acquisition device may include, for example, a focal plane array such as a Thin Observation Module by Bound Optics (TOMBO) imaging system as is known in the art. In yet other embodiments, it is envisioned that the image acquisition device may include an encapsulated real-time wireless imaging apparatus. In yet other embodiments, it is envisioned that the image acquisition device may include, for example, a digital imaging camera such as, for example, CMOS and/or CCD detectors. However, regardless of the type of image acquisition device that is used, the device should be configured and arranged such that the images corresponding with a rear view (e.g., corresponding with a rearward field of view) of a surgical field may be obtained when desired. Although a wireless image acquisition device is described, it is also envisioned that the image acquisition device may include a wired transmission system which may transmit acquired images using an electrical connection and/or a fiber-optic link.

With regard to the flexible portion 108, this portion includes a plurality of links 111 coupled in a serial manner to each other in a modular fashion. Each coupled link pair may have a range of motion (RoM) which may be set by the user and/or system. For example, some coupled link pairs may have a RoM of +/−60 degrees while others may have a range of +/10 degrees. Further, in yet other embodiments, an asymmetrical RoM may be employed. For example, a RoM of +180 through −20 degrees, or 0 degrees (e.g., from the longitudinal axis (LA) of the elongated section 102) through a maximum degree threshold which is about 180 degrees or less. Thus, the RoM of a link pair may vary. Further, link pairs may be mixed and/or matched. For example, by combining a link from a 90 degree RoM link pair with a link from a 45 degree RoM link pair may yield a link pair having a RoM of (490+45)/2=67.5 degree RoM link pair. Further, a desired RoM may be obtained by adding link pairs serially to each other. For example, three link pairs each having a RoM of +−45 degrees may serially attached to each other to obtain a +/−135 degree RoM. This is more clearly illustrated in with reference to FIGS. 3A through 3E which illustrate embodiments of the flexible portions 308A-308C in accordance with embodiments of the present system.

FIG. 21 shows program code for controlling an actuator in accordance with embodiments of the present system.

Figure 3A:
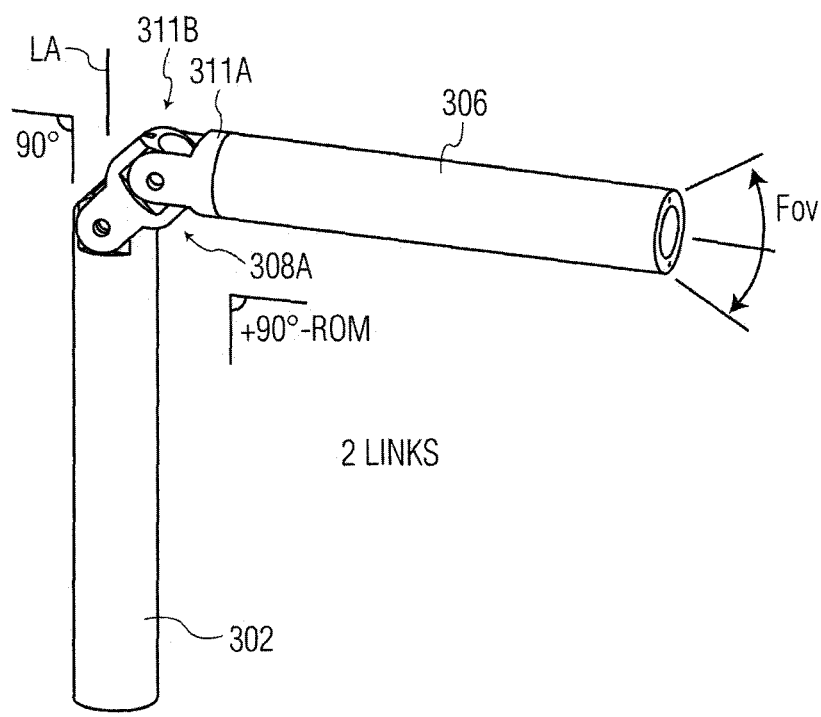
FIG. 3A is a side view of a portion of an endoscope in accordance with embodiments of the present system.
Figure 3B:
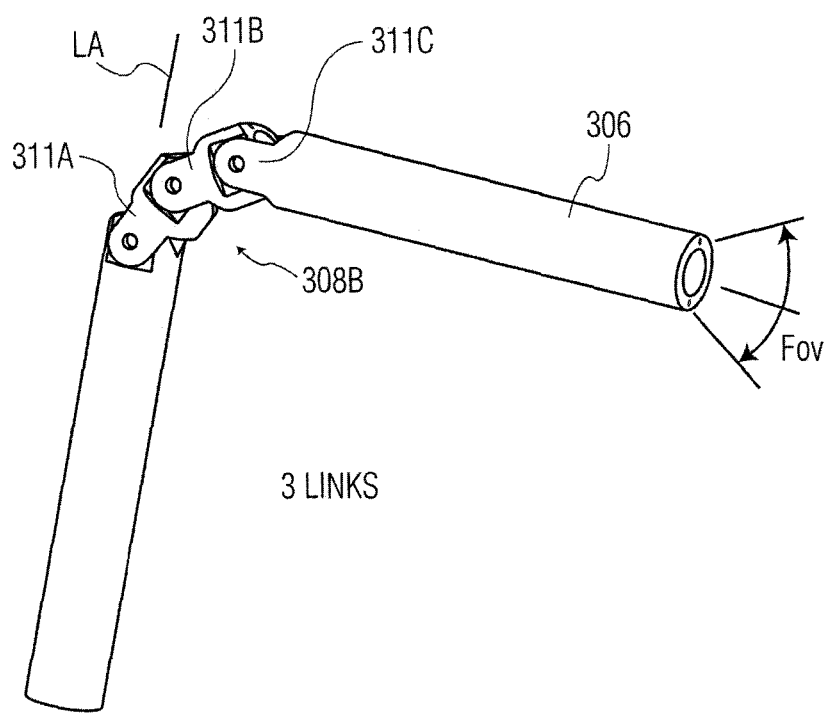
FIG. 3B is a side view of a portion of an endoscope in accordance with embodiments of the present system.
Figure 3E:
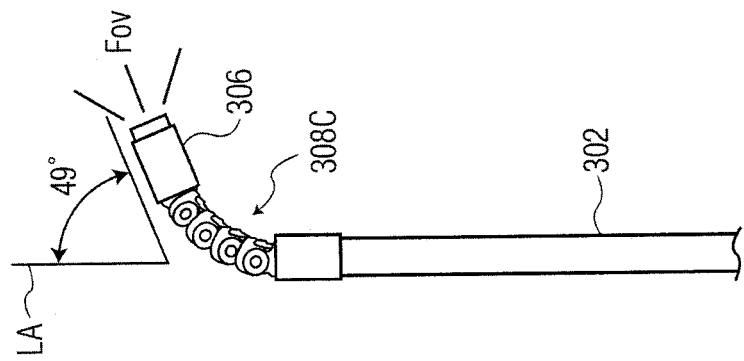
FIG. 3E is another side view of a portion of the endoscope shown in FIG. 3C in accordance with embodiments of the present system.
Figure 3D:
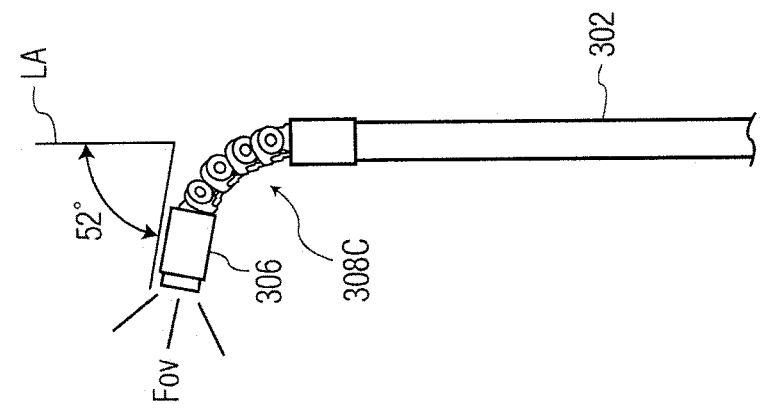
FIG. 3D is a side view of a portion of the endoscope shown in FIG. 3C in accordance with embodiments of the present system.
Figure 3C:
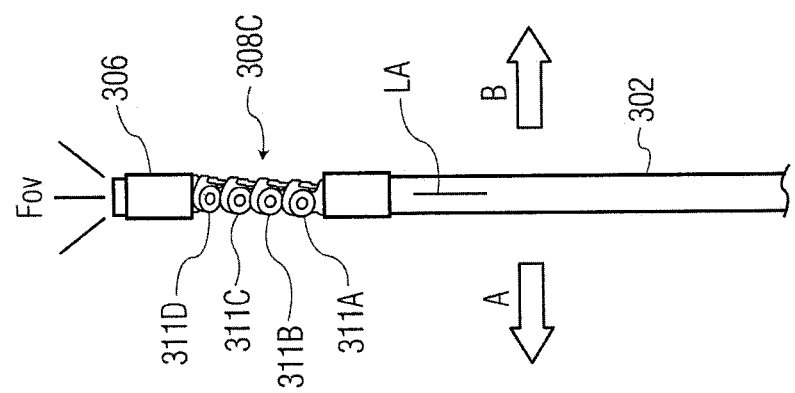
FIG. 3C is a side view of a portion of an endoscope in accordance with embodiments of the present system.

Referring to FIGS. 3A through 3C, flexible portions 308A through 308C, respectively, couple an elongated section 302 to a distal portion 306. The elongated section 302 is similar to the elongated section 102 and the distal portion 306 is similar to the distal portion 106. However, the flexible portions 308A through 308C, of FIGS. 3A through 3E, respectively, include modular links 311A through 311C, respectively, each having different RoM. Further, the flexible portions 308A through 308C may each have a different number of links 311. For example, with reference to FIG. 3A the flexible portion 308A may provide total symmetric RoM of +/−90 degrees (e.g., of the distal portion 306 relative to the elongated section 302) using two links 311A (each being substantially similar to the links 111 of FIG. 1) each having a RoM of about +/−45 degrees. Similarly, with reference to FIG. 3B the flexible portion 308B may provide a similar total RoM of +/−90 degrees using three links 311B each having a RoM of about +/−30 degrees. Moreover, with reference to FIGS. 3C through 3E the flexible portion 308C may provide a total asymmetric RoM of between +52 degrees (see, FIG. 3D) and −49 degrees (see, FIG. 3E) using four links 311C each having a RoM of between (52 degrees/4 degrees/link)=+13.0 degrees and −(49/4)=−12.25 degrees. FIG. 3C illustrates a neutral position in which the longitudinal axis (LA) of the distal portion 306 relative to the elongated section 302 is about 0 degrees, providing a front field of view (FOV) which may be a desired position for insertion into a volume of interest (VOI). Thus, assuming a flexible portion is formed using one or more links(i) with a total of N links, the total RoM of flexible portion may be expressed using equation 2 below.

$$RoM_{Total} = \sum_{i=1}^{N} Rom_i \qquad \text{Eq. (2)}$$

Figure 4A:
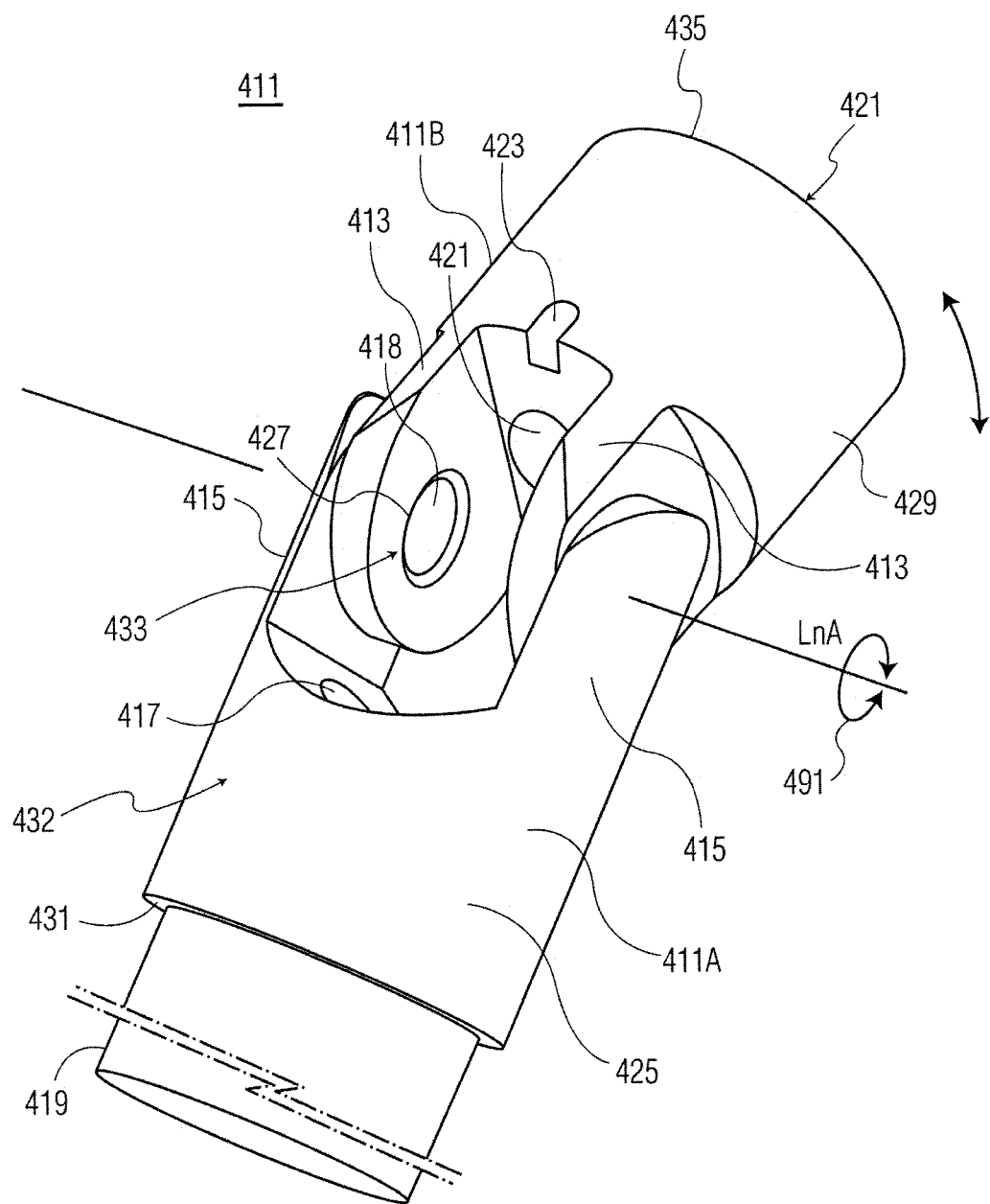
FIG. 4A is a perspective view of a link pair in accordance with embodiments of the present system.

A perspective view of a link pair 411 in accordance with embodiments of the present system is shown in FIG. 4A. The link pair 411 is formed from first and second links 411A and 411B, respectively, which are coupled to each other so as to rotate about a link axis LnA as illustrated by arrow 491. The first link 411A has proximal and distal ends 431 and 432, respectively, and a body 425 through which one or more openings 417 pass. The one or more openings 417 may be configured to provide for the passage of video conduits (e.g., a fiber optic video line, etc.), power lines, and/or control lines to pass therethrough. Flanges 415 extend from the body 425 and each include a hinge pin 418 extending therefrom. The body 425 may include a mounting lug 419 at the proximal end 431.

The second link 411B has a body 429 through which one or more openings 421 pass and proximal and distal ends 433 and 435, respectively. The opening 421 is configured to provide for the passage of video conduits (e.g., a fiber optic video line, etc.), power lines, and/or control lines to pass therethrough. Flanges 413 extend from the body 429 and each includes an opening 427 configured to receive the hinge pin 418 so as to be coupled to the first link 411A and to form a hinge. A distal end 435 of the body 429 includes an opening 421 configured to receive a mounting lug such as the mounting lug 419 or a mounting lug of an elongated section or distal portion. The mounting lug 419 may be configured to be coupled to an opening 421 of an adjacent link 411B or an opening of an elongated section or distal portion (e.g., using a friction fit, threaded mount, adhesives, etc.). The first and/or the second link 411A, 411B may include an attachment portion 423 configured to fixedly attach one or more control lines. A location of the attachment portion 423 may be adjusted so as to obtain full rotation when a control line attached to the attachment portion 423 is fully tensioned.

Another perspective view of the link pair 411 in a neutral position in accordance with embodiments of the present system is shown in FIG. 4B. In the neutral position, the first and second links 411A and 411B are rotated about 0 degrees relative to each other about their corresponding link axes LnA and may be considered to be substantially aligned with each other about the link axes LnA.

A front view of the link pair 411 in accordance with embodiments of the present system is shown in FIG. 4C.

A top view of the link pair 411 in accordance with embodiments of the present system is shown in FIG. 4D.

An exploded perspective view of the link pair 411 of FIG. 4B in accordance with embodiments of the present system is shown in FIG. 4E. The second link is shown rotated about 90 about its longitudinal axis LLA for sake of illustration.

An exploded front view of the link pair 411 of FIG. 4B in accordance with embodiments of the present system is shown in FIG. 4F.

An exploded side view of the link pair 411 of FIG. 4B in accordance with embodiments of the present system is shown in FIG. 4G.

A side perspective view of the second link 411B in accordance with embodiments of the present system is shown in FIG. 4H.

A plan view of the second link 411B taken along lines 4I-4I of FIG. 4F in accordance with embodiments of the present system is shown in FIG. 4I.

A bottom view of the link pair 411 in accordance with embodiments of the present system is shown in FIG. 4J.

A front view of yet another the link pair 411K in accordance with embodiments of the present system is shown in FIG. 4K. The link pair 411K includes first and second links 411AK and 411BK, respectively, which are similar to the first and second links 411A and 411B, respectively, of FIG. 4A. However, the first link 411AK includes a single center flange 415K rather than two flanges 415 of the first link 411A. Further, the second link 411BK includes flanges 413K configured to fit about and engage the single center flange 415K as opposed to being situated between flanges 415 of the link pair 411.

An exploded perspective view of a link pair 511 in accordance with embodiments of the present system is shown in FIG. 5A. The link pair 511 includes first and second links 511A and 511B, respectively. The first link 511A is similar to the first link 411A of FIG. 4A. Accordingly, similar reference numerals are used. The second link 511B is similar to the second link 411 and, thus, includes a center opening 421 and flanges 413 extending from a body 529. However, unlike the second link 411, the second link 511 includes a second pair of flanges 515 extending from the body 529. The flanges 515 are similar to the flanges 415 of the first link 411A of FIG. 4A and are configured to receive flanges, such as flanges 413 of an adjacent second link 411B. Accordingly, the second link 511B may be considered a hybrid link comprising a first link (e.g., 411A) and a second link (411B) formed integrally with each other. Further, the second link 511B is shown rotated about 90 about its longitudinal axis LLA for sake of illustration.

The links 411 and 511 may include stops which may limit travel of the first and second links (e.g., 411A and 411B or 511A and 511B) relative to each other once the first and second links are rotated to an extreme position relative to each other about their link axis LnA shown in FIG. 4A (e.g., +/−35, 45, 90, etc. degrees). The stops may be configured to provide symmetrical rotation (e.g., +/−90 degrees of travel), or asymmetrical travel (e.g., 0 through 90 degrees travel) of the first and second links relative to each other about their link axis LnA. Although certain ranges are shown, other ranges are envisioned.

An exploded front view of the link pair 511 of FIG. 5A in accordance with embodiments of the present system is shown in FIG. 5B.

An exploded side view of the link pair 511 of FIG. 5A in accordance with embodiments of the present system is shown in FIG. 5C.

For the sake of clarity, it will be assumed that a link pair comprises first and second links coupled to each other and rotating about a single link axis LnA relative to each other.

Figure 6:
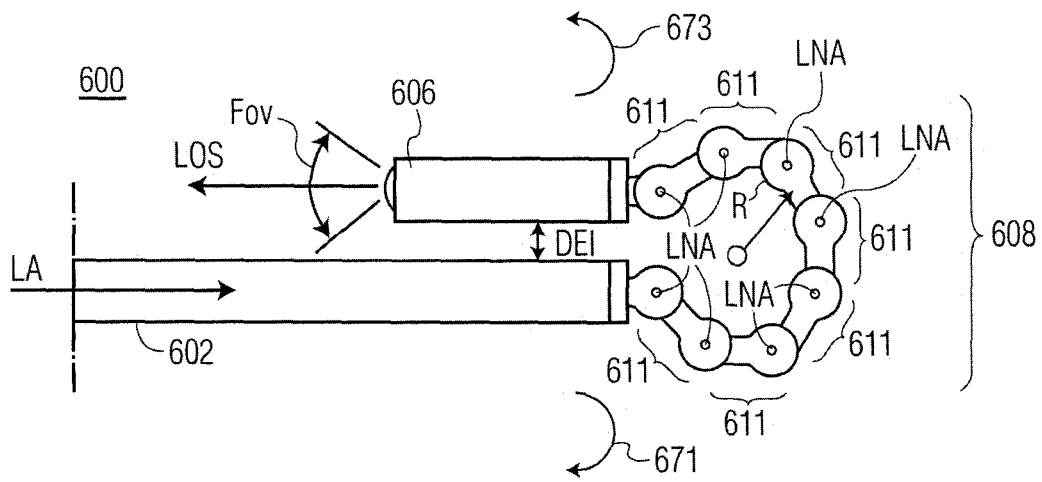
FIG. 6 is a side view of a portion of an endoscope in accordance with embodiments of the present system.

FIG. 6 is a side view of a portion of an endoscope 600 in accordance with embodiments of the present system. The endoscope 600 is similar to the endoscope 100 and includes an elongated section 602 and an imaging unit 606 coupled to the elongated section 602 by a flexible portion 608. The elongated section 602 and the imaging unit 606 are similar to the elongated section 102 and the imaging unit 106, respectively. However, the flexible portion 608 includes 8 link pairs rather than 5 link pairs of the endoscope 100. Further, the imaging unit 606 is shown substantially rotated about 180 degrees with its line-of-site (LOS) substantially parallel to a longitudinal axis of the elongated section 602. For the sake of clarity, it will be assumed that the LOS of the imaging unit 602 and a longitudinal axis of the imaging unit 606 are substantially aligned with each other. A controller may control certain links to rotate in a positive direction about their corresponding link axis (LnA) as shown by arrow 671 and may control other links to rotate in a negative direction about their corresponding link axis (LnA) as shown by arrow 673. Accordingly, a distance (DEI) between the elongated section 602 and the imaging unit 606 when the imaging unit 606 is rotated towards the elongated section (e.g., 180 degrees as shown) may be reduced. Further, it is envisioned that the controller may control certain link pairs to remain rotationally stationary, if desired.

Figure 7:
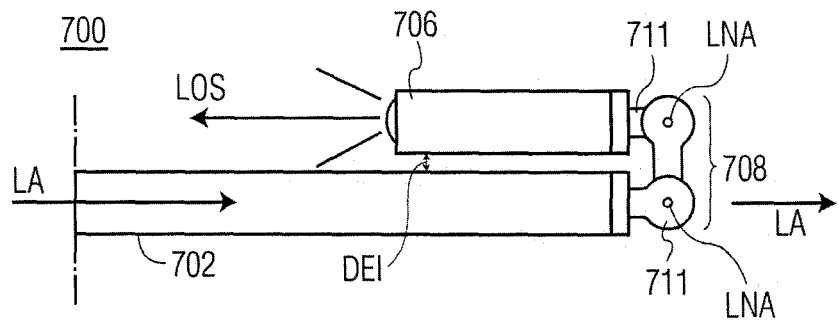
FIG. 7 is a side view of a portion of an endoscope in accordance with embodiments of the present system.

FIG. 7 is a side view of a portion of an endoscope 700 in accordance with embodiments of the present system. The endoscope 700 is similar to the endoscope 600 and similar numerals are used for the elongated section 602 and the imaging unit 606. However, a flexible portion 708 includes two link pairs 711 as opposed to 8 link pairs of the endoscope 600. Rotation of each of the link pairs 711 may be about their respective axes is equal to about 180 degrees. However, other values and/or ranges are also envisioned.

Thus, an angular rotation of each link pair Lr (degrees) (when each link rotates in the same direction (c.f. 608 and 708) may be determined by diving the total rotation Tr of the imaging unit 706 relative to the elongated unit 702 by the number of link pairs Nlp (e.g., 2 in the present example). Thus, Lr=Tr/Nlp. Accordingly, in the present example, Lr=180/2=90 degrees. In the present example, it will be assumed that each link unit has the same rotation (e.g., positive in the present example) as other link pairs. However, it is also envisioned link pairs may have extreme travel rotations which differ from one another. For example, to obtain the 180 degrees of rotation of the imaging unit relative to the elongated section using two link pairs, a first link pair may rotate 45 degrees about its link axis and the second link pair may rotate 135 degrees. The controller may control rotation of the link pairs and may receive rotational position feedback information from, for example, rotational encoders of each link pair.

As described in connection with FIG. 4A, each link includes a pair of links 411A and 411B. Thus, in the embodiment shown in FIG. 7, the endoscope comprises a rigid section having opposed first and second ends, and a first cavity situated between the first and second ends, the rigid section having a longitudinal length and defining a longitudinal axis; a first link pair comprising first and second link portions coupled to each other and rotating about a first hinge axis; a second link pair coupled serially to the first link pair and comprising third and fourth portions coupled to each other and rotating about a second hinge axis; an imaging section coupled to the second link pair and having a second cavity situated between first and second ends; a camera situated within the cavity of the other cavity; where the plurality of first and second flexible links pairs are configured to rotate the imaging unit at least 90 degrees relative to the longitudinal axis of the rigid section. Further, the second and third link pairs may be formed integrally with each other, and the first and second hinge axes may be substantially parallel to each other. In one embodiment, when an angle of the imaging unit is rotated more than 90 degrees relative to the rigid section, a rotational angle (RA) of the first link pair and an RA of the second link pair is substantially equal to 180 degrees. For example, RA1 may be an angle of rotation of the first and second link portions relative to each other about the first hinge axis, and RA2 may be an angle of rotation of the third and fourth link portions relative to each other about the second hinge axis, where the RA1+RA2=180 degrees. As noted above, these two angles may be the same, namely, 90 degrees, or may be differ from one another where the sum of the two angles is 180 degrees to provide the rear view, where each joint pair rotates about its hinge axis with an angle which is equal to one of the two angles RA1, RA2.

Figure 8:
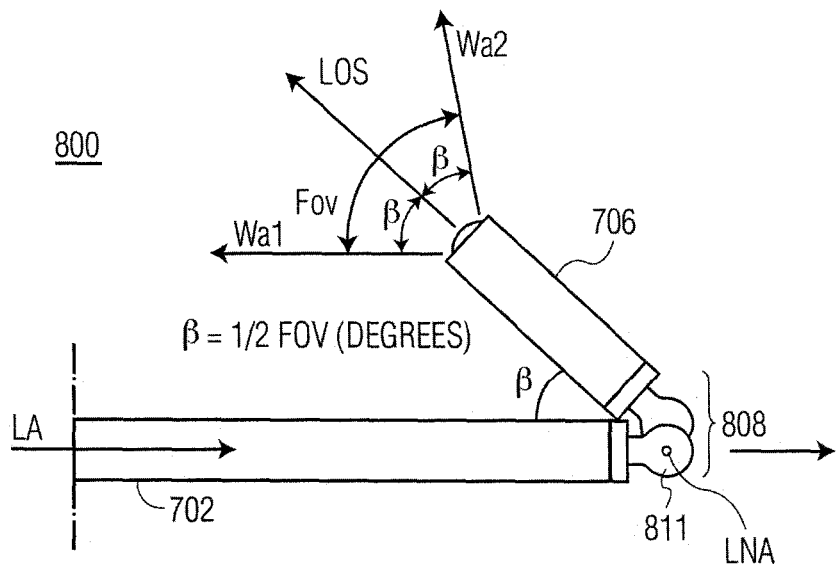
FIG. 8 is a side view of a portion of an endoscope in accordance with embodiments of the present system.

FIG. 8 is a side view of a portion of an endoscope 800 in accordance with embodiments of the present system. The endoscope 800 is similar to the endoscope 600 and similar numerals are used for the elongated section 602 and the imaging unit 606. However, a flexible portion 808 includes a single link pair 811 as opposed to 8 link pairs of the endoscope 600. A field of view (FOV) in degrees corresponds with an angle having walls Wa1 and Wa2 and defines a line of sight (LOS) which corresponds with a center axis of the FOV. When at an extreme position (as shown), the wall Wa1 adjacent to the elongated section 602 is substantially parallel to a longitudinal axis (La) of the elongated section 602. Accordingly, a line of sight of the outer wall Wa1 is along the longitudinal axis of the elongated section 602. Further, an angle of deflection β of the single link pair 811 may be equal to FOV/2 (degrees).

Figure 9A:
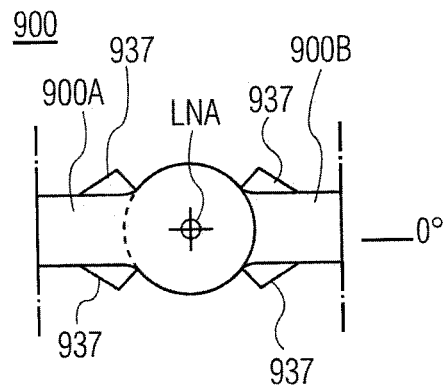
FIG. 9A is a side view of a portion of a link pair according to embodiments of the present system.

A side view of a portion of a link pair 900 according to embodiments of the present system is shown in FIG. 9A. The link pair 900 includes first and second links 900A and 900B, respectively, and is shown in a neutral position. Each of the first and second links 900A and 900B, respectively, include angular limiters ALs 937 which may engage with an adjacent AL 937 of an adjacent link 900A, 900B of the link pair 900 so as to limit angular rotation of the first and second links 900A and 900B, respectively, relative to each other about their link axis to a desired angular rotation and thus, limit rotation of the link pair 900 to a desired rotational value (e.g., +/−90 degrees). Although the ALs 937 are shown on an external portion of the link pair 900, in yet other embodiments, the ALs may be located in other positions such as an internal position of a corresponding link pair.

Figure 9B:
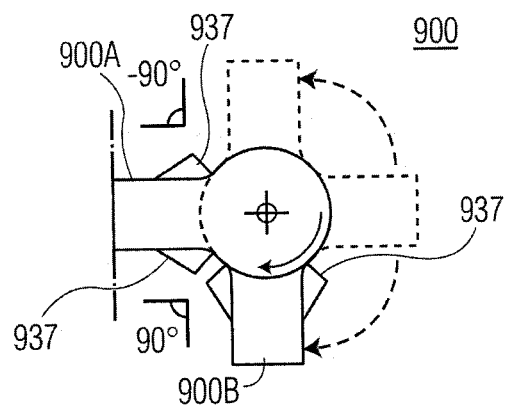
FIG. 9B is a side view of a portion of the link pair rotated 90 degrees according to embodiments of the present system.

A side view of a portion of the link pair 900 rotated 90 degrees according to embodiments of the present system is shown in FIG. 9B. At the extreme travel position (e.g., at + or −90 degrees in the present example), the ALs of the first and second links 900A and 900B, respectively, engage each other and limit further rotation of the of the first and second links 900A and 900B, respectively, relative to each other.

Figure 9C:
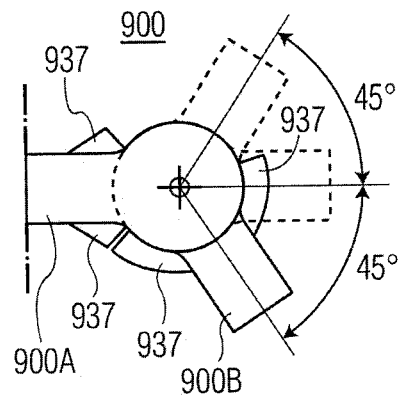
FIG. 9C is a side view of a portion of the link pair rotated 45 degrees according to embodiments of the present system.

A side view of a portion of the link pair 900C rotated 45 degrees according to embodiments of the present system is shown in FIG. 9C. The link pair 900C is similar to the link pair 900. However, the ALs are configured to limit rotation of the link pair to 45 degrees.

Figure 10A:
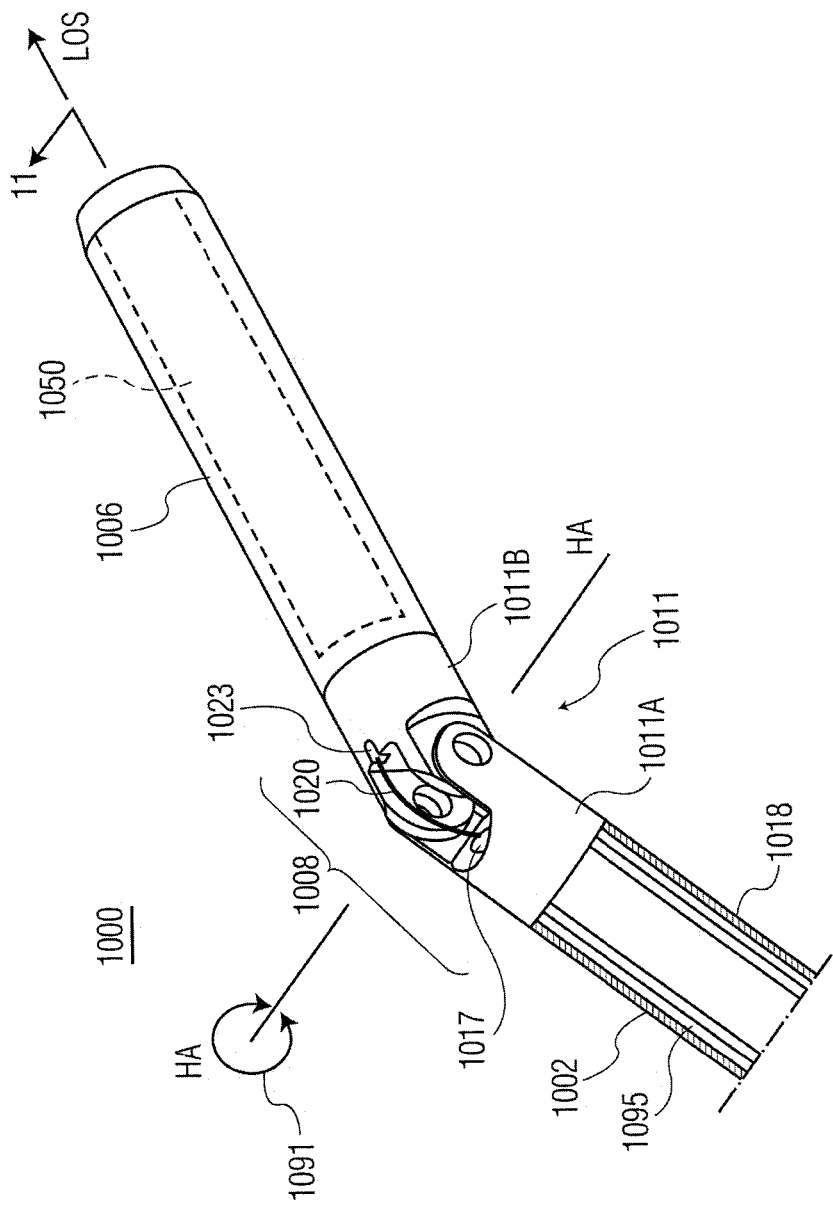
FIG. 10A is a partially cutaway perspective view of a portion of an endoscope 1000 according to an embodiment of the present system.

A partially cutaway perspective view of a portion of an endoscope 1000 according to an embodiment of the present system is shown in FIG. 10A. An elongated section 1002 is coupled to a flexible portion 1008 having a single link 1011. An imaging unit 1006 is coupled to the flexible portion 1008. The elongated section 1002, the flexible portion 1008, and the imaging unit 1006 are similar to the elongated section 102, the flexible portion 108, and the imaging unit 106, respectively, of FIG. 1. However, the flexible portion 1008 has fewer links 1011 than a number of links 111 of the flexible portion 108. The link 1011 may include first and second links 1011A and 1011B, respectively, so as to form a link pair. The first link 1011A may include one or more openings 1017 at least one of which is configured for passage of a control cable 1020. An end of the control cable 1020 is coupled to a cable attachment 1023 of the second link 1011B of the link 1011 so as to transfer a force to the second link 1011B when the control cable 1020 is tensioned. The imaging unit 1006 may include an image capture device 1050 which may include a still or video camera. In some embodiments, the image capture device 1050 may include a commercial off the shelf (COTS) camera. The flexible portion 108 may rotate about one or more axes such as a hinge axis (HA) of the link 1011 as illustrated by arrow 1091 such that the image capture device 1050 may have a desired RoM.

Figure 10B:
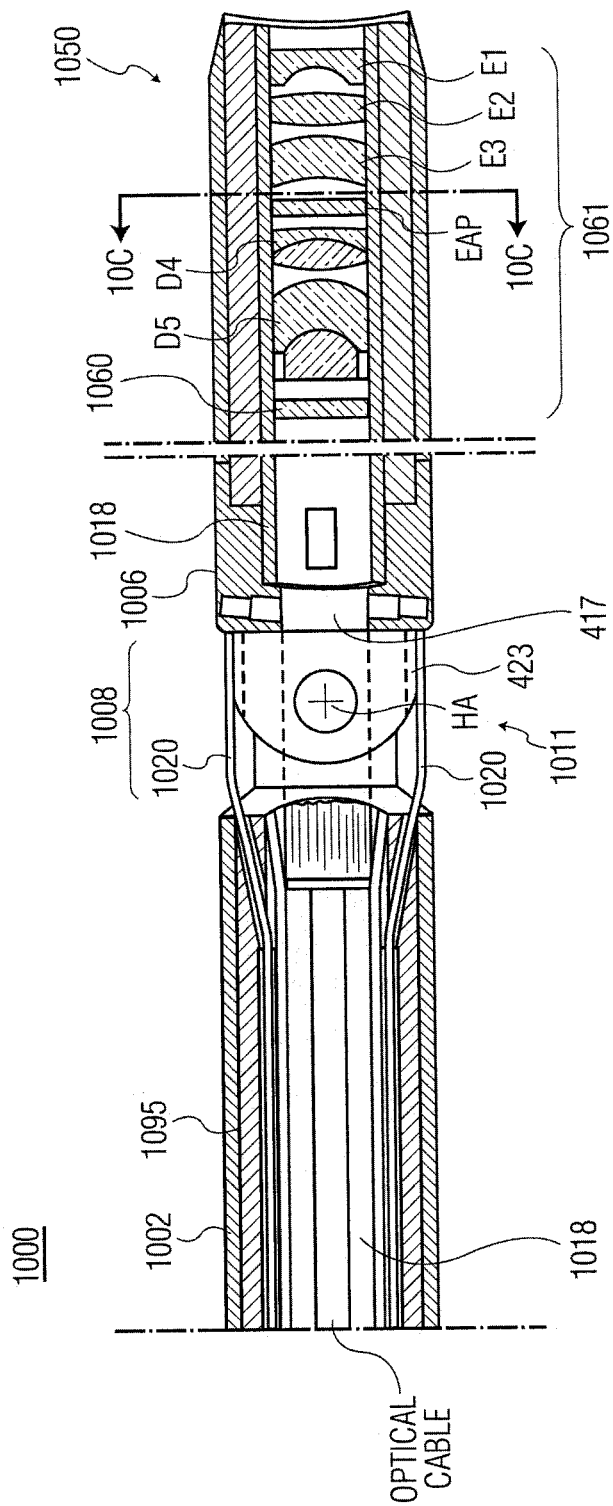
FIG. 10B is a cutaway side view of a portion of the endoscope according to embodiments of the present system.

A cutaway side view of a portion of the endoscope 1000 according to embodiments of the present system is shown in FIG. 10B. The elongated section 1002 may include a cavity 1018 through which cable guides 1095 pass. The one or more portions of the control cables 1020 may pass within the cable guides 1095. The cable guides may include an insulator to electronically and thermally insulate the control cables 1020. The image capture device 1050 may include a sensor 1060 to sense an image displayed thereon. The sensor 1060 may include any suitable sensor array such as a CMOS, a CCD, etc. A lens array 1061 may include one or more lenses and/or other optics elements such as apertures, filters, etc., and may be configured to render an image on the sensor 1060. As shown in FIG. 10B (and FIG. 12), the optical lenses and elements are serially connected back to back sharing a central axis and having a same diameter, such as slightly less than 4 mm, so at to fit within the 4 mm outer housing of the image capture device 1050.

Figure 10C:
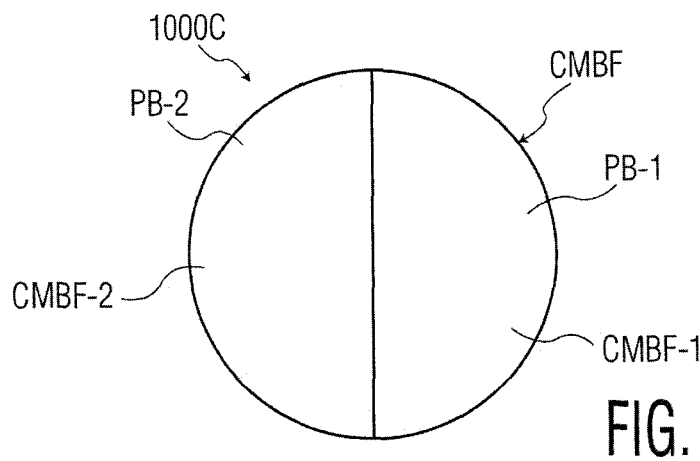
FIG. 10C is a front view of a CMBF pair of the endoscope taken along lines 10C-10C according to an embodiment of the present system.

A front view of a CMBF pair of the endoscope 1000 taken along lines 10C-10C according to an embodiment of the present system is shown in FIG. 10C. The CMBF pair 1000C may have a circular of the like shape and may include two or more CMBF filters such as a first CMBF CMBF-1 and a second CMBF CMBF-2 each of which forms a semicircular shape has an area which is about ½ of the area of the CMBF pair. However, other shapes and/or sizes are also envisioned. Each filter of the CMBF pair (i.e., CMBF-1 and CMBF-2 of the present example) may have complementary passbands. For example, the CMBF-1 has a first passband PB-1 which is complementary to a second passband PB-2 of the CMBF-2, as shown in FIG. 10E, and further described in US2011/0115882, which is incorporated herein by reference in its entirety.

Figure 10D:
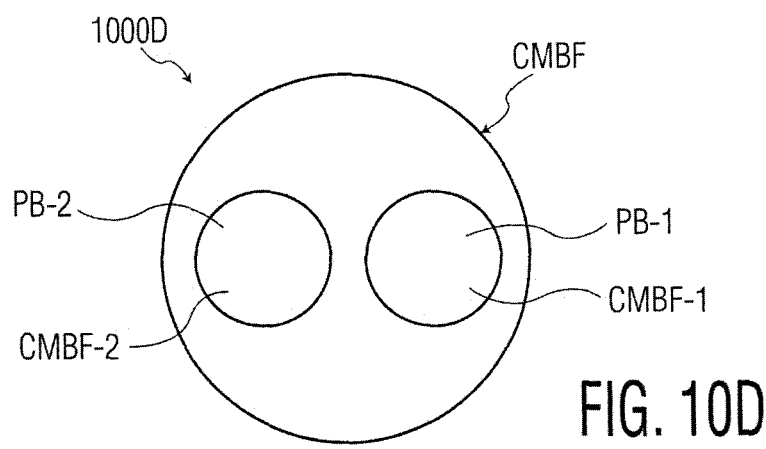
FIG. 10D is a front view of another CMBF pair according to embodiments of the present system.
Figure 10E:
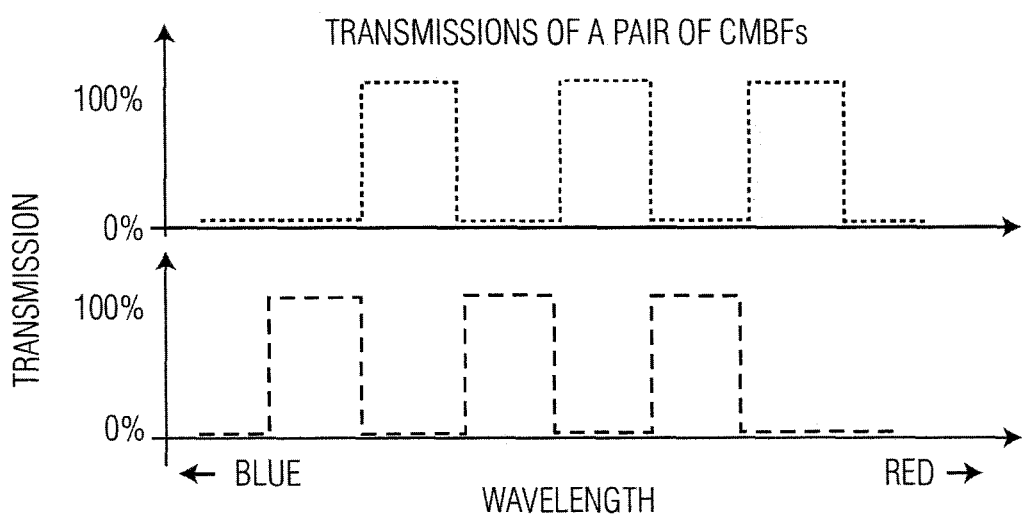
FIG. 10E is a spectral plot of light transmission by an ideal complementary triple-band bandpass CMBF pair in accordance with embodiments of the present system.

FIG. 10D is a front view of another CMBF pair 1000D according to embodiments of the present system. The CMBF pair 1000D includes a first CMBF CMBF-1 and a second CMBF CMBF-2 which have complementary passbands and are circular in shape and equal in size. However, in yet other embodiments, the shape and/or size of the areas of the CMBFs may be the same as or different from each other FIG. 10E is a spectral plot of light transmission by an ideal complementary triple-band bandpass CMBF pair in accordance with embodiments of the present system. It is further envisioned that the CMBFs may include any number of passbands, such as 4 passbands or more than 2 passbands.

Figure 11:
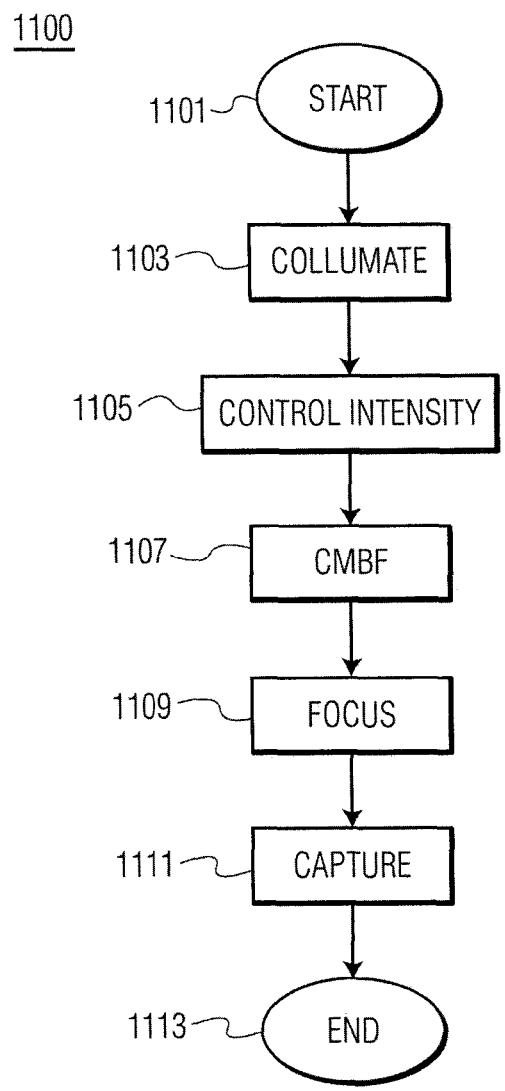
FIG. 11 shows a flow diagram that illustrates a process performed on an endoscope system in accordance with embodiments of the present system.

FIG. 11 shows a flow diagram that illustrates a process 1100 performed on an endoscope system in accordance with embodiments of the present system. The process 1100 may be performed using one or more computers communicating over a network and ma obtain information and/or store information using one or more memories which may be local and/or remote from each other. The process 1100 can include one of more of the following acts. Further, one or more of these acts may be combined and/or separated into sub-acts, if desired. The process 1100 may start during act 1100 and may then proceed to act 1103 and will be explained below after the description of FIGS. 12 and 13A-13C.

Figure 12:
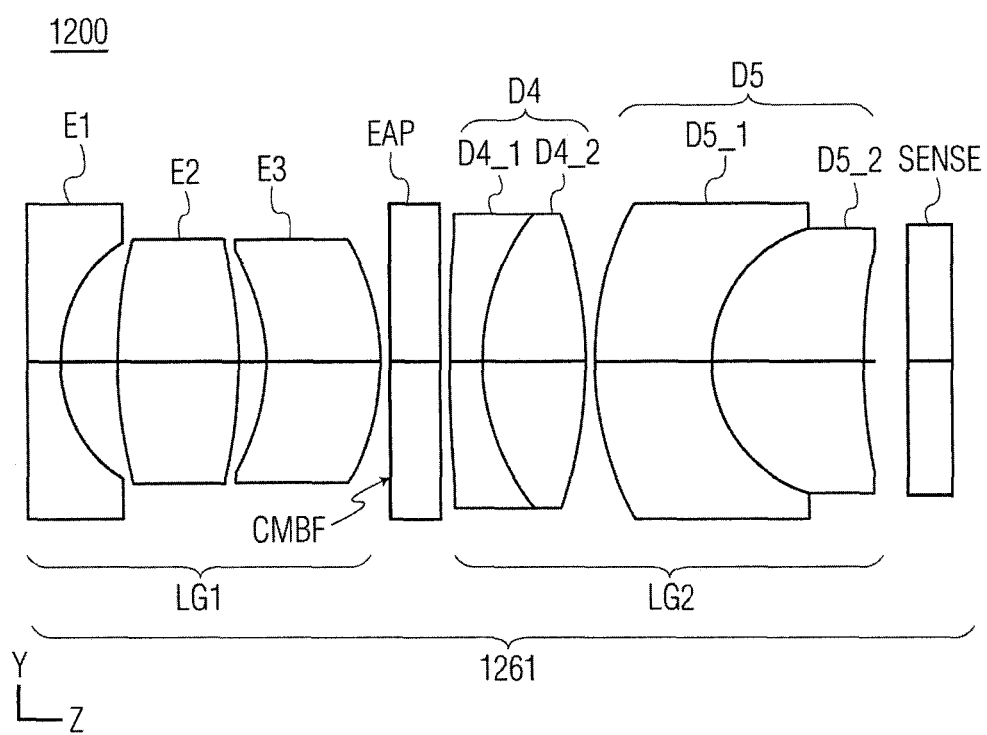
FIG. 12 is a cutaway side view of a lens array in accordance with embodiments of the present system.

FIG. 12 is a cutaway side view 1200 of a lens array 1261 in accordance with embodiments of the present system. The lens array 1261 may be similar to the lens array 1061 and may include elements such as one or more of lenses E1, E2, E3, D4, and D5, as well as a limiting aperture portion EAP (also referred to as a STOP or pupil (s)) and a sensor SENSE. However, it is also envisioned that the sensor SENSE may be independent of the lens array 1261. The lens array 1261 may include first and second lens groups, LG1 and LG2, respectively, each being a singlet and including one lens. However, in other embodiments, the first and second lens groups LG1, LG2 may include more than one lens. Lenses D4 and/or D5 may be lens doublets and include lens pairs D4_1 and D4_2; and D51 and D52, respectively, including 2 lenses attached to each other. However, in other embodiments, lenses D4 and/or D5 may be single lenses or include more than two lenses. As shown in FIG. 10B (and FIG. 12), the optical lenses and elements are serially connected back to back so as to share a central axis and have a same diameter, such as slightly less than 4 mm, so at to fit within the 4 mm outer housing of the image capture device 1050. The outer diameter of the housing may be in the range of 2-4 mm, for example.

FIG. 13A is alight ray trace 1300A of a lens array 1261 having an 80 degree FOV in accordance with embodiments of the present system. In the light trace 1300A, seven objective field points are plotted (e.g., FP-1 through FP-7) and the lens system focuses these objective field points (e.g., FP-1 through FP-7) on an image plane (such as an image plane of a CMOS or CCD image capture screen) of a sensor SENSE as shown by image plane points FP-1' through FP-7', respectively.

The first light group LG1 may be configured to collimate or substantially collimate objective image rays such that the objective image rays are incident upon the limiting aperture portion EAP which comprises complementary multiband bandpass filters (CMBFs) included in a CMBF pair, such as shown in FIGS. 10C, 10D. Thus, the first lens group LG1 may collimate or substantially collimate incoming light rays which are then incident upon the aperture portion EAP and/or CMBF pair as will be discussed below.

The CMBFs are described in US2011/0115882, which is incorporated herein by reference in its entirety, generally create two viewpoints in a single objective lens camera, namely, a right viewpoint of images passing to the right CMBF (CMBF-1 in FIGS. 10C, 10D) and a left viewpoint of images passing to the left CMBF (CMBF-2 in FIGS. 10C, 10D). The CMBFs include a filter pair having a plurality of passbands which pass light within a certain (visible) color spectrum. As shown in FIG. 10E, the color spectrum of each passband of a filter of the CMBF pair is complementary to a color spectrum of the other passband of another filter of the CMBF pair. Further, two key characteristics about the CMBFs pairs as used in the present system are that the passbands (e.g., two or more) of filters (e.g., the first CMBF CMBF-1 and the second CMBF CMBF-2 of the CMBF pair) are staggered so only one viewpoint is opened at a time when a light band matched to that passband of the plurality of passbands is illuminated, and the passbands are positioned throughout the visible spectrum, so each viewpoint can render color by taking RGB spectral images.

Accordingly, an illumination system that illuminates an object of interest comprises a white illuminator source and an illuminator CMBF pair identical to the CMBF located at the limiting aperture portion EAP (also referred to as right and left pupils or apertures). The white illuminator source may be controlled, such as by a controller or processor 2010 shown in FIG. 20, to sequentially illuminate the right and left illuminator CMBFs, CMBF-1 CMBF-2, one at a time. Of course, two white light sources may be provided, namely, a right white light source to provide white light to only the right illuminator CMBF CMBF-1 during a first period of time, and a left white light source to provide white light to only the left illuminator CMBF CMBF-1 during a second period of time.

For example, during the first illumination period, the white illuminator source (or the right white illuminator source) is activated to shine only on the right illuminator CMBF CMBF-1 so that white light from the illuminator source passes through the right illuminator CMBF CMBF-1 to illuminate the object of interest, reflect therefrom and enter the lens array 1261 shown in FIG. 12, passing through the right CMBF located at the limiting aperture portion EAP for being detected or imaged on the entire focal plane array of the detector or sensor SENSE, which may be a CMOS (or CCD). Since the illumination and aperture EAP CMBF pairs are identical, this light provided from the right illuminator CMBF-1, only passes through the right aperture EAP CMBF-1 and is blocked by the aperture's EAP left CMBF-2.

During a next time period, immediately after the first illumination period, the white illuminator source (or the left white illuminator source) is activated to shine only on the left illuminator CMBF CMBF-1 so that white light from the illuminator source passes through the left illuminator CMBF CMBF-1 to illuminate the object of interest, reflect therefrom and enter the lens array 1261 shown in FIG. 12, passing through the left CMBF located at the limiting aperture portion EAP for being detected or imaged on the entire focal plane array (FPA) of the detector or sensor SENSE. This light provided from the left illuminator CMBF-2, only passes through the left aperture EAP CMBF-2 and is blocked by the aperture's EAP right CMBF-1.

As shown in FIG. 10E, the two identical CMBF pairs, where one CMBF pair is located in front of the white light source(s) and the other CMBF pair is located at the limiting aperture portion EAP, have three right passbands and three left passbands which are complementary to each other, thus only allowing either right light (e.g. dotted lines in FIG. 10E) or left light (e.g. dashed lines in FIG. 10E) to pass through the system for sequentially imaging a right image on the entire (FPA) of the detector or sensor SENSE, and a left image on the entire (FPA) of the detector or sensor SENSE, one at a time. However, each viewpoint takes a different spectral image from the other viewpoint hence yielding a different color image relative to the other. This color mismatch in the two viewpoints could lead to color rivalry, where the human vision system fails to resolve two different colors. The difference will be closer if the number of passbands in a CMBF pair is increased, and thus more than the three complementary passbands (shown in FIG. 10E) are used. Thus, it is preferred to have as many complementary passbands in each filter of the CMBF pair.

As described, the illuminator CMBF pair is positioned in front of a white light source. With regard to a location of the aperture CMBF pair in the lens array 1261, it may be positioned between the first and second lens groups LG1 and LG2, respectively, to form the limiting aperture portion EAP, which may be two semi-circles or two circles touching each other of separated from each other, as shown in FIGS. 10C, 10D, so as to receive collimated light from the first lens group LG1.

The CMBF pair may include one or more CMBFs (e.g., a first and second CMBFs) each of which may include one or more layers (e.g., 100 layers etc.) to form an interference filter with sharp edges and may be configured to filter incident light so as to enable sensing of image information suitable for rendering as stereoscopic images (i.e., 3D images) as described in US2011/0115882. The CMBF pair or parts thereof may be an independent optical element or may be integrated with the limiting aperture portion EAP and/or a lens element of the lens array 1261. For example, the layers of the CMBF pair may be directed formed or coated over portions of a lens to form the limiting aperture portion EAP, where the portions may be semicircular shape, each semicircular covering half the area of a circular limiting aperture portion EAP, or two circles touching each other of separated from each other, as shown in FIGS. 10C, 10D, for example. In one embodiment, the both the illumination and pupil CMBFs have a substantially flat surface as shown by the limiting aperture portion EAP in FIG. 12 comprising the pupil CMBF pair. Accordingly, if the CMBF pair (or parts thereof) is integrated with a lens element, the CMBF pair should be situated upon a flat or substantially flat surface such as a surface of the limiting aperture portion EAP of the lens D4 which is adjacent to the EAP. The CMBF pair may an interference type filter and may function as pupils to provide stereoscopic image information suitable for rendering stereoscopic images. The pupil CMBF pair (as opposed to the illumination CMBF located in front of a white light source) is preferably situated between the first and second lens groups LG1 and LG2, respectively, so that light incident upon the pupil CMBF pair (e.g., from the first lens group LG1) has a normal or minimal angle of incidence of light (AOI) from the object upon the CMBF pair which is less than or equal to a threshold angle of incidence (TAOI) value. For example, in some embodiments of the present system, a TAOI value may have a value such as 23 (e.g., for 80 FOV lenses of the present system). Further, the TAOI may be set in accordance with characteristics of a CMBF pair. However, other values and/or ranges of values for the TAOI are also envisioned. Accordingly, the lenses of the first lens group LG1 (e.g., E1, E2, and/or E3 in the present example) should be configured such that the angle AOI is less than or equal to a desired threshold angle of incidence (TAOI) value.

Although CMBFs are shown, if two-dimensional (i.e., 2D) images are desired, the CMBFs may be inactivated, bypassed, and/or removed.

The second light group elements LG2 may then receive incident light and focus the incident light upon an image plane of the image sensor SENSE.

The image sensor SENSE may then form corresponding signals and transmit these signals for further processing to render stereoscopic images (3D) or (2D images).

With regard to construction of the CMBF pair, this filter may, for example, be deposited (e.g., using a plurality of layers such as 100 layers, etc.) upon the EAP and/or the lens D4 (e.g., D4_1). In some embodiments, the CMBF pair is integrated with a flat surface of the lens array 1261 such as the lens D4. Accordingly, the CMBF pair may include one or more coatings or layers applied directly upon a flat or substantially flat surface (depending on the eventual design) of the lens array 1261 such as the lens D4_1.

As shown in FIG. 12, detector optics comprising the two light group elements LG1, LG2, includes lenses D4, D5 in second light group elements LG2, where at least one of the lenses D4, D5 has one un-partitioned section that covers both the right pupil CMBF-1 and a left pupil CMBF-2 (FIGS. 10C, 10D), for directing and/or focusing light passing through the pupil CMBFs, e.g., CMBF-1, CMBF-2 onto the camera or SENSE, such as described in US 2011/0115882, and U.S. patent application Ser. No. 13/628,788, which claims priority to U.S. Provisional Patent Application Ser. No. 61/539,808. As shown in FIG. 12, the detection lens system includes optical lenses and elements E1, E2, E3, EAP, D4, D5 that are serially connected back to back sharing a central axis and having substantially the same diameter, such as slightly less than 4 mm, so at to fit within a 4 mm outer housing of an image capture device including the camera 125 and the detection lens system. Similarly, at least one of the lenses E1, E2, E3 has one un-partitioned section that covers both the right pupil CMBF-1 and a left pupil CMBF-2.

Although exemplary lens arrays 1261 including lenses having exemplary characteristics such as surface, type, radius, curvature, thickness, materials, diameter, comic, focal lengths, lens spacing, etc., are shown and described herein, it is envisioned that one or more of these characteristics may be changed by a user to obtain desired diameters, focal lengths, FOVs, speed, filtering, etc. of a corresponding lens array. For example, the lens arrays 1261 may be scaled with respect to diameter of the lenses to obtain different lens diameters, etc. However when scaling, optical characteristics of the lens array 1261 may vary slightly (e.g., based upon the scaling) and introduce undesirable imaging effects such as blurring. Accordingly, fine tuning of a scaled lens array may be necessary to reduce these undesirable imaging effects. More particularly, when scaling the lens, a ratio of lens curvatures, inter-lens spacing, lens thicknesses, and/or the glass type should be substantially maintained.

The EAP includes a limiting aperture which may limit an amount of light passing through the lens second lens group LG2 of the lens array 1261, and comprises a lens coated with layers of the interference filter to form the pupil CMBF pair as shown in FIGS. 10C, 10D. In case the pupil CMBF pair do not cover the entire lens of the EAP and are rather included over two apertures or pupils (e.g., two circles shown in FIG. 2D), then the remaining portions of the EAP lens (which is not covered by the CMBF) may be black (e.g., a black coating) to stop passage of light. Thus the system may control an amount of light passing through the lens array 1261. Accordingly, by limiting (e.g., actively or passively) the amount of light passing through the lens array 1261, image flooding and/or saturation may be reduced and/or entirely prevented. In addition to the pupil CMBF which may located on the EAP or D4_1, the EAP may include an active filter which may operate under the control of a controller of the system or may include a passive filter. With regard to sizing of the EAP, it may be shaped and/or sized such that the entire limiting aperture is used, and thus the pupil CMBF pair (being two semi-circles) covers the entire EAP as shown in FIG. 10C. Thus, the EAP may have, for example, a diameter which is substantially the same size or slightly larger than that of one or more of the lens elements E1, E2, and/or E3. Accordingly, image rays incident upon all the EAP may pass through a workable area of the EAP and be filtered as opposed to fully blocked as would occur when incident upon non-workable areas of the EAP (outside the two CMBF circles/pupils in the embodiment shown in FIG. 10D). Thus, the EAP may reduce or entirely prevent vignetting of the FOV. However, in yet other embodiments, the EAP may be shaped and/or sized to provide vignetting of the FOV where the two CMBF circles shown in FIG. 10D touch each other and thus have zero separation therebetween. The two CMBF circles of FIG. 10D may be any size, including having a diameter that equals the radius of the limiting aperture portion EAP, and thus the two CMBF circles of FIG. 10D touch each other and touch the periphery of the limiting aperture portion EAP.

Lens, Filter and Sensor Selection

In embodiments of the present system, as shown in FIG. 12, E1 is a plano-concave lens such as a G314-000-000 by Qioptiq Co. Fairport, N.Y.; E2 is a plano-convex lens, 3 mm diameter by 6 mm FL (focal length) such as an NT32-953, by Edmund Optics, Inc.; E3 is a lens having opposite surfaces that have substantially parallel curvature, where the first or front surface (facing E2) has a radius of approximately 2 mm, and the second or rear surface (facing tEAP) has a radius of approximately −2 mm; EAP is a dual aperture mask CMBF pair spreading to D4; D4 is an achromatic doublet lens, 3.0 mm diameter by 6.0 mm FL, such as an NT45-089, by Edmund Optics, Inc; D5 is doublet lens with a focal length which is less than the focal length of D4; and SENSE is a CMOS detector array, MO-B1003, by Misumi, Inc., Taiwan. For example, D5 may include a 1.8 mm square CMOS imager. However, other shapes for the CMOS imager are also envisioned.

Surface Data Summaries

Surface data summaries for the 80, 100, 130, 140, 150, and/or 160 degree FOV lens arrays, similar to the lens array 1261 of FIG. 12, in accordance with embodiments of the present system are shown in Table 1 below. More particularly, table 1 illustrates surface data summaries for lens elements E1, E2, E3, D4, and D5 (or lens portions thereof) of the corresponding lens arrays 1261 and table 2 illustrates lens focal lengths for the for 80-160 degree FOV lens arrays in accordance with embodiments of the present system.

TABLE 1

| Lens Element | LENS FOCAL LENGTH FOV | | | | | | |
|---|---|---|---|---|---|---|---|
| | 80 Deg | 100 Deg | 120 Deg | 130 Deg | 140 Deg | 150 Deg | 160 Deg |
| E1 | −1.998 | −1.485 | −1.389 | −1.353 | −1.287 | −1.242 | −1.207 |
| E2 | 2.690 | 2.496 | 2.61 | 2.69 | 2.673 | 2.756 | 2.704 |
| E3 | 28.536 | 13.281 | 14.612 | 14.387 | 10.975 | 9.714 | 8.829 |
| D4_1 | −2.759 | −2.237 | −2.35 | −2.363 | −2.27 | −2.268 | −2.252 |
| D4_2 | 2.028 | 1.941 | 1.935 | 1.909 | 1.891 | 1.877 | 1.875 |
| D5_1 | −4.050 | −7.921 | −9.578 | −8.427 | −7.889 | −8.739 | −7.756 |
| D5_2 | 1.656 | 1.736 | 1.843 | 1.728 | 1.649 | 1.732 | 1.615 |
| D4 | 6.115 | 8.881 | 7.233 | 6.851 | 7.511 | 7.04 | 7.223 |
| D5 | 4.461 | 3.546 | 3.539 | 3.409 | 3.308 | 3.264 | 3.224 |

Focal Length and Pupil Diameter

Focal length and pupil diameter information for corresponding 80, 100, 130, 140, 150, and/or 160 degree FOV lens arrays in accordance with embodiments of the present system is shown in Table 2 below.

TABLE 2

| | EFFECTIVE FOCAL LENGTHS | | | | | | |
|---|---|---|---|---|---|---|---|
| | 80 Deg | 100 Deg | 120 Deg | 130 Deg | 140 Deg | 150 Deg | 160 Deg |
| EFFECTIVE FOCAL LENGTH | 1.288854 | 1.106809 | 0.9874067 | 0.9406546 | 0.902855 | 0.8866931 | 0.8694922 |
| ENTRANCE PUPIL DIAMETER | 1.12406 | 0.8123423 | 0.7204347 | 0.6843194 | 0.6563903 | 0.6426381 | 0.630205 |

Referring to the light ray trace 1300A of the 80 degree FOV lens as shown in FIG. 13A, the optical configuration of the lenses of the first lens group LG1, creates a normal or minimal angle of incidence of light has an AOI of 23 degrees which is less than or equal to the TAOI value for this lens which is 25 degrees. As shown in FIG. 13A, the angle of incidence of light AOI is the angle between the incident light beam, which is incident on the surface of the CMBF, and a normal or a line perpendicular to the CMBF surface.

The lenses of the first lens group LG1 are configured, such as by proper selection lens parameters of lenses E1, E2, E3, such as radius, thicknesses, focal length, glass type, to provide substantially collimated light for all field points in the CMBF space of the lens design such that the light rays in this space, that are incident on the CMBF, have a low or minimal angle of incidence (AOI) on the CMBF. The low AOI is less than or equal to the threshold angle of incidence (TAOI) value of 23-27 degrees, such as 25 degrees. The lenses of the second lens group LG 2 are configured (by proper selection parameters of the lenses D4, D5) to focus light passing through the CMBF pair/EAP to focus the light on the detector or sensor SENSE. Accordingly, the first lens group LG1 is also designed to work in concert with the rear group of elements LG2 to provide high definition (HD) imagery, e.g. 1080-p, over an image format of 1.22 mm by 1.21 mm, for example. This high-definition imagery is accomplished at the full relative aperture (f/n) of the individual designs, e.g., 80-degree design at f/1.2 and at f/1.4 for most of the larger field of view designs. For example, the thickness of the lenses may be in the range of 0.08 mm to 1.5 mm, where the CMBF may be 1-2 mm thick.

Figure 13B:
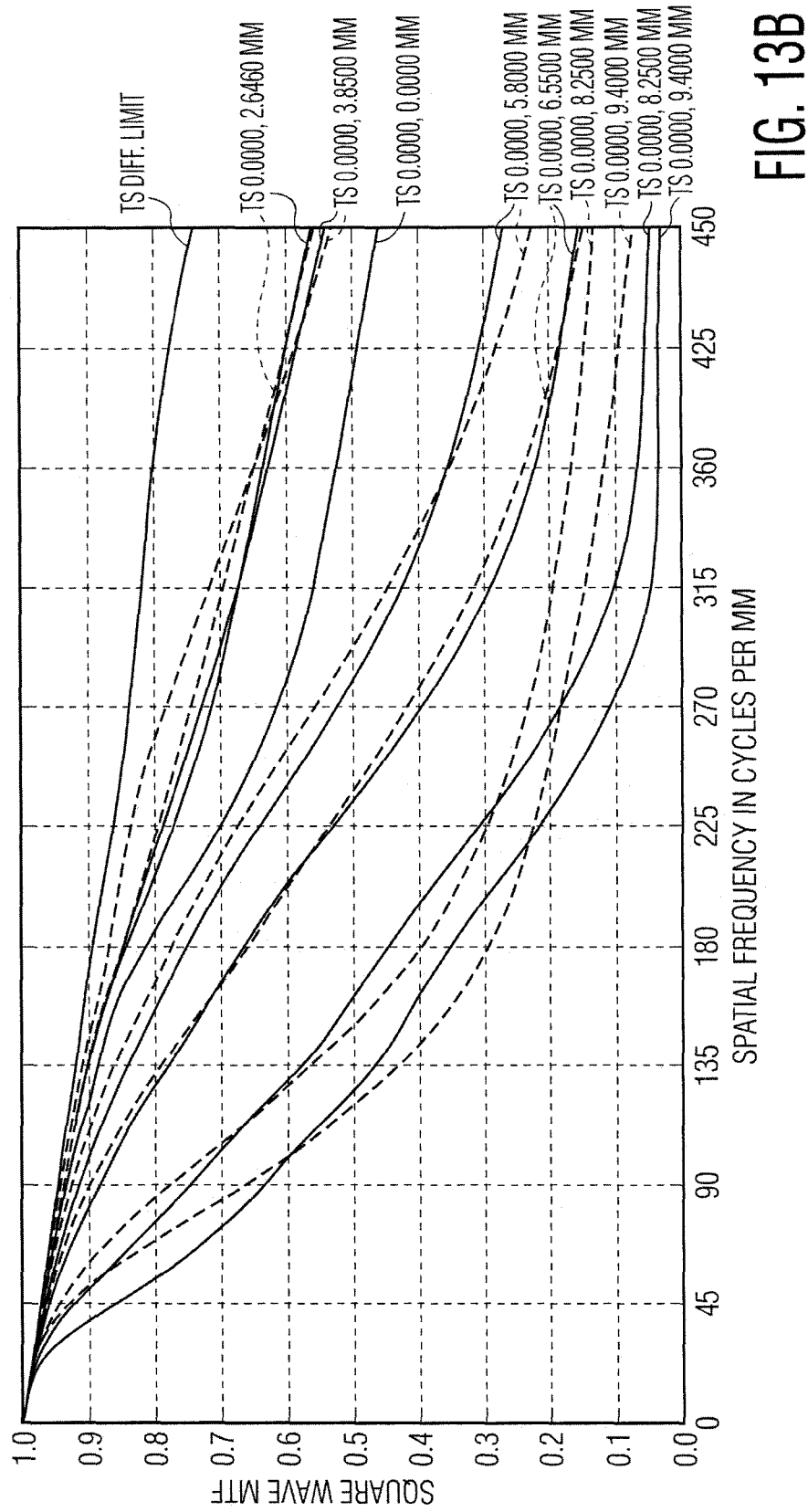
FIG. 13B is a screenshot of graph of square wave MTF vs. special frequency for the lens array having an 80 degree FOV.
Figure 14A:
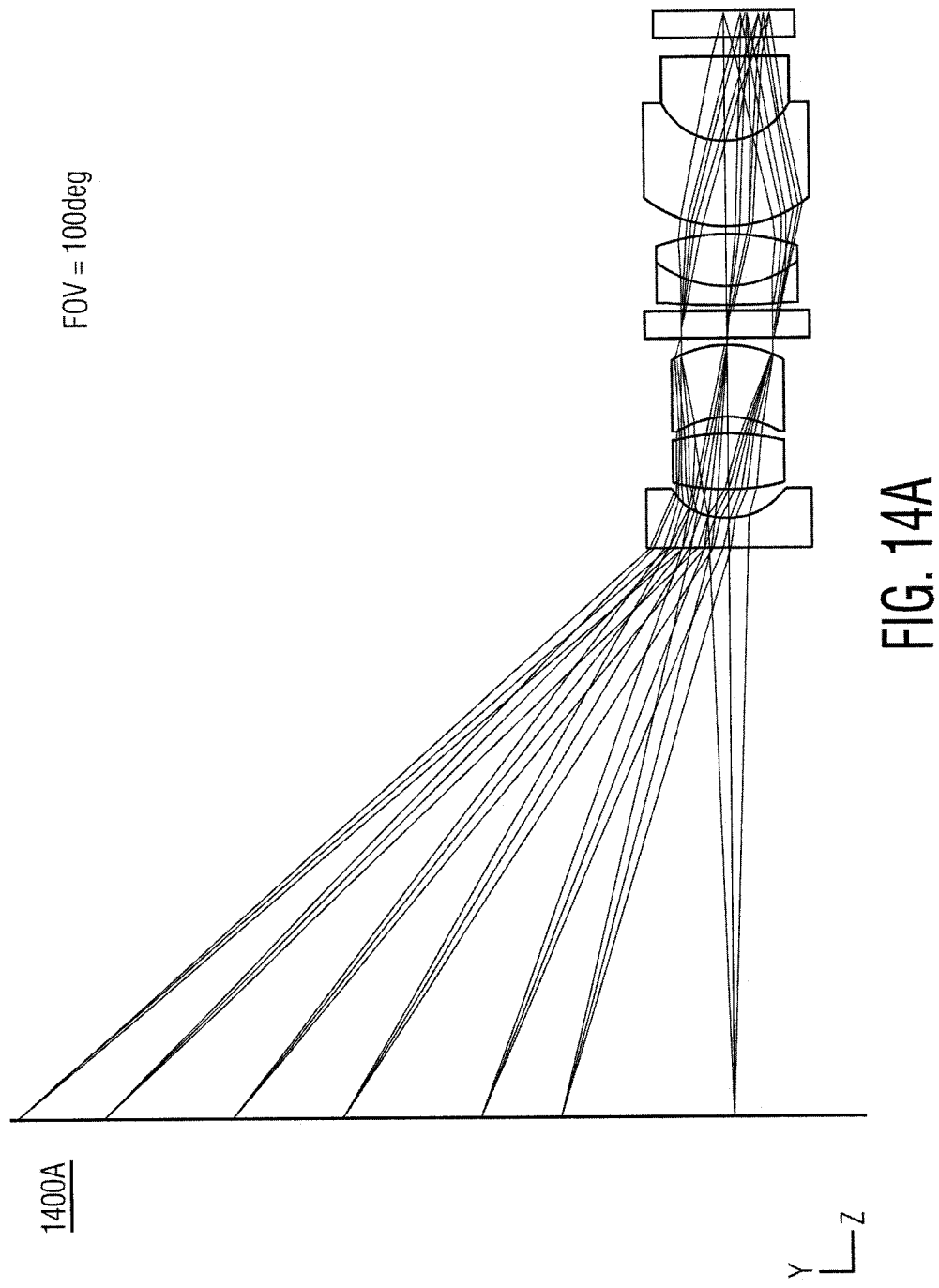
Figure 14B:
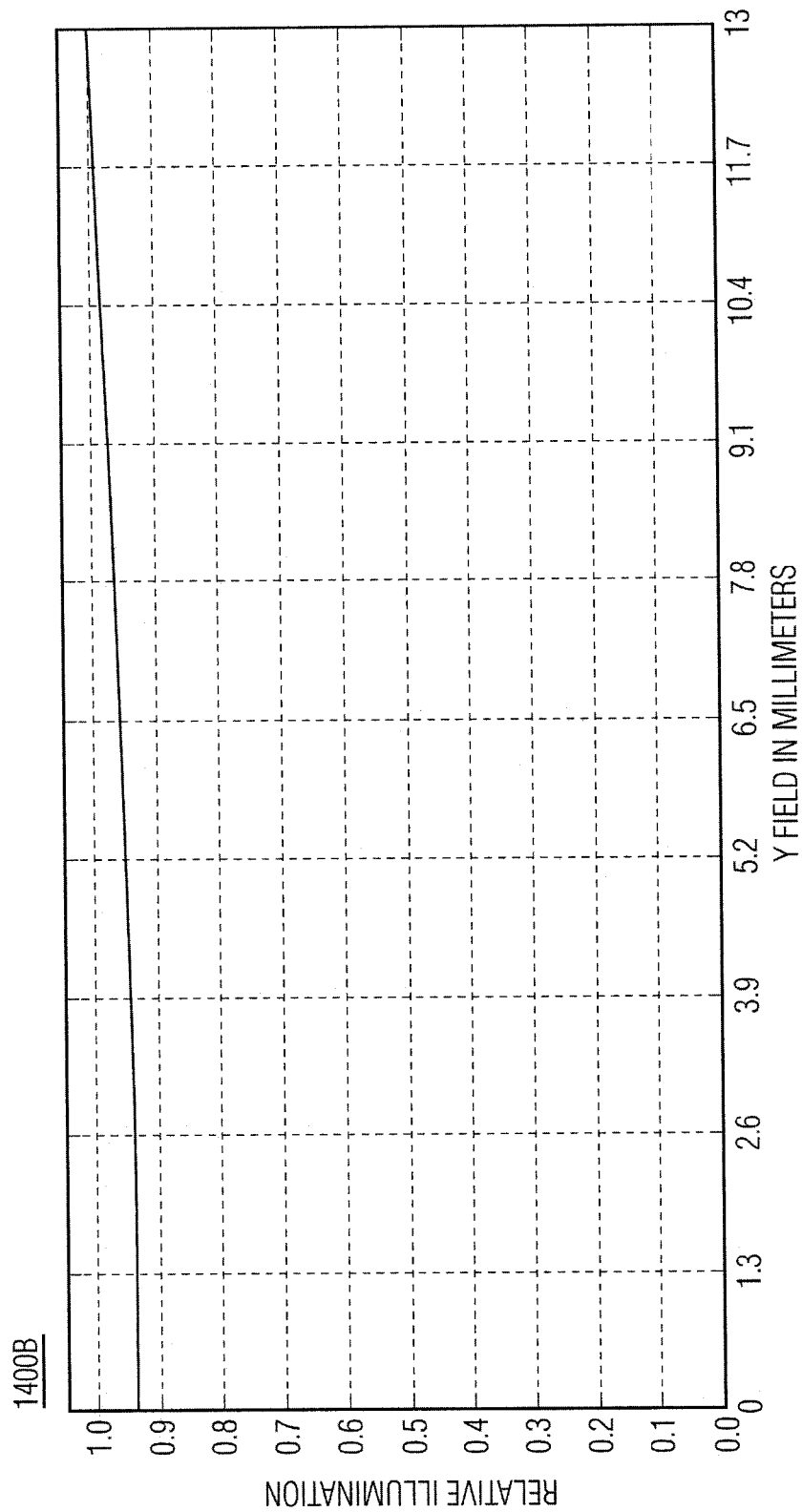
Figure 14C:
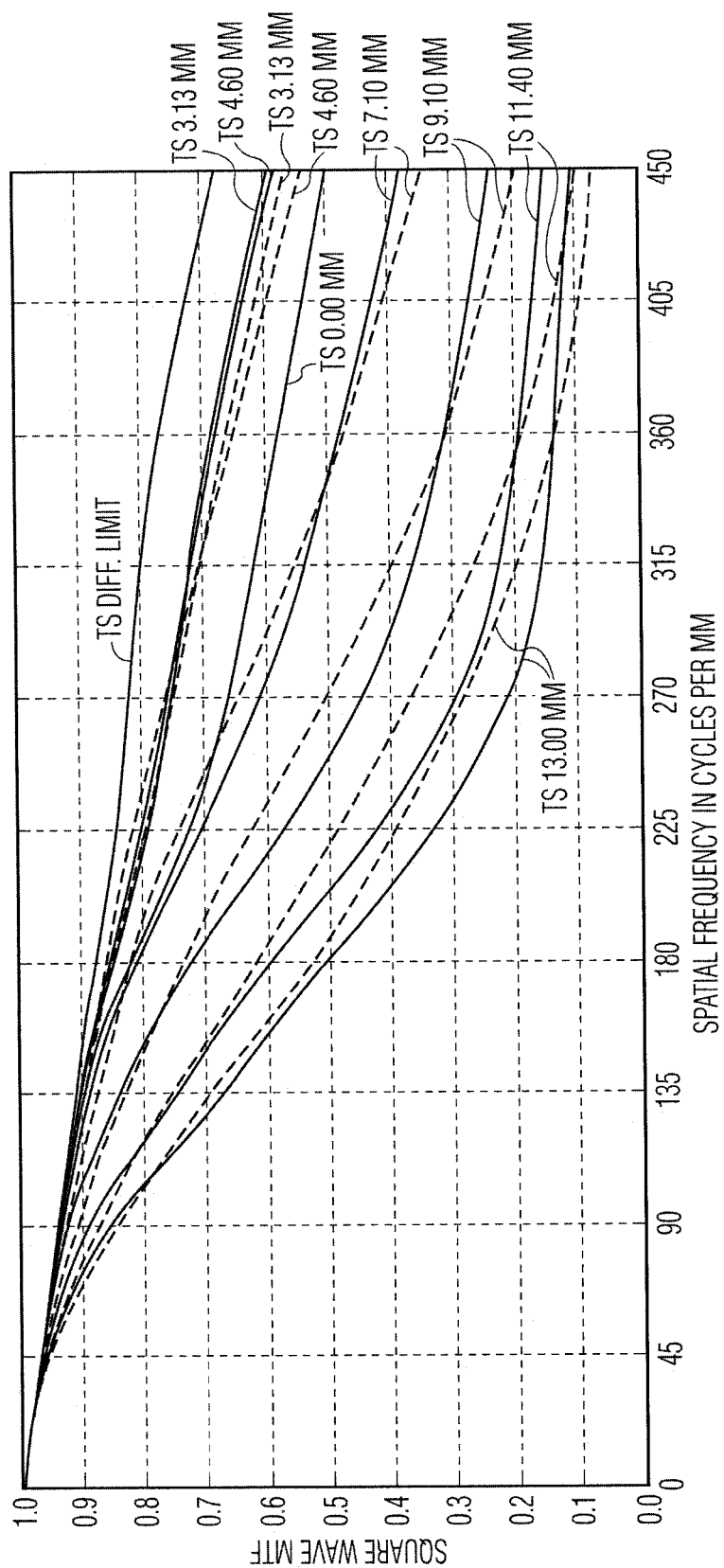
Figure 15A:
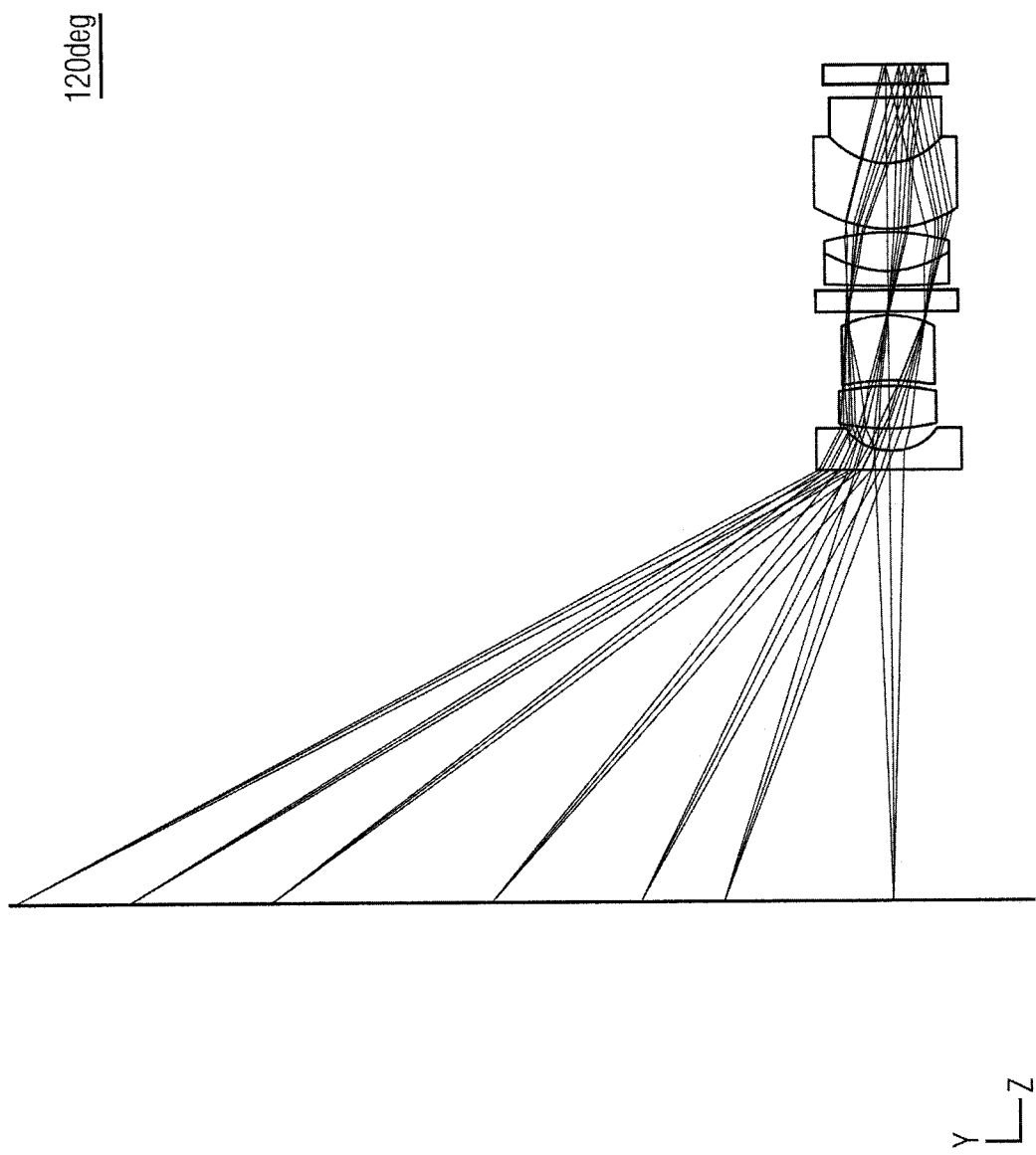
Figure 15B:
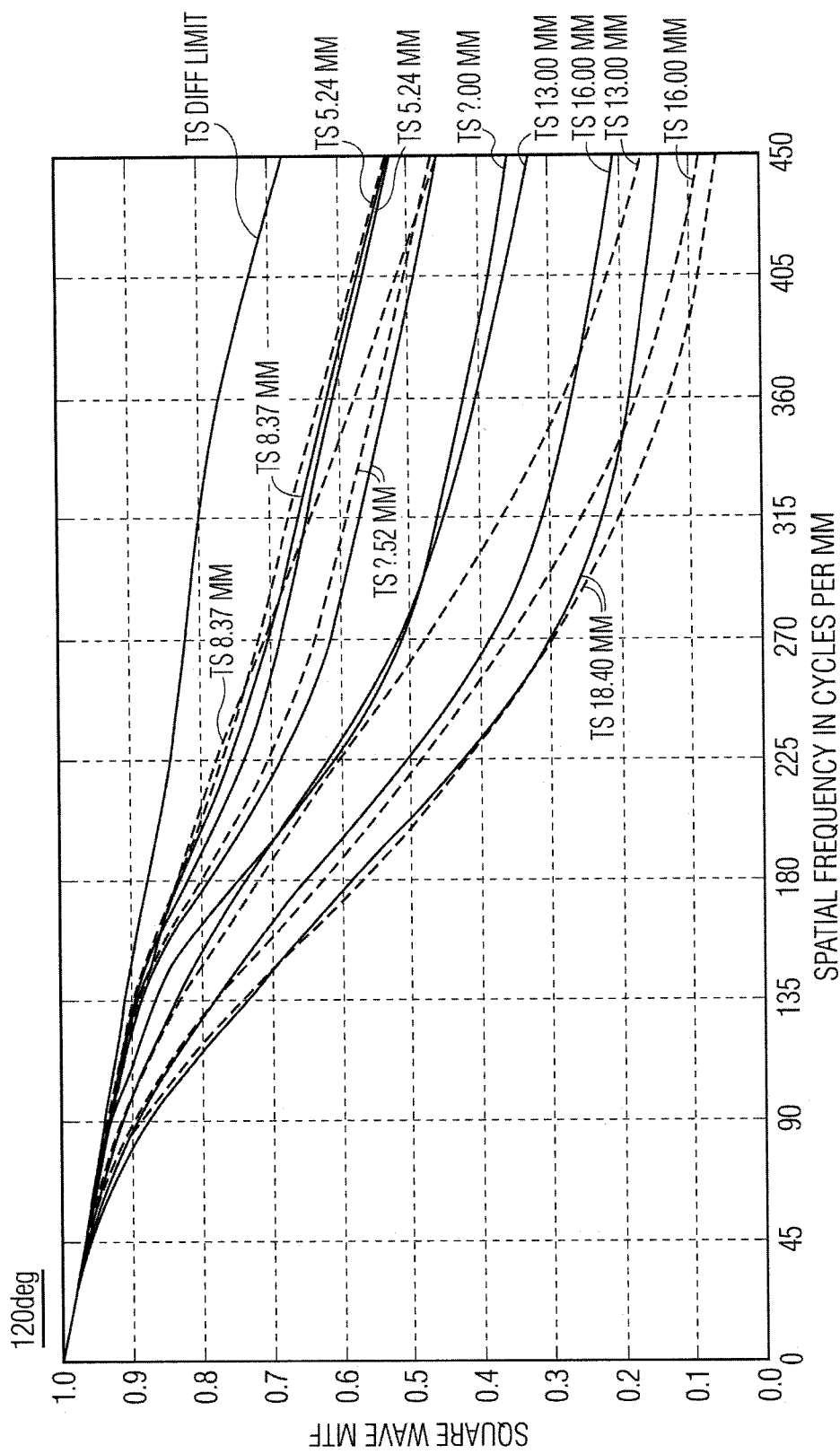
Figure 15C:
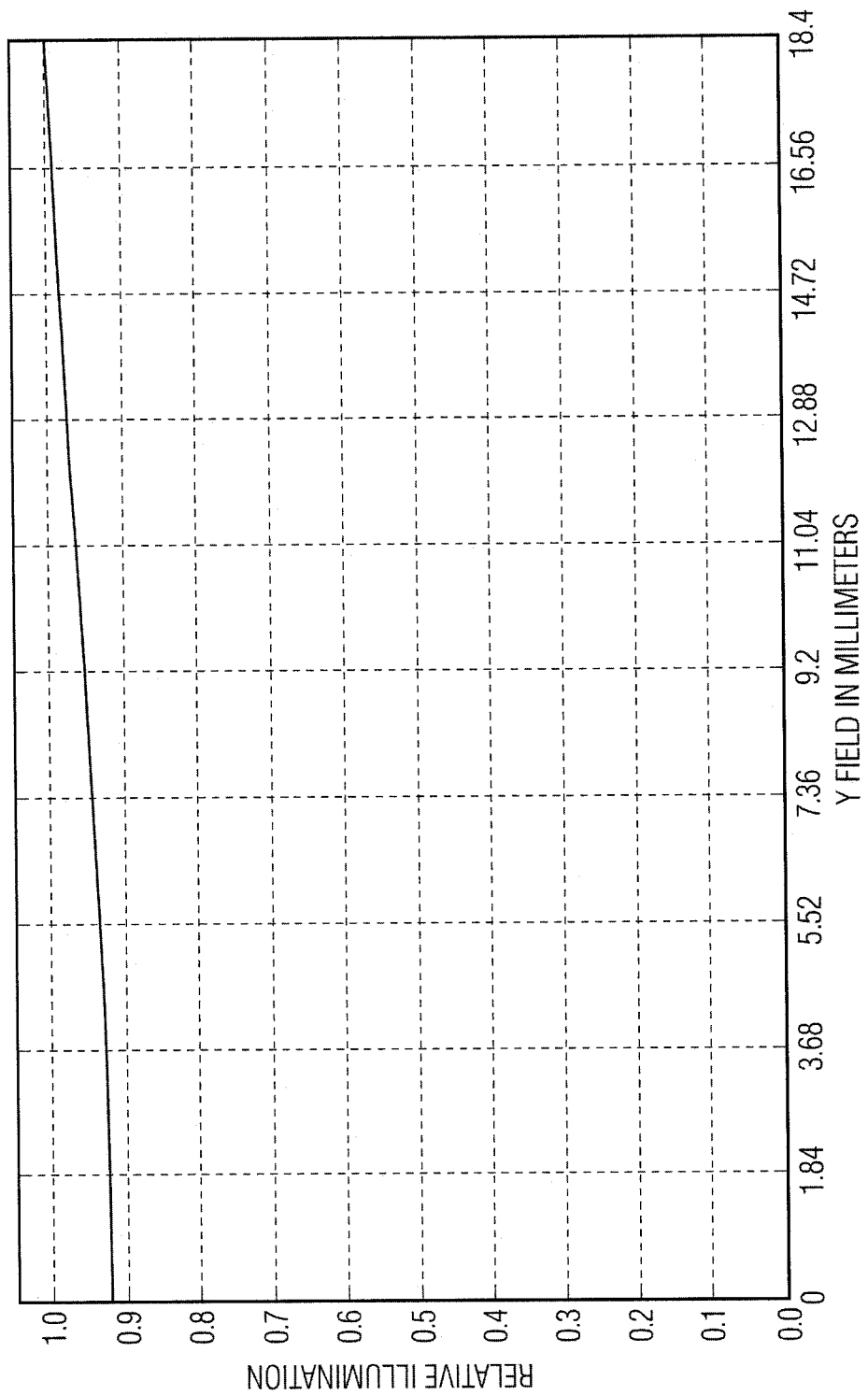
Figure 16A:
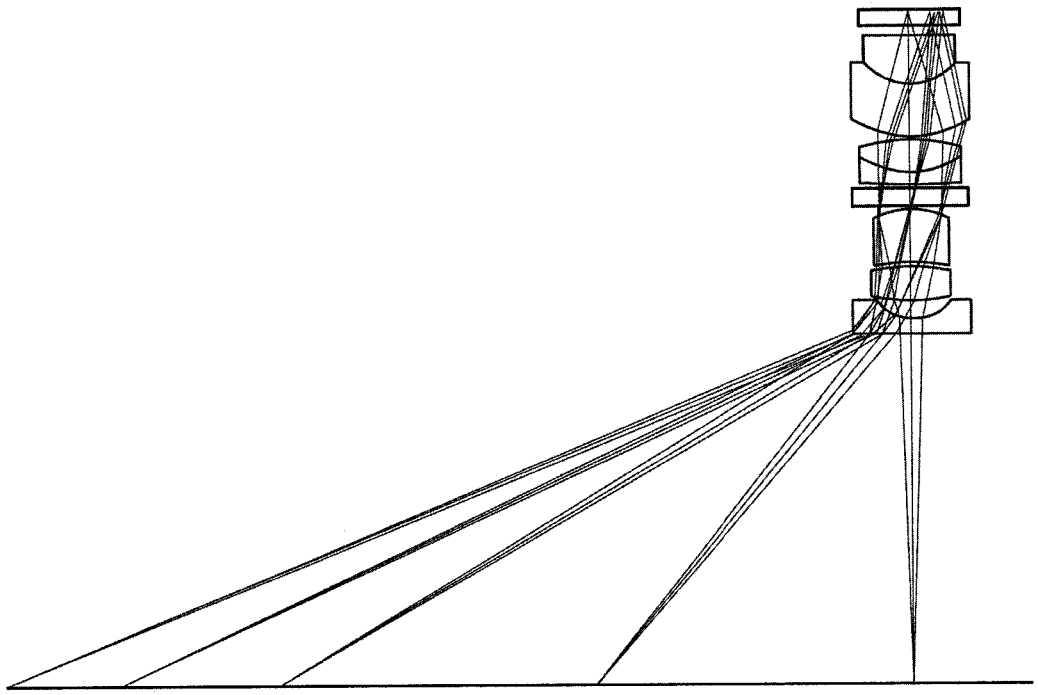
Figure 16B:
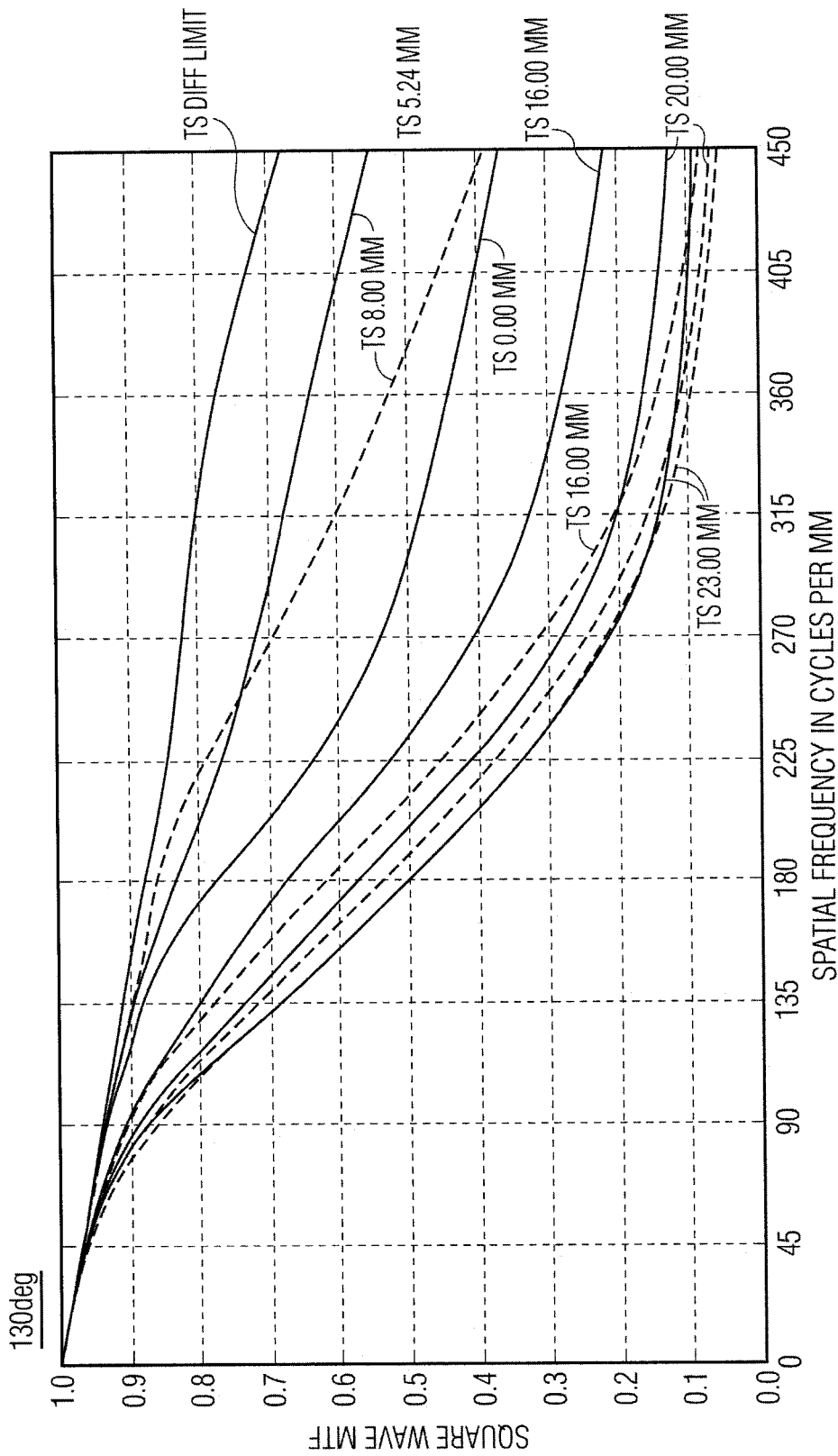
Figure 16C:
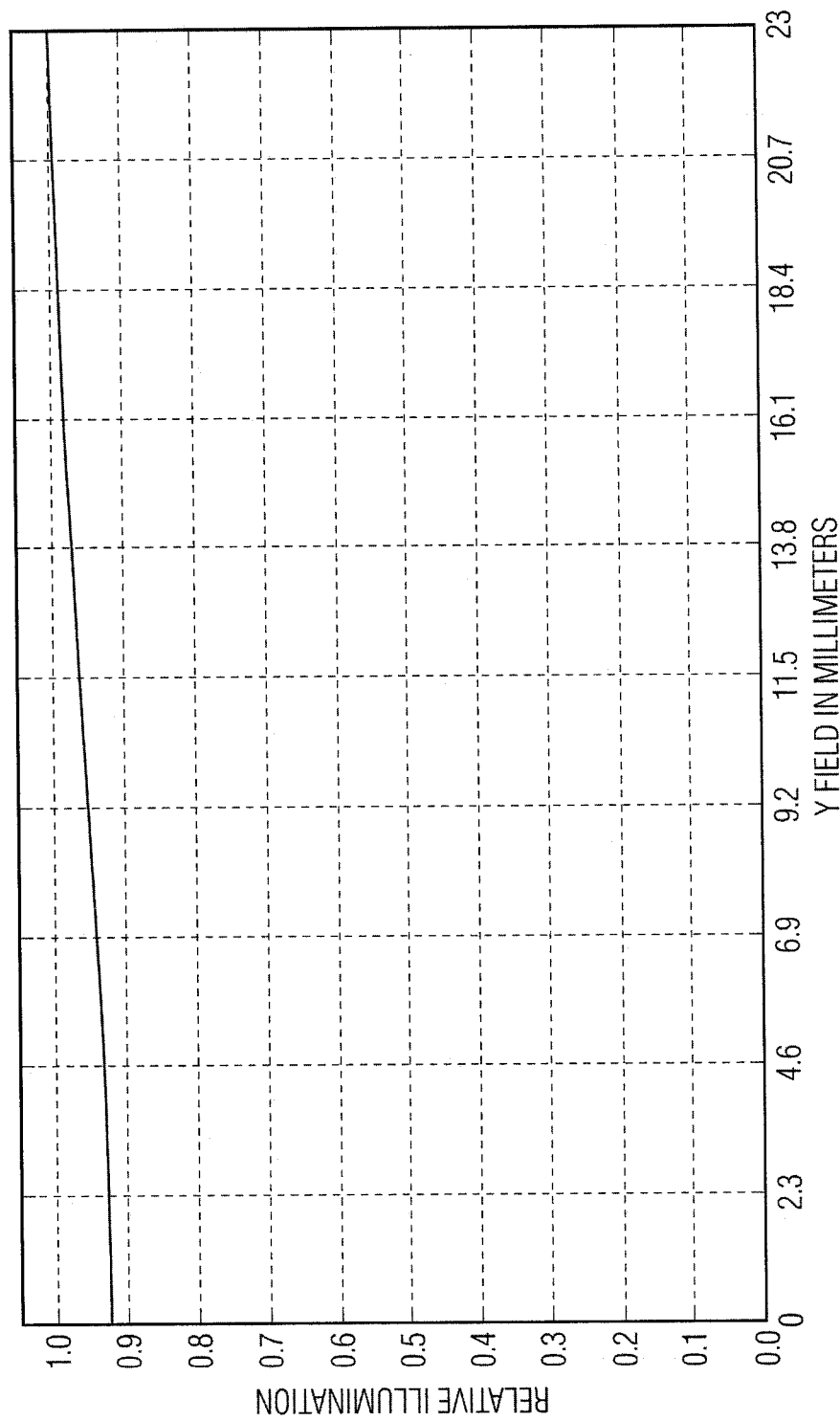
Figure 17A:
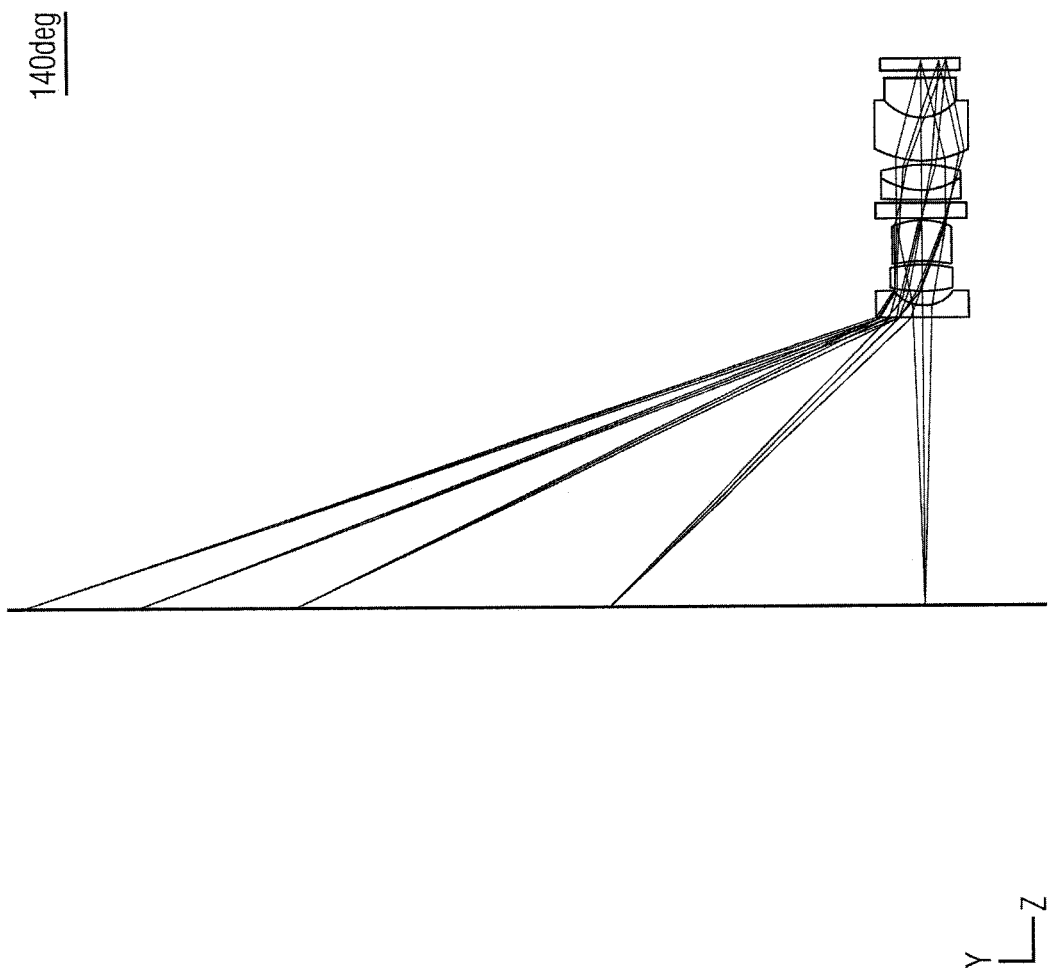
Figure 17B:
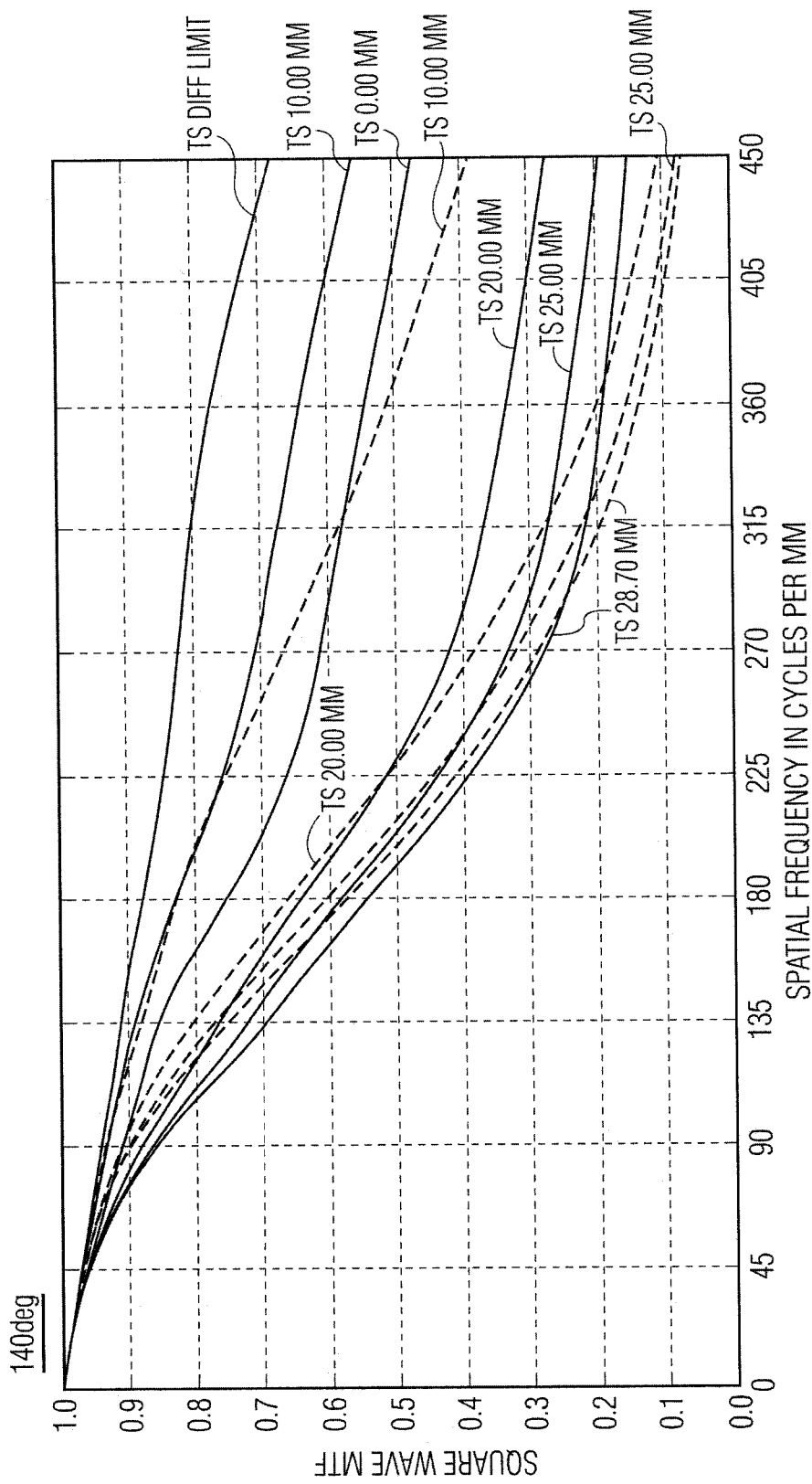
Figure 18A:
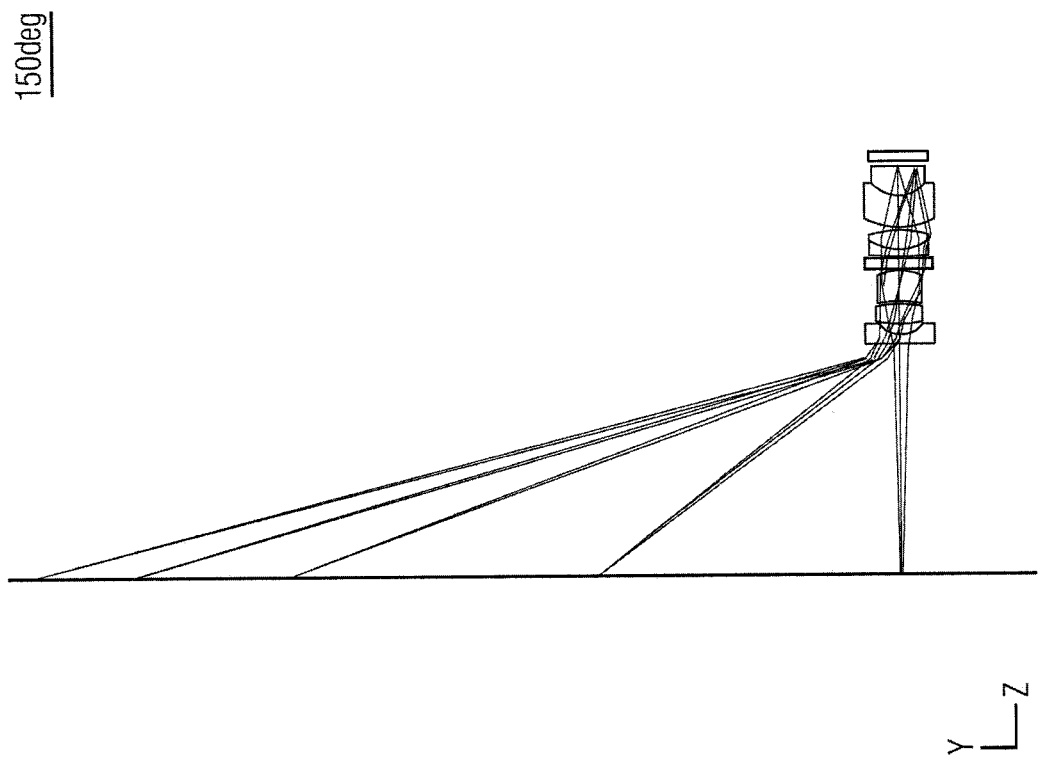
Figure 18B:
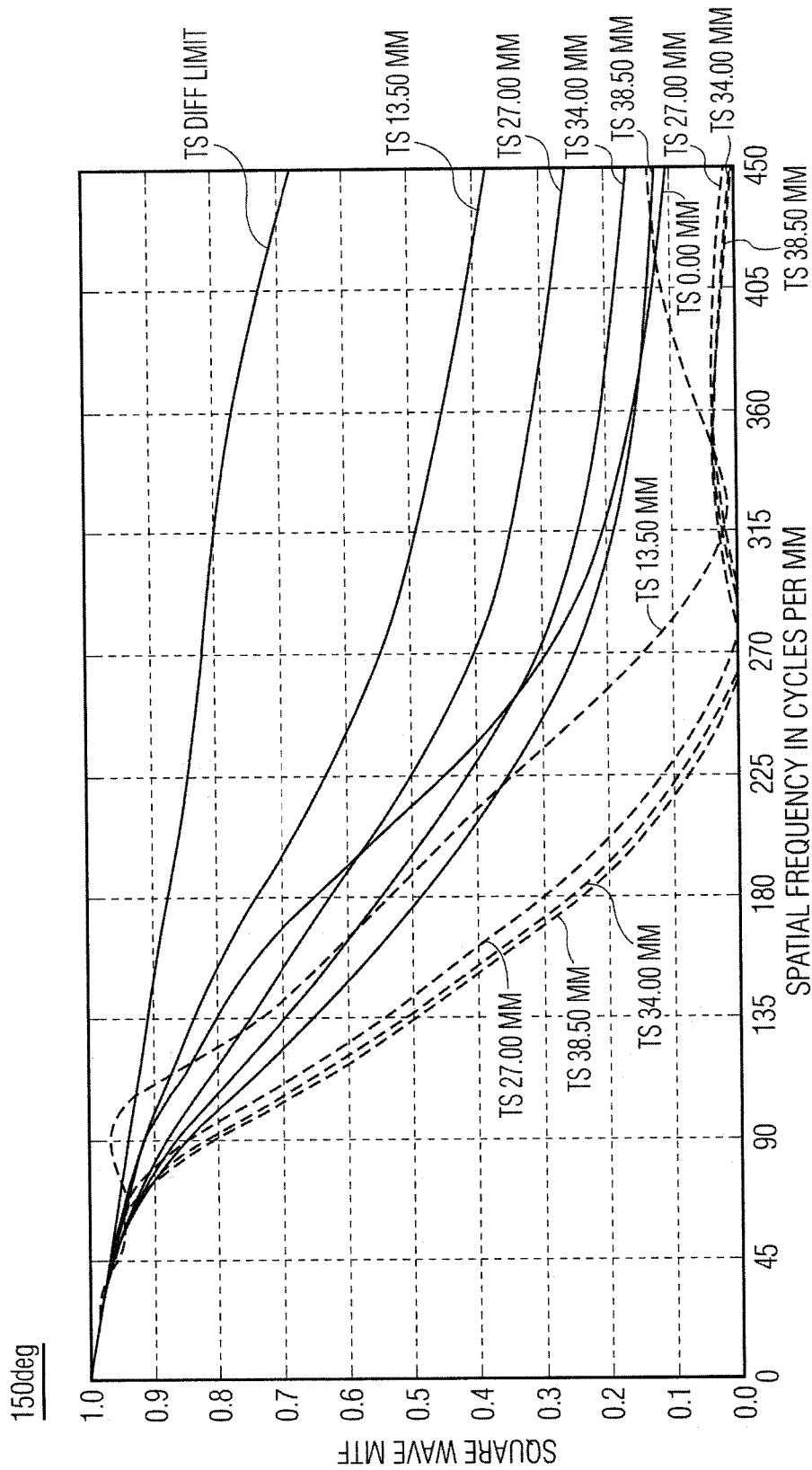
Figure 18C:
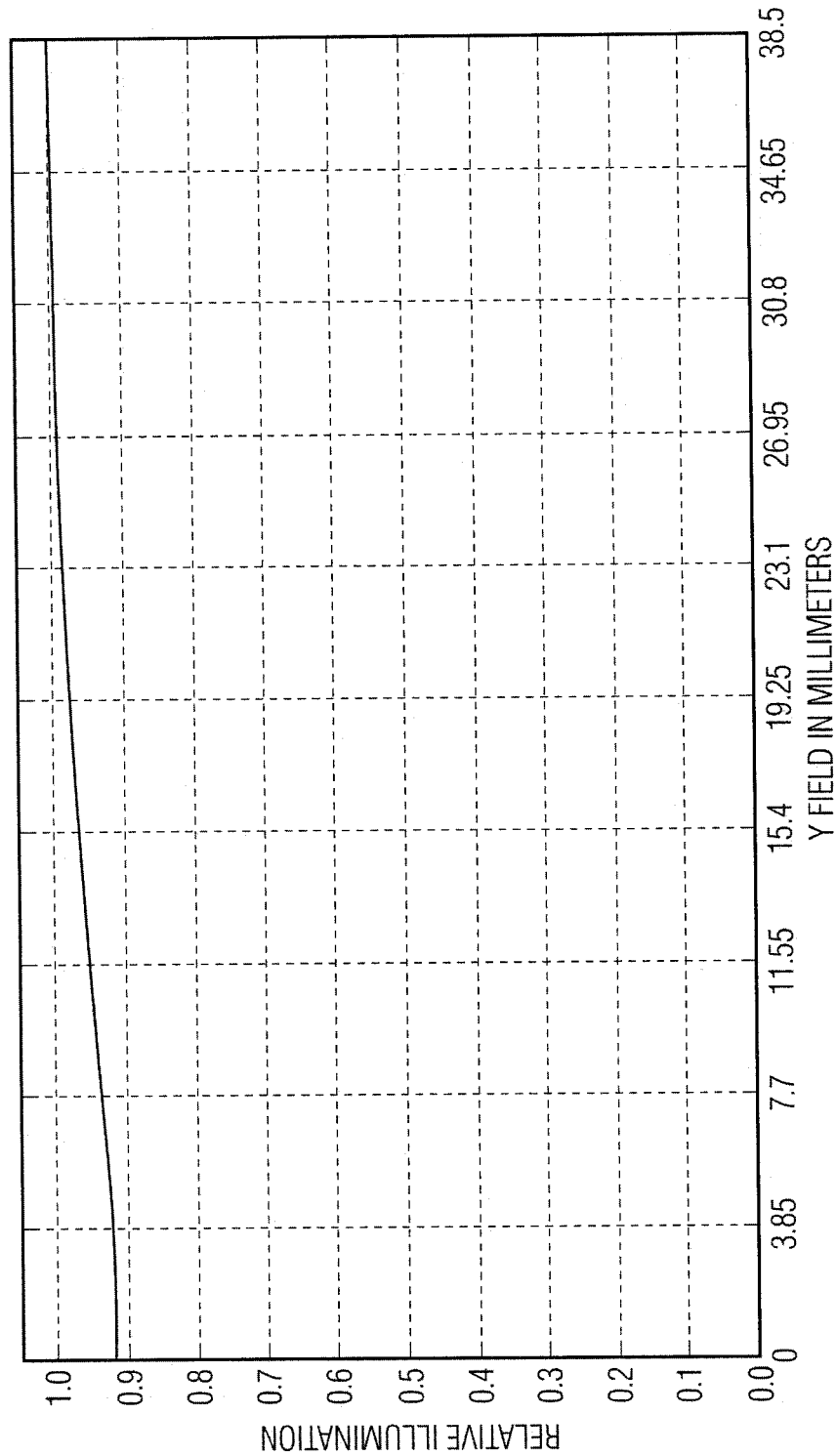
Figure 19B:
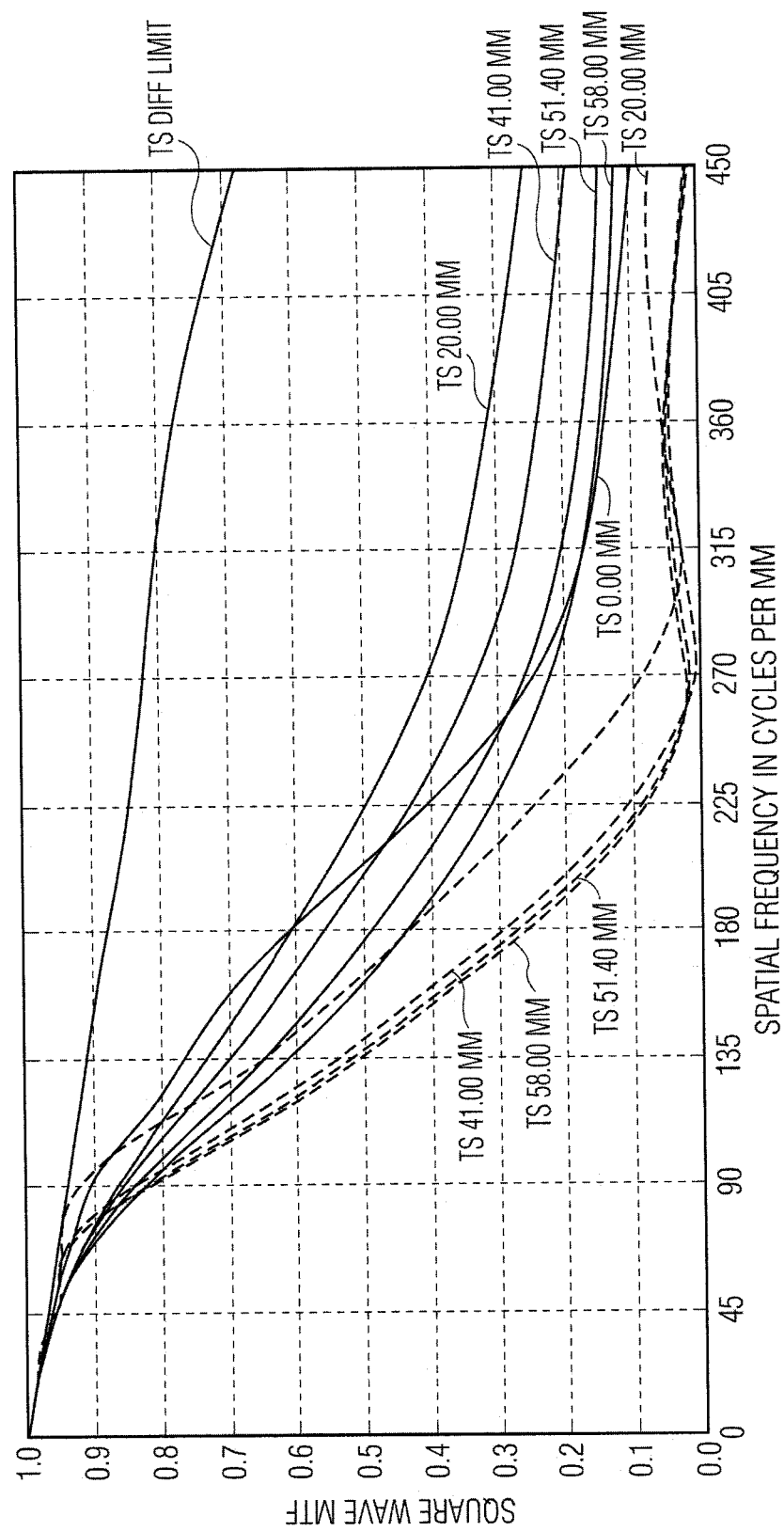

FIG. 13B is a screenshot of graph of square wave MTF vs. special frequency for the lens array 1261 having an 80 degree FOV.

FIG. 13C is a screenshot of graph of relative illumination vs. Y field for the lens array 1261 having an 80 degree FOV.

Light ray traces of 100, 120, 130, 140, 150, and/or 160 degree FOV lenses in accordance with embodiments of the present system are shown in FIGS. 14A, 15A, 16A, 17A, 18A, and 19A respectively.

Graphs of relative illumination vs. Y field for 100, 120, 130, 140, 150, and/or 160 degree FOV lenses in accordance with embodiments of the present system are shown in FIGS. 14B, 15B, 16B, and 17B, 18B, and 19B, respectively.

Graphs of relative illumination vs. Y field for 100, 120, 130, 140, 150, and/or 160 degree FOV lenses in accordance with embodiments of the present system are shown in FIGS. 14C, 15C, 16C, 17C, 18C, and 19C respectively.

Referring back to the process 1100 of FIG. 11, during act 1103, a first light group may collimate or substantially collimate objective image rays such that the objective image rays are incident upon EAP and/or a complementary multiband bandpass filters (CMBF) of a CMBF pair. An angle of incidence of these rays should be less than or equal to a threshold angle of incidence of the CMBF pair (e.g., 23-27 degrees, such as 25 degrees). After act 1103, the process may continue to act 1105.

During act 1105, the process 1100 may control an intensity of the image rays passing through the EAP. Accordingly, a controller (2010 of FIG. 20) of the system may obtain information associated with an intensity of the image rays (e.g., at a point in the image array) and may control a limiting aperture of an objective lens system (e.g., having mechanical and/or electronic shutters such as including liquid crystals that change from transparent to a dark state in response to an applied voltage), to limit an amount of light passing through the EAP so as to prevent image washout, etc. Alternatively or in addition, the controller control may be configured to control intensity of the white light source to provide white light of a desired intensity to the right and left illumination CMBFs (located in front of the white light source) sequentially, for sequentially illuminating the object of interest with a right light (e.g. dotted lines in FIG. 10E) and a left light (e.g. dashed lines in FIG. 10E) that reflect from the object of interest, and pass through the system for sequentially imaging a right image on the entire (FPA) of the detector or sensor SENSE, and a left image on the entire (FPA) of the detector or sensor SENSE, one at a time, After completing act 1105, the process may continue to act 1107.

During act 1107, the process 1100 may filter the collimated light using a pupil CMBF pair, e.g., located or coated on the limiting aperture portion EAP (FIG. 12) in accordance with embodiments of the present system. This act may be performed before, after, and/or concurrently with act 1107. After completing act 1107, the process may continue to act 1109.

During act 1109, the process may focus (e.g., using one or more lenses of a second lens group LG2) and project the limited and/or CMBF pair filtered collimated light upon an image plane such as an image plane of an image capture sensor such as a CCD or CMOS sensor SENSE. After completing act 1109, the process may continue at act 1111.

During act 1111, the process may capture the image incident upon the upon the image plane of the image capture sensor and may transmit signals indicative of the captured image(s) to, for example, an image information transmission device of the system for transmission to an image information receiving device. The received image information may then be processed, stored in a memory of the system, and/or rendered on a user interface (UI) such as a display of the system. After completing act 1111, the process may continue to act 1113, where it ends.

In summary, lens arrays in accordance with embodiments of the present system provide a wide field-of-view (FOV) which may range from about 80° degrees to about 160 degrees (however other values and/or ranges is also envisioned), while providing high-quality images such as full 1080p high-resolution images in two- or three-dimensions. Further, the various lens arrays in accordance with embodiments of the present system may have high speeds as evidence by a maximum speed of f/1.2, for example.

Further, in accordance with some embodiments of the present system, lens arrays may have a maximum diameter which may be as small as 3 mm and, when combined with an image capture device, may provide 2- or 3-D image information at a full 1080 lines sampling for high definition (HD) viewing. Further, the lens arrays such as the lens array 1261 is designed not to vignette over the FOV; this relates to the lens array utilizing the entire limiting aperture (e.g., this refers to the diameter of the STOP or limiting aperture portion EAP shown in FIG. 12) accordingly, the f number of the lens remains constant regardless of aperture settings.

Further, unlike conventional endoscope systems, the present system captures images immediately on an image capture sensor such as CCD or CMOS which is placed adjacent to the last lens of the lens array. Accordingly, there is no need for relay optics (e.g., flexible fiber-optic bundles) which transmit an image a distance until being captured or viewed (e.g., by a user) and, which may distort an image (especially around the peripheral edges of the image) and/or decrease quality and/or brightness of an image.

FIG. 20 shows a portion of a system 2000 in accordance with an embodiment of the present system. For example, a portion of the present system may include a processor 2010 operationally coupled to a memory 2020, a display 2030, RF transducers 2060, a camera/sensors 2090, and a user input device 2070. The memory 2020 may be any type of device for storing application data as well as other data related to the described operation. The application data and other data are received by the processor 2010 for configuring (e.g., programming) the processor 2010 to perform operation acts in accordance with the present system. The processor 2010, so configured, becomes a special purpose machine particularly suited for performing in accordance with embodiments of the present system.

The operation acts may include configuring an endoscopic imaging system by, for example, controlling one or more of a position of an imaging portion, the camera/sensors 2090, and/or the actuators 2060. The camera/sensors may provide information to the processor 2010 such as image information (in 2D or 3D), temperature information, position information, etc. The actuators 2060 may be controlled to position the camera, turn the camera on/off, and/or to provide illumination to a volume of interest (VOI) so that the camera may capture images of a desired subject within the volume of interest in 2D or 3D. The processor 2010 may receive the image information from the camera, and may render the image information on, for example, a user interface (UI) of the present system such as on the display 2030 which may render images in 2D or 3D. Further, the processor 2010 may store the image information in a memory of the system such as the memory 2020 for later use.

The user input 2070 may include a joystick, a keyboard, a mouse, a trackball, or other device, such as a touch-sensitive display, which may be stand alone or be a part of a system, such as part of a personal computer, a personal digital assistant (PDA), a mobile phone, a monitor, a smart or dumb terminal or other device for communicating with the processor 2010 via any operable link. The user input device 2070 may be operable for interacting with the processor 2010 including enabling interaction within a UI as described herein. Clearly the processor 2010, the memory 2020, display 2030, and/or user input device 2070 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 2020 or other memory coupled to the processor 2010.

The program and/or program portions contained in the memory 2020 configure the processor 2010 to implement the methods, operational acts, and functions disclosed herein. The memories may be distributed, for example between the clients and/or servers, or local, and the processor 2010, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 2010. With this definition, information accessible through a network is still within the memory, for instance, because the processor 2010 may retrieve the information from the network for operation in accordance with the present system.

The processor 2010 is operable for providing control signals and/or performing operations in response to input signals from the user input device 2070 as well as in response to other devices of a network and executing instructions stored in the memory 2020. The processor 2010 may be an application-specific or general-use integrated circuit(s). Further, the processor 2010 may be a dedicated processor for performing in accordance with the present system or may be a general-purpose processor wherein only one of many functions operates for performing in accordance with the present system. The processor 2010 may operate utilizing a program portion, multiple program segments, or may be a hardware device utilizing a dedicated or multi-purpose integrated circuit.

FIG. 21 shows a portion of code used to control actuators to position the imaging unit such as to provide a rear view, for example, by rotating at least one link, 2 or more links, and the like. As described in connection with FIG. 7, a rear view along an axis parallel to the longitudinal axis LA of the elongated section 702 may be achieved using two links 711.

While the present system has been described with a reference to a gesture input system for manipulating a computer environment, it is also envisioned that user interaction with and/or manipulation of the computer environment may also be achieved using other devices such as a mouse, a trackball, a keyboard, a touch-sensitive display, a pointing device (e.g., a pen), a haptic device, etc.

Further variations of the present system would readily occur to a person of ordinary skill in the art and are encompassed by the following claims. Through operation of the present system, a virtual environment solicitation is provided to a user to enable simple immersion into a virtual environment and its objects.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. An endoscope, comprising:
a rigid section having first and second ends, and a cavity situated between the first and second ends, the rigid section having a longitudinal length and defining a longitudinal axis (LAR);
a flexible section having proximal and distal ends, the proximal end coupled to the second end of the rigid section;
an imager having first and second ends and a cavity situated between the first and second ends of the imager, the second end of the imager being coupled to the distal end of the flexible section; and
an objective lens assembly within the cavity of the imager, the objective lens assembly including a first lens group near an object of interest, a second lens group away from the object of interest, a single dual aperture lens having a limiting aperture portion with a complementary multiband bandpass filter (CMBF) pair situated within the cavity of the imager between the first lens group and the second lens group for filtering right and left image rays passing through the CMBF pair to output filtered right and left image rays;
wherein the imager receives the filtered right and left image rays and forms corresponding video information for stereoscopic imaging, and
wherein the second lens group includes an achromatic doublet lens for receiving the filtered right and left image rays from the first lens group and a further doublet lens located between the achromatic doublet lens and the imager, the further doublet lens having a focal length which is less than a focal length of the achromatic doublet lens.

2. The endoscope of claim 1, wherein the right and left image rays which pass through the CMBF pair have a minimal angle of incidence (AOI) which is less than or equal to a threshold angle of incidence (TAOI) value.

3. The endoscope of claim 2, wherein the TAOI value is 25 degrees.

4. The endoscope of claim 1, wherein the CMBF pair includes two filters having different passbands that do not overlap and is formed on the single dual aperture lens that receives both the right and left image rays for providing the filtered right and left image rays to the imager, the first lens group providing the right and left image rays to the CMBF pair and the second lens group focusing the filtered right and left image rays on an imaging plane of the imager.

5. The endoscope of claim 4, wherein the single dual aperture lens including the CMBF pair is formed upon a surface of the achromatic doublet lens of the second lens group facing the first lens group, the second lens group directly focusing the filtered right and left image rays on the imaging plane.

6. The endoscope of claim 1, wherein the CMBF pair is coated on the limiting aperture portion.

7. An endoscope, comprising:
a rigid section having first and second ends, and a cavity situated between the first and second ends, the rigid section having a longitudinal length and defining a longitudinal axis (LAR);
a flexible section having proximal and distal ends, the proximal end coupled to the second end of the rigid section;
an imager having first and second ends and a cavity situated between the first and second ends of the imager, the second end of the imager being coupled to the distal end of the flexible section; and
an objective lens assembly within the cavity of the imager, the objective lens assembly including a first lens group near an object of interest, a second lens group away from the object of interest, and a complementary multiband bandpass filter (CMBF) pair situated within the cavity of the imager between the first lens group and the second lens group for filtering right and left image rays passing through the CMBF pair to output filtered right and left image rays,
wherein imager receives the filtered right and left image rays and forms corresponding video information for stereoscopic imaging, and
wherein the second lens group includes an achromatic doublet lens for receiving the filtered right and left image rays from the first lens group and a further doublet lens located between the achromatic doublet lens and the imager, the further doublet lens having a focal length which is less than a focal length of the achromatic doublet lens.

8. An endoscope, comprising:
an imager; and
an objective lens assembly coupled to the imager for forming stereoscopic images,
wherein the objective lens assembly includes a first lens group near an object of interest, a second lens group away from the object of interest, a dual aperture lens, and a complementary multiband bandpass filter (CMBF) pair situated between the first lens group and the second lens group for filtering right and left image rays passing through the CMBF pair to output filtered right and left image rays, and
wherein the second lens group includes an achromatic doublet lens for receiving the filtered right and left image rays from the first lens group and a further doublet lens located between the achromatic doublet lens and the imager, the further doublet lens having a focal length which is less than a focal length of the achromatic doublet lens.

9. An endoscope, comprising:
an imager; and
an objective lens assembly,
wherein the objective lens assembly includes a first lens group near an object of interest, a second lens group away from the object of interest, and a filter situated between the first lens group and the second lens group, and
wherein the second lens group includes an achromatic doublet lens for receiving filtered right and left image rays from the filter and a further doublet lens located between the achromatic doublet lens and the imager, the further doublet lens having a focal length which is less than a focal length of the achromatic doublet lens,
wherein the objective lens assembly includes a dual aperture lens having a limiting aperture portion, wherein the filter is a complementary multiband bandpass filter (CMBF) pair formed over the dual aperture lens, and wherein the endoscope comprises:
an illuminator source for illuminating the object of interest; and a controller configured to control at least one of the limiting aperture portion and the illuminator source to vary amount of light passing through the limiting aperture.

10. The endoscope of claim 9, wherein the CMBF pair is configured to filter right and left image rays passing through the CMBF pair to provide the filtered right and left image rays to the imager for forming a three-dimensional stereoscopic image, wherein the dual aperture lens is a single dual aperture lens, and wherein the CMBF pair includes two filters having different passbands that do not overlap and is formed on the single dual aperture lens that receives the right and left image rays for providing the filtered right and left image rays to the imager, the first lens group providing the right and left image rays to the CMBF pair and the second lens group focusing the filtered right and left image rays on an imaging plane of the imager.

11. An endoscope, comprising:
an imager; and
an objective lens assembly coupled to the imager for forming stereoscopic images,
wherein the objective lens assembly includes a first lens group near an object of interest, a second lens group away from the object of interest, a dual aperture lens, and a complementary multiband bandpass filter (CMBF) pair situated between the first lens group and the second lens group for filtering right and left image rays passing through the CMBF pair to output filtered right and left image rays,
wherein the imager comprises a detector array at an imaging plane, wherein the second lens group is configured to focus the filtered right and left image rays on the imaging plane, wherein the detector array is configured to detect the filtered right and left image rays focused upon the imaging plane to form corresponding stereoscopic image information, and
wherein the second lens group includes an achromatic doublet lens for receiving the filtered right and left image rays from the first lens group and a further doublet lens located between the achromatic doublet lens and the imager, the further doublet lens having a focal length which is less than a focal length of the achromatic doublet lens.

12. The endoscope of claim 10, wherein the single dual aperture lens including the CMBF pair is formed upon a surface of the achromatic doublet lens of the second lens group facing the first lens group, the second lens group directly focusing the filtered right and left image rays on the imaging plane.

13. An endoscope, comprising:
an imager; and
an objective lens assembly,
wherein the objective lens assembly includes a first lens group near an object of interest, a second lens group away from the object of interest, and a filter situated between the first lens group and the second lens group, and wherein the second lens group includes an achromatic doublet lens for receiving filtered right and left image rays from the filter and a further doublet lens located between the achromatic doublet lens and the imager, the further doublet lens having a focal length which is less than a focal length of the achromatic doublet lens,
wherein the objective lens assembly includes a dual aperture lens and a complementary multiband bandpass filter (CMBF) pair, the dual aperture lens having a limiting aperture portion, and CMBF pair being situated between the first lens group and the second lens group for filtering right and left image rays passing through the CMBF pair to provide the filtered right and left image rays to the imager for forming a three-dimensional stereoscopic image, and wherein the CMBF pair is coated on the limiting aperture portion.

14. The endoscope of claim 13, further comprising a controller configured to control the limiting aperture portion to provide a two-dimensional image based on image rays passing through one aperture of the dual aperture lens or to provide the three-dimensional stereoscopic image based on the filtered right and left image rays provided by the CMBF pair.

15. An endoscope, comprising:
an imager having an objective lens assembly, the objective lens assembly including a first lens group near an object of interest, a second lens group away from the object of interest, and a limiting aperture portion with a complementary multiband bandpass filter (CMBF) pair between the first and second lens groups for filtering right and left image rays passing through the CMBF pair to output filtered right and left image rays;
an illuminator source for illuminating the object of interest for reflection as reflected light; and
a controller configured to control the illuminator source to vary an amount of light provided by the illuminator source to provide a desired intensity of the reflected light to the dual aperture lens and to control the limiting aperture portion to vary an amount of light passing through the limiting aperture portion to provide images having desired intensities including providing a two-dimensional image based on image rays passing through one aperture of the dual aperture lens or providing a three-dimensional image based on the filtered right and left image rays,
wherein the second lens group includes an achromatic doublet lens for receiving the filtered right and left image rays from the first lens group and a further doublet lens located between the achromatic doublet lens and the imager, the further doublet lens having a focal length which is less than a focal length of the achromatic doublet lens.

16. The endoscope of claim 15, wherein the controller configured to control the illuminator source and the limiting aperture portion based on an intensity of at least one of the filtered right and left image rays.

* * * * *